(12) United States Patent
Sampathkumar et al.

(10) Patent No.: US 9,969,763 B2
(45) Date of Patent: May 15, 2018

(54) 1,2,3-TRIAZOLE-TETHERED CARBOHYDRATE-DI AND TRI LIPIDATED CYSTEINE CONJUGATES USEFUL AS VACCINE ADJUVANTS AND PROCESS FOR PREPARATION THEREOF

(71) Applicant: Council of Scientific and Industrial Research, New Delhi (IN)

(72) Inventors: Halmuthur Mahabalarao Sampathkumar, Hyderabad (IN); Naresh Nalla, Hyderabad (IN); Sathyaseelan Sathyabama, Hyderabad (IN); Sabbana Surya Vamshi, Hyderabad (IN); Bonam Srinivasa Reddy, Hyderabad (IN); Veerjala Naveen Kumar, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 66 days.

(21) Appl. No.: 14/991,037

(22) Filed: Jan. 8, 2016

(65) Prior Publication Data
US 2016/0200758 A1 Jul. 14, 2016

(30) Foreign Application Priority Data

Jan. 9, 2015 (IN) .............................. 77/DEL/2015

(51) Int. Cl.
| | |
|---|---|
| C07H 19/056 | (2006.01) |
| A61K 39/39 | (2006.01) |
| C07D 249/04 | (2006.01) |
| C12N 7/00 | (2006.01) |
| A61K 39/29 | (2006.01) |
| A61K 39/12 | (2006.01) |
| A61K 39/00 | (2006.01) |

(52) U.S. Cl.
CPC .......... *C07H 19/056* (2013.01); *A61K 39/12* (2013.01); *A61K 39/292* (2013.01); *A61K 39/39* (2013.01); *C07D 249/04* (2013.01); *C12N 7/00* (2013.01); *A61K 2039/55511* (2013.01); *A61K 2039/55572* (2013.01); *A61K 2039/60* (2013.01); *C12N 2730/10134* (2013.01)

(58) Field of Classification Search
CPC .... C07H 19/056; C07D 249/04; A61K 39/39; A61K 39/292; C12N 7/00; C12N 30/10134
USPC ......................................................... 514/54
See application file for complete search history.

(56) References Cited

PUBLICATIONS

Akira, Shizuo, et al., "Pathogen Recognition and Innate Immunity", *Cell*, 124(4), (2006), 783-801.

Bagchi, Aranya, et al., "MyD88-Dependent Synergy and MyD88-Independent Pathways in Synergy, Priming, and Tolerance between TLR Agonists", *J. Immun.*, 178, (2007), 1164-1171.

Basith, Shaherin, "Toll-like receptor modulators: a patent review (2006-2010)", *Expert Opin. Ther. Patents*, 21(6), (2011), 927-944.

Benoist, Eric, et al., "A Click procedure with heterogeneous copper to tether technetium-99m chelating agents and rhenium complexes. Evaluation of the chelating properties and biodistribution of the new radiolabelled glucose conjugates", *Carbohydrate Research*, 346(1-3), (2011), 26-34.

Berg, Michaela, et al., "Synthetic lipopeptide $Pam_3CysSer(Lys)_4$ is an effective activator of human platelets", *American Journal of Physiology—Cell Physiology*, 266(6), (1994), C1684-C1691.

Dempsey, Paul W., et al., "C3d of Complement as a Molecular Adjuvant: Bridging Innate and Acquired Immunity", *Science* 271(5247), (1996), 348-350.

Deres, Karl, et al., "In vivo priming of virus-specific cytotoxic T lymphocytes with synthetic lipopeptide vaccine", *Nature*, 342, (1989), 561-564.

Gavin, Amanda L., et al., "Adjuvant-Enhanced Antibody Responses in the Absence of Toll-Like Receptor Signaling", *Science*, 314(5807), (2006), 1936-1938.

Metzger, Jörg, et al., "Synthesis of novel immunologically active tripalmitoyl-S-glycerylcysteinyl lipopeptides as useful intermediates for immunogen preparations", *Int J Peptide Protein Res* 37(1), (1991), 46-57.

Milich, David R., et al., "T and B cell Recognition of Native and Synthetic Pre-S Region Determinants on Hepatitis-B Surface Antigen", In: *Vaccines 86 New Approaches to Immunization*, Brown F., et al, Editors, Cold Spring Laboratory, (1986), 377-382.

Schild, Hansjorg, et al., "Efficiency of peptides and lipopeptides for in vivo priming of virus-specific cytotoxic T cells", *Eur J Immunol*, 21(11), (1991), 2649-2654.

Smith, Sinead M., et al., "Tribbles 3: A Novel Regulator of TLR2-Mediated Signaling in Response to *Helicobacter pylori* Lipopolysaccharide", *J. Immunology*, 186, (2011), 2462-2471.

(Continued)

*Primary Examiner* — Shaojia Anna Jiang
*Assistant Examiner* — Michael C Henry
(74) *Attorney, Agent, or Firm* — Schwegman Lundberg & Woessner, P.A.

(57) ABSTRACT

The present invention relates to carbohydrate-di and tri lipidated cysteine based 1,2,3-triazoles useful as vaccine adjuvants of formula 1

Formula 1

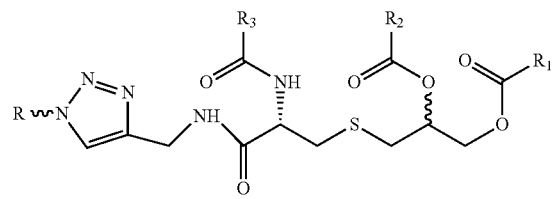

The present invention also provides process for preparation of carbohydrate-di and tri lipidated cysteine based 1,2,3-triazoles. The carbohydrate-di and tri lipidated cysteine based 1,2,3-triazoles as vaccine adjuvants are useful in formulations for therapeutic and prophylactic vaccines against bacterial, viral, protozoan infections and cancer.

7 Claims, 1 Drawing Sheet

(56) References Cited

PUBLICATIONS

Srihari, P., et al., "Stereoselective total synthesis of synparvolide B and epi-synparvolide A", *Tetrahedron Letters*, 50(20), (2009), 2420-2424.

Trinchieri, Giorgio, et al., "Cooperation of Toll-like receptor signals in innate immune defence", *Nat Rev Immunol*, 7(3), (2007), 179-190.

Yoder, Alyson, et al., "Tripalmitoyl-S-Glyceryl-Cysteine-Dependent OspA Vaccination of Toll-Like Receptor 2-Deficient Mice Results in Effective Protection from Borrelia burgdorferi Challenge", *Infect. Immun.*, 71(7), (2003), 3894-3900.

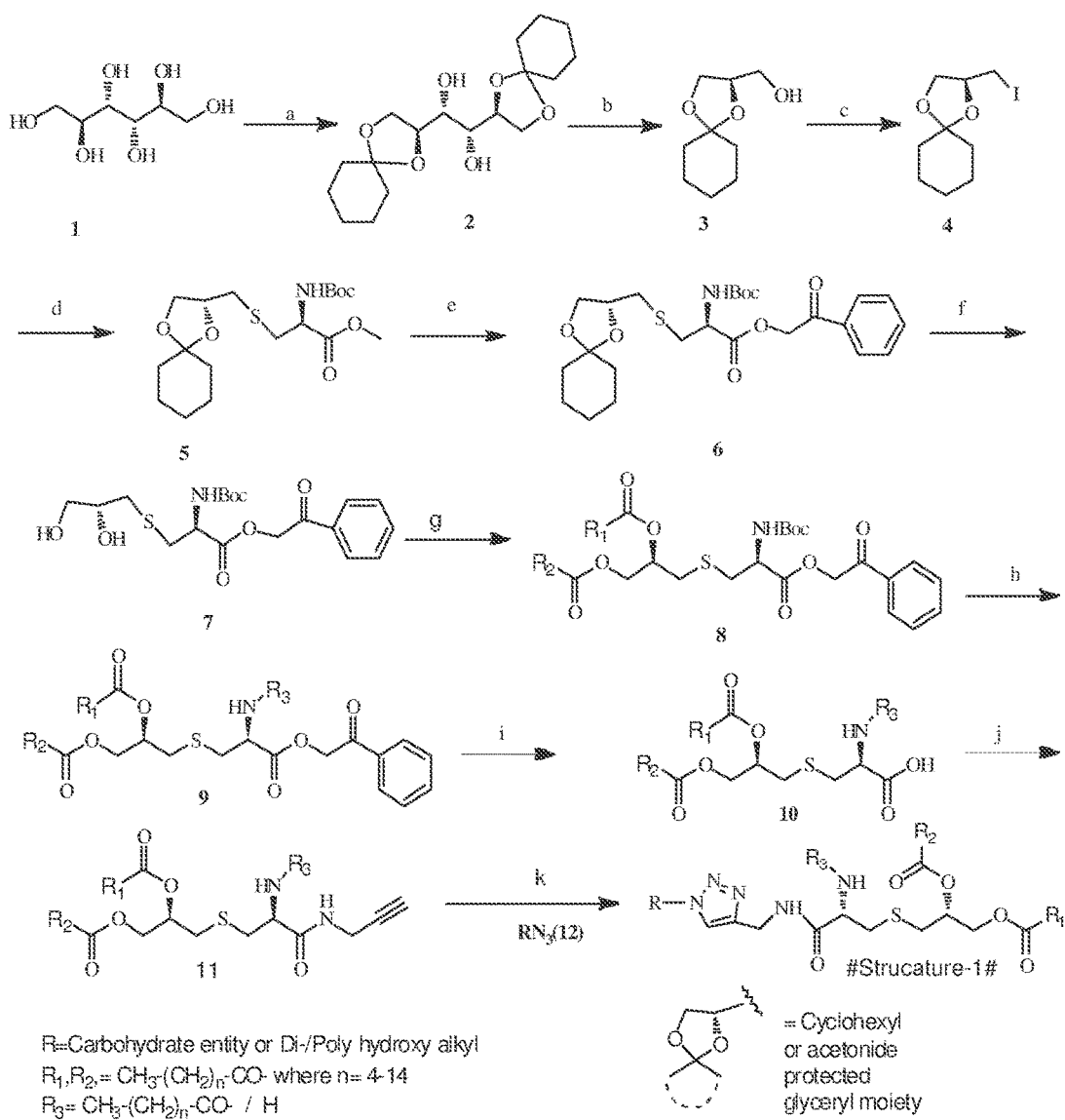

1,2,3-TRIAZOLE-TETHERED CARBOHYDRATE-DI AND TRI LIPIDATED CYSTEINE CONJUGATES USEFUL AS VACCINE ADJUVANTS AND PROCESS FOR PREPARATION THEREOF

CLAIM OF PRIORITY

This application claims the benefit of priority of India Patent Application No. 77/DEL2015, filed on 9 Jan. 2015, the benefit of priority of which is claimed hereby, and which is incorporated by reference herein in its entirety.

FIELD OF THE INVENTION

The present invention relates to carbohydrate-di and tri lipidated cysteine based 1,2,3-triazoles useful as vaccine adjuvants for general formula 1 and representative compounds thereof.

Formula 1

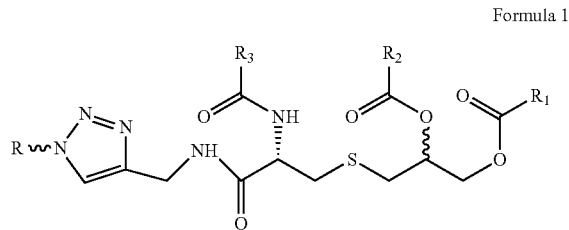

Particularly the present invention relates to the process for preparation of carbohydrate-di and tri lipidated cysteine based 1,2,3-triazoles. More particularly the present invention relates to the use of carbohydrate-di and tri lipidated cysteine based 1,2,3-triazoles as vaccine adjuvants in formulations for therapeutic and prophylactic vaccines against bacterial, viral, protozoan infections and cancer.

BACKGROUND OF THE INVENTION

An "adjuvant" is a substance that itself is often biologically inactive but which, in conjunction with a given antigen, enhances its antigenic capabilities. An adjuvant plays key role in promoting immune responses by accelerating or amplifying one or more specific phases of various immune responses. One advantage of the use of adjuvants in vaccines lies in the fact that the same degree of antibody response can be achieved with a smaller amount of antigen. Adjuvants are particularly useful in cases where the antigen alone does not stimulate high levels of antibody. Thus, the main functions of an adjuvant is to enhance the antibody response to levels which will ensure protection against an infectious disease. An ideal adjuvant should also up regulate the expression of cytokines responsible for T-helper cell activation essential for evoking immune memory and cell mediated immunity. Any material used as an adjuvant in vaccines should be non-toxic, relatively easily metabolized and produce little or no skin reaction at the injection site. Adjuvants have been used experimentally in animals for studies on the immune system and in vaccines for improvement of immunological responses and the enhancing effects have, in many instances, been confirmed by application to humans. Prior art adjuvants range in type from simple inorganic materials, such as, aluminum phosphate, to complex mixtures, such as, Freund's adjuvant, which is a homogenate of oil, detergent and killed tubercle bacilli.a\Typical examples of such adjuvants are aluminum hydroxide or phosphate or calcium salts (alum), non-ionic block polymer surfactants, an oil emulsion (Freund's adjuvant), and emulsion encompassing pathogen associated molecular patterns such as monophosphoryl lipid A (MPL), lipopolysaccharides, mycobacteria, muramyl dipeptides (MDP) tetanus toxoid, CpG, etc. plant derived Quillaja saponins (QS21).

Since the use of a protein antigen alone does not necessarily induce an adequately strong immune response, vaccine compositions normally contain an antigen in combination with an adjuvant. Adjuvants provide additional signal required by the antigen generated by the interaction with co-stimulatory molecule(s). In this regard, the adjuvant may be able to strengthen the signal generated by co-stimulatory molecules such as CD 40. CD 80, and CD 86 on antigen presenting cell (DC). It also induces MHC molecules and specific cytokines leading to Th1 activation and help in achieving the required level of TH1/Th2 bias for any specific vaccine. Th1 type immune response leads to the increase of IgG2a generation and induces a powerful cell mediated immune response.

Some antigens such as lipoproteins, glycoproteins, or whole microorganisms can act both as an epitope and an adjuvant in the form of a pathogen associated molecular pattern (PAMP). Even though the primary structure of a protein antigen, cannot be altered, the PAMP moiety of an antigen can be modified through the addition of a specific adjuvant or related immune potentiators to influence immunogenicity (Dempsey P W et al., Science 271: 348-350, 1996; Deres K et al, Nature 342: 561-564, 1989). Thus, the modification of a molecular pattern of an antigen can increase immunogenicity and help to achieve qualitatively specific immune response. (Milich D R et al., 1986, New Approaches to Immunization, pp 377-382. Cold Spring Harbor Laboratories, New York). The stimulation of Toll-Like Receptors (TLRs)present at the surface of antigen presenting cells (APCs) is now an established approach to triggering and boosting the immune response. Many compounds have been described as agonists of the TLRs, especially the TLR2 subtype [2], and as a consequence, can be considered as potential immune adjuvants. For example, very complex lipopeptides like macrophage-activating lipopeptide-2 [3](MALP-2)analogs i.e. Pam2Cys-GDPKH-PKSF [(a) Akira, S et al. Cell 2006, 124, 783-801.]. Pam2Cys-GDPKHPKSFTGWVA representing the N-terminal part of the 44-kDa lipoprotein LP44 of *Mycoplasma salivarium* [Basith, S et al. Expert Opin. Ther. Patents 2011, 21, 927-944.], or Braun lipoprotein [x] have all been described as TLR2 agonists. On the other hand, simpler synthetic S-[2,3-bispalmitoyloxy-(2R)-propyl]-Rcysteinyl lipopeptides, like 'Pam2CAG' or Pam3CSK4 [Berg, M et al. American Journal of Physiology 1994, 266, 1684-1691], have also shown TLR2 agonist activity and can therefore be considered as more useful and easily attainable immunoadjuvants. In these constructs, the Pam2C (or Pam3C) template is necessary but not sufficient to stimulate the TLR2 receptor and a substitution of the cysteine is required to establish agonist activity. While lysine derivatives generally improve the activity of TLR2/6 agonists, it was also shown that Pam2CSK, the smallest lysine-containing compound, has no cytokine-inducing activity [Bessler, W. G et al Journal of Immunology 1985, 135, 1900-1905]. In this context, two lysines are usually needed to recover activity, which confer positive charges and above all highly amphiphilic properties that complicate the preparation of the vaccine cocktail. Recently, Pam2CS and its analogs have been synthesized and have shown good NF-kB inducing activity [Sinéad M.

Smith et al J. Immunology, 2011, 186, 4, 2462-2471]. Nevertheless, their effects on DC and B-lymphocyte maturation and cytokine secretion have not yet been demonstrated. Glycolipids of the type Pam2Cys-α-Galactose as immunoadjuvants has been reported to have several folds increase in cell proliferation and DC maturation attributes when comparable with standard Pam2cysCAG or Pam3cysCAG.

A lipopeptide was first synthesized by Metzger et al. as a synthetic analogue of lipopeptide originated from bacteria and *mycoplasma* (Metzger J et al., Int J Peptide Protein Res 37:46-57, 1991). Since then, numerous analogues have been synthesized (EMC microcollections GmbH Sindelfinger Str. 3 72070 Tubingen. Germany). There is a report that virus-specific cytotoxic T lymphocyte (CTL) was induced by administrating a mouse with Pam3Cys-Ser-Ser, a lipopeptide conjugated with influenza virus T cell epitope (Schild H et al., Eur J Immunol 21:2649-2654, 1991). In general, the lipopeptide has been known as a TLR 2 ligand (Trinchieri G & Sher A, Nat Rev Immunol 7:179-190, 2007). These types of natural adjuvants associated with the antigens, however, often may not be strong enough to induce a desired strength and a quality of immune response, requiring a good adjuvant in a vaccine formulation.

Developing a good adjuvant is accordingly a very important job in developing a good vaccine, but adjuvant development still has to rely mainly on empirical work. For example, Toll Like Receptors (TLR)are the most important PRR on antigen presenting cells (APC) involved in the activation of APC and in antigen presentation by APC. Potent antibody response, however, is not entirely dependent on TLR signals (Gavin. A. L. et al, Science 314:1936-1938, 2006). Further. Pam3cys, which is a TLR2 ligand, works in inducing immune response independently of TLR2 (Yoder et al. Infect. Immun. 71:3894-3900, 2003). Accordingly, although Pam2Cys and a galactosyl moiety covalently linked together is known to be synergistic in inducing antibody and cytokine response (Bagchi et at J. Immun. 178:1164-1171, 2007), there has been no prior art of a well balanced powerful vaccine adjuvant function of a bioconjugate encompassing any carbohydrate moiety and a di or triacyl cystenyl lipid head group linked through a 1,2,3-triazolyl methyl amine spacer. Since, good protective immunity requires balanced immune response comprising both strong cell mediated immune response and humoral antibody response, developing an adjuvant that aid such powerful and synergestic immune response is an important endeavor in vaccine research.

OBJECTIVES OF THE INVENTION

The main objective of the present invention is to provide 1,2,3-Triazole-tethered carbohydrate-di and tri lipidated cysteine based conjugates as TLR-2 agonists useful as vaccine adjuvant. Another object of the present invention is to provide a process for the preparation of 1,2,3-Triazole-tethered carbohydrate-di and tri lipidated cysteine based conjugates as vaccine adjuvant. Yet another objective of the present invention is to test the efficacy of the molecules thus generated as adjuvants against specific antigen or weak ovalbumin on small animal models which provides basis for their use in prophylactic and therapeutic vaccines.

Still another object of present invention is to provide a series of compounds combining a hydrophobic moiety endowed with TLR agonist properties (TLR2 principally) with a carbohydrate entities through a spacer encompassing a 1,2,3-triazolyl methyl amine moiety. It is another object of the present invention to provide an adjuvant composition that can be used in a vaccine formulation to induce a strong humoral immune response and cell mediated immune response. It is another object of the present invention to provide a method for generating an appropriate, high quality antibody using said adjuvant composition.

Yet another object of the present invention to provide a method for enhancing a Th1 immune response using said adjuvant composition. It is another object of the present invention to provide an adjuvant composition to prepare a prophylactic vaccine for bacterial, viral or parasite infection, containing said adjuvant composition and at least one antigen.

Still another object of the present invention to provide an adjuvant composition to prepare a preventive or therapeutic vaccine against cancer, containing said adjuvant composition and at least one cancer-specific antigen.

SUMMARY OF THE INVENTION

Accordingly, the present invention provides a vaccine adjuvant conjugate of Formula (1)

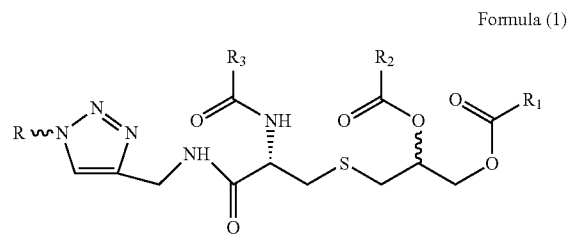

Formula (1)

comprising tri or di lipidated cysteine, and a carbohydrate linked together through a 1,2,3-triazolyl methyl amine moiety through alpha or beta linkage Wherein
R is selected from pyranose or furanose based monosaccharide, disaccharides, trisaccharides and oligosaccharide comprising four or more than four carbohydrate units of same type or different types.

$R_1$, $R_2$ is selected from alkyl ($C_4$-$C_{18}$), alkenyl ($C_4$-$C_{18}$), alkynyl ($C_4$-$C_{18}$) either linear and branched, arylalkyl ($C_4$-$C_{18}$), cycloalkyl ($C_4$-$C_{18}$), triterpinyl ($C_4$-$C_{18}$) lipid entity with or without any heteroatoms.

$R_3$ is selected from hydrogen, alkyl ($C_4$-$C_{18}$), alkenyl ($C_4$-$C_{18}$), alkynyl ($C_4$-$C_{18}$) either linear and branched, arylalkyl ($C_4$-$C_{18}$), cycloalkyl ($C_4$-$C_{18}$), triterpinyl ($C_4$-$C_{18}$) lipid entity with or without any heteroatoms.

In an embodiment of the present invention, the said vaccine adjuvant conjugate are selected from the group consisting of:

(R)-3-((S)-2-amino-3-((1-((R)-2,3-dihydroxypropyl)-1H-1,2,3-triazol-4-yl)amino)-3-oxopropylthio)propane-1,2-diyl dihexanoate. (7a); (2R)-3-((2S)-2-amino-3-oxo-3-((1-((2S)-3,4,5-trihydroxy-6-(hydroxymethyl)tetrahydro-2H-pyran-2-yl)-1H-1,2,3-triazol-4-yl)amino)propylthio) propane-1,2-diyl dihexanoate (7b); (2R)-3-((2S)-2-amino-3-((1-((2S)-2-hydroxy-2-((3S,4S)-3,4,5-trihydroxytetra-hydrofuran-2-yl)ethyl)-1H-1,2,3-triazol-4-yl)amino)-3-oxopropylthio)propane-1,2-diyl dihexanoate. (7c); (R)-3-((S)-2-amino-3-oxo-3-((1-((2S,3S,4R,5R)-2,3,4,5,6-pentahydroxyhexyl)-1H-1,2,3-triazol-4-yl)amino)propylthio)propane-1,2-diyl dihexanoate. (7d); (2R)-3-((2S)-2-amino-3-((1-((2S,3R,4S)-3,4-dihydroxy-5-(hydroxymethyl)tetrahydrofuran-2-yl)-1H-

1,2,3-triazol-4-yl)amino)-3-oxopropylthio)propane-1,2-diyl dihexanoate. (7e); (2R)-3-((2S)-2-amino-3-((1-((2S,3S,4S)-3,4-dihydroxy-5-(hydroxymethyl)tetrahydrofuran-2-yl)-1H-1,2,3-triazol-4-yl)amino)-3-oxopropylthio)propane-1,2-diyl dihexanoate. (7f); (2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dihexanoate. (7g); (2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dihexanoate. (7h); (2R)-3-((2S)-2-amino-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl dihexanoate. (7i); (2R)-3-((2S)-2-amino-3-oxo-3-((1-((3,4,5,6-tetrahydroxytetrahydro-2H-pyran-2-yl)methyl)-1H-1,2,3-triazol-4-yl)amino)propylthio)propane-1,2-diyl dihexanoate. (7j); (2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl dihexanoate. (7k); (2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl dihexanoate. (7l); (R)-3-((S)-2-amino-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl diheptanoate. (7m); (R)-3-((S)-2-amino-3-((1-((R)-2,3-dihydroxypropyl)-1H-1,2,3-triazol-4-yl)methylamino)-3-oxopropylthio)propane-1,2-diyl diheptanoate. (8a); (2R)-3-((2S)-2-amino-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl diheptanoate. (8b); (2R)-3-((2S)-2-amino-3-((1-((2S)-2-hydroxy-2-((3S,4S)-3,4,5-trihydroxytetrahydrofuran-2-yl)ethyl)-1H-1,2,3-triazol-4-yl)amino)-3-oxopropylthio)propane-1,2-diyl diheptanoate(8c); (R)-3-((S)-2-amino-3-oxo-3-((1-((2S,3S,4R,5R)-2,3,4,5,6-pentahydroxyhexyl)-1H-1,2,3-triazol-4-yl)amino)propylthio)propane-1,2-diyl diheptanoate.(8d); (2R)-3-((2S)-2-amino-3-((1-((2S,3R,4S)-3,4-dihydroxy-5-(hydroxymethyl)tetrahydrofuran-2-yl)-1H-1,2,3-triazol-4-yl)amino)-3-oxopropylthio)propane-1,2-diyl diheptanoate. (8e); (2R)-3-((2S)-2-amino-3-((1-((2S,3S,4S)-3,4-dihydroxy-5-(hydroxymethyl)tetrahydrofuran-2-yl)-1H-1,2,3-triazol-4-yl)amino)-3-oxopropylthio)propane-1,2-diyl diheptanoate. (8f); (2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl diheptanoate. (8g); (2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl diheptanoate. (8h); (2R)-3-((2S)-2-amino-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl diheptanoate. (8i); (2R)-3-((2S)-2-amino-3-oxo-3-((1-((3,4,5,6-tetrahydroxytetrahydro-2H-pyran-2-yl)methyl)-1H-1,2,3-triazol-4-yl)amino)propylthio)propane-1,2-diyl diheptanoate. (8j); (2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl diheptanoate. (8k); (2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl diheptanoate. (8l); (R)-3-((S)-2-amino-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl diheptanoate. (8m); (R)-3-((S)-2-amino-3-((1-((R)-2,3-dihydroxypropyl)-1H-1,2,3-triazol-4-yl)amino)-3-oxopropylthio)propane-1,2-diyl dioctanoate. (9a); (2R)-3-((2S)-2-amino-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl dioctanoate. (9b); (2R)-3-((2S)-2-amino-3-((1-((2S)-2-hydroxy-2-((3S,4S)-3,4,5-trihydroxytetrahydrofuran-2-yl)ethyl)-1H-1,2,3-triazol-4-yl)amino)-3-oxopropylthio)propane-1,2-diyl dioctanoate. (9c); (R)-3-((S)-2-amino-3-oxo-3-((1-((2S,3S,4R,5R)-2,3,4,5,6-pentahydroxyhexyl)-1H-1,2,3-triazol-4-yl)amino)propylthio)propane-1,2-diyl dioctanoate. (9d); (2R)-3-((2S)-2-amino-3-((1-((2S,3R,4S)-3,4-dihydroxy-5-(hydroxymethyl)tetrahydrofuran-2-yl)-1H-1,2,3-triazol-4-yl)amino)-3-oxopropylthio)propane-1,2-diyl dioctanoate. (9e); (2R)-3-((2S)-2-amino-3-((1-((2S,3S,4S)-3,4-dihydroxy-5-(hydroxymethyl)tetrahydrofuran-2-yl)-1H-1,2,3-triazol-4-yl)amino)-3-oxopropylthio)propane-1,2-diyl dioctanoate. (9f); (2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dioctanoate. (9g); (2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dioctanoate. (9h); (2R)-3-((2S)-2-amino-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl dioctanoate. (9i); (2R)-3-((2S)-2-amino-3-oxo-3-((1-((3,4,5,6-tetrahydroxytetrahydro-2H-pyran-2-yl)methyl)-1H-1,2,3-triazol-4-yl)amino)propylthio)propane-1,2-diyl dioctanoate. (9j); (2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl dioctanoate. (9k); (2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl dioctanoate. (9l); (R)-3-((S)-2-amino-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl dioctanoate. (9m); (R)-3-((S)-2-amino-3-((1-((R)-2,3-dihydroxypropyl)-1H-1,2,3-triazol-4-yl)amino)-3-oxopropylthio)propane-1,2-diyl dinonanoate. (10a); (2R)-3-((2S)-2-amino-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl dinonanoate. (10b); (2R)-3-((2S)-2-amino-3-((1-((2S)-2-hydroxy-2-((3S,4S)-3,4,5-trihydroxytetraiydrofuran-2-yl)ethyl)-1H-1,2,3-triazol-4-yl)amino)-3-oxopropylthio)propane-1,2-diyl dinonanoate. (10c); (R)-3-((S)-2-amino-3-oxo-3-((1-((2S,3S,4R,5R)-2,3,4,5,6-pentahydroxyhexyl)-1H-1,2,3-triazol-4-yl)amino)propylthio)propane-1,2-diyl dinnonanoate. (10d); (2R)-3-((2S)-2-amino-3-((1-((2S,3R,4S)-3,4-dihydroxy-5-(hydroxymethyl)tetrahydrofuran-2-yl)-1H-

1,2,3-triazol-4-yl)amino)-3-oxopropylthio)propane-1,2-diyl dinonanoate. (10e); (2R)-3-((2S)-2-amino-3-((1-((2S,3S,4S)-3,4-dihydroxy-5-(hydroxymethyl)tetrahydrofuran-2-yl)-1H-1,2,3-triazol-4-yl)amino)-3-oxopropylthio)propane-1,2-diyl dinonanoate. (10f); (2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dinonanoate. (10g); (2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dinonanoate. (10h); (2R)-3-((2S)-2-amino-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl dinonanoate. (10i); (2R)-3-((2S)-2-amino-3-oxo-3-((1-(3,4,5,6-tetrahydroxytetrahydro-2H-pyran-2-yl)methyl)-1H-1,2,3-triazol-4-yl)amino)propylthio)propane-1,2-diyl dinonanoate. (10j); (2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl dinonanoate. (10k); (2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl dinonanoate. (10l); (R)-3-((S)-2-amino-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl dinnonanoate. (10m); (R)-3-((S)-2-amino-3-((1-((R)-2,3-dihydroxypropyl)-1H-1,2,3-triazol-4-yl)amino)-3-oxopropylthio)propane-1,2-diyl bis(decanoate). (11a); (2R)-3-((2S)-2-amino-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl bis(decanoate). (11b); 2R)-3-((2S)-2-amino-3-((1-((2S)-2-hydroxy-2-((3S,4S)-3,4,5-trihydroxytetrahydrofuran-2-yl)ethyl)-1H-1,2,3-triazol-4-yl)amino)-3-oxopropylthio)propane-1,2-diyl bis(decanoate). (11c); (R)-3-((S)-2-amino-3-oxo-3-((1-((2S,3S,4R,5R)-2,3,4,5,6-pentahydroxyhexyl)-1H-1,2,3-triazol-4-yl)amino)propylthio)propane-1,2-diyl bis(decanoate). (11d); (2R)-3-((2S)-2-amino-3-((1-((2S,3R,4S)-3,4-dihydroxy-5-(hydroxymethyl)tetrahydrofuran-2-yl)-1H-1,2,3-triazol-4-yl)amino)-3-oxopropylthio)propane-1,2-diyl bis(decanoate). (11e); (2R)-3-((2S)-2-amino-3-((1-((2S,3S,4S)-3,4-dihydroxy-5-(hydroxymethyl)tetrahydrofuran-2-yl)-1H-1,2,3-triazol-4-yl)amino)-3-oxopropylthio)propane-1,2-diyl bis(decanoate). (11f); (2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl bis(decanoate). (11g); (2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl bis(decanoate). (11h); (2R)-3-((2S)-2-amino-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl bis(decanoate). (11i); (2R)-3-((2S)-2-amino-3-oxo-3-((1-((3,4,5,6-tetrahydroxytetrahydro-2H-pyran-2-yl)methyl)-1H-1,2,3-triazol-4-yl)amino)propylthio)propane-1,2-diyl bis(decanoate). (11j); (2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl bis(decanoate). (11k); (2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl bis(decanoate). (11l); (R)-3-((S)-2-amino-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl bis(decanoate). (11m); (R)-3-((S)-2-amino-3-((1-((R)-2,3-dihydroxypropyl)-1H-1,2,3-triazol-4-yl)amino)-3-oxopropylthio)propane-1,2-diyl diundecanoate. (12a); (2R)-3-((2S)-2-amino-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyldiundecanoate. (12b); (2R)-3-((2S)-2-amino-3-((1-(2S)-2-hydroxy-2-((3S,4S)-3,4,5-trihydroxytetrahydrofuran-2-yl)ethyl)-1H-1,2,3-triazol-4-yl)amino)-3-oxopropylthio)propane-1,2-diyldiundecanoate. (12c); (R)-3-((S)-2-amino-3-oxo-3-((1-((2S,3S,4R,5R)-2,3,4,5,6-pentahydroxyhexyl)-1H-1,2,3-triazol-4-yl)amino)propylthio)propane-1,2-diyl diundecanoate. (12d); (2R)-3-((2S)-2-amino-3-((1-((2S,3R,4S)-3,4-dihydroxy-5-(hydroxymethyl)tetrahydrofuran-2-yl)-1H-1,2,3-triazol-4-yl)amino)-3-oxopropylthio)propane-1,2-diyl diundecanoate. (12e); (2R)-3-((2S)-2-amino-3-((1-((2S,3S,4S)-3,4-dihydroxy-5-(hydroxymethyl)tetrahydrofuran-2-yl)-1H-1,2,3-triazol-4-yl)amino)-3-oxopropylthio)propane-1,2-diyl diundecanoate. (12f); (2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl diundecanoate. (12g); (2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl diundecanoate. (12h); (2R)-3-((2S)-2-amino-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl diundecanoate. (12i); (2R)-3-((2S)-2-amino-3-oxo-3-((1-((3,4,5,6-tetrahydroxytetrahydro-2H-pyran-2-yl)methyl)-1H-1,2,3-triazol-4-yl)amino)propylthio)propane-1,2-diyl diundecanoate. (12j); (2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl diundecanoate. (12k); (2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl diundecanoate. (12l); (R)-3-(S)-2-amino-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl diundecanoate. (12m); (R)-3-((S)-2-amino-3-((1-((R)-2,3-dihydroxypropyl)-1H-1,2,3-triazol-4-yl)amino)-3-oxopropylthio)propane-1,2-diyl didodecanoate. (13a); (2R)-3-((2S)-2-amino-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl didodecanoate. (13b); (2R)-3-((2S)-2-amino-3-((1-((2S)-2-hydroxy-2-(3S,4S)-3,4,5-trihydroxytetrahydrofuran-2-yl)ethyl)-1H-1,2,3-triazol-4-yl)amino)-3-oxopropylthio)propane-1,2-diyl didodecanoate. (13c); (R)-3-((S)-2-amino-3-oxo-3-((1-((2S,3S,4R,5R)-2,3,4,5,6-pentahydroxyhexyl)-1H-1,2,3-triazol-4-yl)amino)

propylthio)propane-1,2-diyl didodecanoate. (13d); (2R)-3-((2S)-2-amino-3-((1-((2S,3R,4S)-3,4-dihydroxy-5-(hydroxymethyl)tetrahydrofuran-2-yl)-1H-1,2,3-triazol-4-yl)amino)-3-oxopropylthio)propane-1,2-diyl didodecanoate. (13e); (2R)-3-((2S)-2-amino-3-((1-((2S,3S,4S)-3,4-dihydroxy-5-(hydroxymethyl)tetrahydrofuran-2-yl)-1H-1,2,3-triazol-4-yl)amino)-3-oxopropylthio)propane-1,2-diyl didodecanoate. (13f); (2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl didodecanoate. (13g); (2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl didodecanoate. (13h); (2R)-3-((2S)-2-amino-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl didodecanoate. (13i); (2R)-3-((2S)-2-amino-3-oxo-3-((1-((3,4,5,6-tetrahydroxytetrahydro-2H-pyran-2-yl)methyl)-1H-1,2,3-triazol-4-yl)amino)propylthio)propane-1,2-diyl didodecanoate. (13j); (2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl didodecanoate. (13k); (2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl didodecanoate. (13l); (R)-3-((S)-2-amino-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl didodecanoate. (13m); (R)-3-((S)-2-amino-3-((1-((R)-2,3-dihydroxypropyl)-1H-1,2,3-triazol-4-yl)amino)-3-oxopropylthio)propane-1,2-diyl ditridecanoate. (14a); (2R)-3-((2S)-2-amino-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl ditridecanoate. (14b); (2R)-3-((2S)-2-amino-3-((1-((2S)-2-hydroxy-2-((3S,4S)-3,4,5-trihydroxytetrahydro-furan-2-yl)ethyl)-1H-1,2,3-triazol-4-yl)amino)-3-oxopropylthio)propane-1,2-diyl ditridecanoate. (14c); (R)-3-((S)-2-amino-3-oxo-3-((1-((2S,3S,4R,5R)-2,3,4,5,6-pentahydroxyhexyl)-1H-1,2,3-triazol-4-yl)amino)propylthio)propane-1,2-diyl ditridecanoate. (14d); (2R)-3-((2S)-2-amino-3-((1-((2S,3R,4S)-3,4-dihydroxy-5-(hydroxymethyl)tetrahydrofuran-2-yl)-1H-1,2,3-triazol-4-yl)amino)-3-oxopropylthio)propane-1,2-diyl ditridecanoate. (14e); (2R)-3-((2S)-2-amino-3-((1-((2S,3S,4S)-3,4-dihydroxy-5-(hydroxymethyl)tetrahydrofuran-2-yl)-1H-1,2,3-triazol-4-yl)amino)-3-oxopropylthio)propane-1,2-diyl ditridecanoate. (14f); (2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl ditridecanoate. (14g); (2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl ditridecanoate. (14h); (2R)-3-((2S)-2-amino-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl ditridecanoate. (14i); (2R)-3-((2S)-2-amino-3-oxo-3-((1-((3,4,5,6-tetrahydroxytetrahydro-2H-pyran-2-yl)methyl)-1H-1,2,3-triazol-4-yl)amino)propylthio)propane-1,2-diyl ditridecanoate. (14j); (2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl ditridecanoate. (14k); (2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl ditridecanoate. (14l); (R)-3-((S)-2-amino-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl ditridecanoate. (14m); (R)-3-((S)-2-amino-3-((1-((R)-2,3-dihydroxypropyl)-1H-1,2,3-triazol-4-yl)amino)-3-oxopropylthio)propane-1,2-diyl ditetradecanoate. (15a); (2R)-3-((2S)-2-amino-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diylditetradecanoate. (15b); (2R)-3-((2S)-2-amino-3-((1-((2S)-2-hydroxy-2-((3S,4S)-3,4,5-trihydroxytetrahydrofuran-2-yl)ethyl)-1H-1,2,3-triazol-4-yl)amino)-3-oxopropylthio)propane-1,2-diyl ditetradecanoate. (15c); (R)-3-((S)-2-amino-3-oxo-3-((1-((2S,3S,4R,5R)-2,3,4,5,6-pentahydroxyhexyl)-1H-1,2,3-triazol-4-yl)amino)propylthio)propane-1,2-diyl ditetradecanoate. (15d); (2R)-3-((2S)-2-amino-3-((1-((2S,3R,4S)-3,4-dihydroxy-5-(hydroxymethyl)tetrahydrofuran-2-yl)-1H-1,2,3-triazol-4-yl)amino)-3-oxopropylthio)propane-1,2-diyl ditetradecanoate. (15e); (2R)-3-((2S)-2-amino-3-((1-((2S,3S,4S)-3,4-dihydroxy-5-(hydroxymethyl)tetrahydrofuran-2-yl)-1H-1,2,3-triazol-4-yl)amino)-3-oxopropylthio)propane-1,2-diyl ditetradecanoate. (15f); (2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diylditetradecanoate. (15g); (2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diylditetradecanoate. (15h); (2R)-3-((2S)-2-amino-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl ditetradecanoate. (15i); (2R)-3-((2S)-2-amino-3-oxo-3-((1-((3,4,5,6-tetrahydroxytetrahydro-2H-pyran-2-yl)methyl)-1H-1,2,3-triazol-4-yl)amino)propylthio)propane-1,2-diyl ditetradecanoate. (15j); (2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl ditetradecanoate. (15k); (2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl ditetradecanoate. (15l); (R)-3-((S)-2-amino-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl ditetradecanoate. (15m); (R)-3-((S)-2-amino-3-((1-((R)-2,3-dihydroxypropyl)-1H-1,2,3-triazol-4-yl)amino)-3-oxopropylthio)propane-1,2-diyl dipentadecanoate. (16a); (2R)-3-((2S)-2-amino-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl dipentadecanoate. (16b); (2R)-3-((2S)-2-amino-3-((1-((2S)-2-hydroxy-2-((3S,4S)-3,4,5-trihydroxytetrahydrofuran-2-yl)ethyl)-1H-1,2,3-triazol-4-yl)amino)-3-oxopropylthio)propane-1,2-diyl dipentadecanoate. (16c); (R)-3-((S)-2-amino-3-oxo-3-

((1-((2S,3S,4R,5R)-2,3,4,5,6-pentahydroxyhexyl)-1H-1,2,3-triazol-4-yl)amino)propylthio)propane-1,2-diyl dipentadecanoate. (16d); (2R)-3-((2S)-2-amino-3-((1-((2S,3R,4S)-3,4-dihydroxy-5-(hydroxymethyl)tetrahydrofuran-2-yl)-1H-1,2,3-triazol-4-yl)amino)-3-oxopropylthio)propane-1,2-diyl dipentadecanoate. (16e); (2R)-3-((2S)-2-amino-3-((1-((2S,3S,4S)-3,4-dihydroxy-5-(hydroxymethyl)tetrahydrofuran-2-yl)-1H-1,2,3-triazol-4-yl)amino)-3-oxopropylthio)propane-1,2-diyl dipentadecanoate. (16f); (2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dipentadecanoate. (16g); (2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dipentadecanoate. (16h); (2R)-3-((2S)-2-amino-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl dipentadecanoate. (16i); (2R)-3-((2S)-2-amino-3-oxo-3-((1-((3,4,5,6-tetrahydroxytetrahydro-2H-pyran-2-yl)methyl)-1H-1,2,3-triazol-4-yl)amino)propylthio)propane-1,2-diyl dipentadecanoate. (16j); (2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl dipentadecanoate. (16k); (2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl dipentadecanoate. (16l); (R)-3-((S)-2-amino-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl dipentadecanoate. (16m); (R)-3-((S)-2-amino-3-((1-((R)-2,3-dihydroxypropyl)-1H-1,2,3-triazol-4-yl)amino)-3-oxopropylthio)propane-1,2-diyl dipalmitate. (17a); (2R)-3-((2S)-2-amino-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl dipalmitate. (17b); (2R)-3-((2S)-2-amino-3-((1-((2S)-2-hydroxy-2-((3S,4S)-3,4,5-trihydroxytetrahydrofuran-2-yl)ethyl)-1H-1,2,3-triazol-4-yl)amino)-3-oxopropylthio)propane-1,2-diyl dipalmitate. (17c); (R)-3-((S)-2-amino-3-oxo-3-((1-((2S,3S,4R,5R)-2,3,4,5,6-pentahydroxyhexyl)-1H-1,2,3-triazol-4-yl)amino)propylthio)propane-1,2-diyl dipalmitate. (17d); (2R)-3-((2S)-2-amino-3-((1-((2S,3R,4S)-3,4-dihydroxy-5-(hydroxymethyl)tetrahydrofuran-2-yl)-1H-1,2,3-triazol-4-yl)amino)-3-oxopropylthio)propane-1,2-diyl dipalmitate. (17e); (2R)-3-((2S)-2-amino-3-((1-((2S,3S,4S)-3,4-dihydroxy-5-(hydroxymethyl)tetrahydrofuran-2-yl)-1H-1,2,3-triazol-4-yl)amino)-3-oxopropylthio)propane-1,2-diyl dipalmitate. (17f); (2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dipalmitate. (17g); (2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dipalmitate. (17h). (2R)-3-((2S)-2-amino-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl dipalmitate. (17i); (2R)-3-((2S)-2-amino-3-oxo-3-((1-((3,4,5,6-tetrahydroxytetrahydro-2H-pyran-2-yl)methyl)-1H-1,2,3-triazol-4-yl)amino)propylthio)propane-1,2-diyl dipalmitate. (17j); (2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl dipalmitate. (17k); (2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl dipalmitate. (17l); (R)-3-((S)-2-amino-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl dipalmitate. (17m); (R)-3-((S)-2-amino-3-((1-((R)-2,3-dihydroxypropyl)-1H-1,2,3-triazol-4-yl)amino)-3-oxopropylthio)propane-1,2-diyl diheptadecanoate. (18a); (2R)-3-((2S)-2-amino-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl diheptadecanoate. (18b); (2R)-3-((2S)-2-amino-3-((1-((2S)-2-hydroxy-2-((3S,4S)-3,4,5-trihydroxytetrahydrofuran-2-yl)ethyl)-1H-1,2,3-triazol-4-yl)amino)-3-oxopropylthio)propane-1,2-diyl diheptadecanoate. (18c); (R)-3-((S)-2-amino-3-oxo-3-((1-((2S,3S,4R,5R)-2,3,4,5,6-pentahydroxyhexyl)-1H-1,2,3-triazol-4-yl)amino)propylthio)propane-1,2-diyl diheptadecanoate. (18d); (2R)-3-((2S)-2-amino-3-((1-((2S,3R,4S)-3,4-dihydroxy-5-(hydroxymethyl)tetrahydrofuran-2-yl)-1H-1,2,3-triazol-4-yl)amino)-3-oxopropylthio)propane-1,2-diyl diheptadecanoate. (18e); (2R)-3-((2S)-2-amino-3-((1-((2S,3S,4S)-3,4-dihydroxy-5-(hydroxymethyl)tetrahydrofuran-2-yl)-1H-1,2,3-triazol-4-yl)amino)-3-oxopropylthio)propane-1,2-diyl diheptadecanoate. (18f); (2R)-3-((2S)-2-amino-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl diheptadecanoate. (18i); (2R)-3-((2S)-2-amino-3-oxo-3-((1-((3,4,5,6-tetrahydroxytetrahydro-2H-pyran-2-yl)methyl)-1H-1,2,3-triazol-4-yl)amino)propylthio)propane-1,2-diyl diheptadecanoate. (18j); (2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl diheptadecanoate. (18k); (2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl diheptadecanoate. (18l); (R)-3-((S)-2-amino-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl diheptadecanoate. (18m); (R)-3-((S)-2-amino-3-((1-((R)-2,3-dihydroxypropyl)-1H-1,2,3-triazol-4-yl)amino)-3-oxopropylthio)propane-1,2-diyl distearate. (19a); (2R)-3-((2S)-2-amino-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl distearate. (19b); (2R)-3-((2S)-2-amino-3-((1-((2S)-2-hydroxy-2-((3S,4S)-3,4,5-trihydroxytetrahydrofuran-2-yl)ethyl)-1H-1,2,3-triazol-4-yl)amino)-3-oxopropylthio)propane-1,2-diyl distearate. (19c); (R)-3-((S)-2-amino-3-oxo-3-((1-((2S,3S,4R,5R)-2,3,4,5,6-pentahydroxyhexyl)-1H-1,2,3-triazol-4-yl)amino)propylthio)propane-1,2-diyl distearate. (19d); (2R)-3-((2S)-2-amino-3-((1-((2S,3R,4S)-3,4-dihydroxy-5-(hydroxymethyl)tetrahydrofuran-2-yl)-1H-1,2,3-triazol-4-yl)amino)-3-oxopropylthio)propane-1,2-diyl distearate. (19e); (2R)-3-((2S)-2-amino-3-

((1-((2S,3S,4S)-3,4-dihydroxy-5-(hydroxymethyl) tetrahydrofuran-2-yl)-1H-1,2,3-triazol-4-yl)amino)-3-oxopropylthio)propane-1,2-diyl distearate. (19f); (2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl distearate. (19g); (2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl distearate. (19h). (2R)-3-(2S)-2-amino-3-oxo-3-((1-(3,4,5-trihydroxy-6-(hydroxymethyl) tetrahydro-2H-pyran-2-yl)-1H-1,2,3-triazol-4-yl)amino) propylthio)propane-1,2-diyl distearate. (19i). (2R)-3-((2S)-2-amino-3-oxo-3-((1-(3,4,5,6-tetrahydroxytetrahydro-2H-pyran-2-yl)methyl)-1H-1,2,3-triazol-4-yl)amino)propylthio)propane-1,2-diyl distearate. (19j); (2R)-3-((2S)-2-amino-3-oxo-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl distearate. (19k); (2R)-3-((2S)-2-amino-3-(1-((2R)-3,4-dihydroxy-6-(hydroxymethyl)-5-(3,4,5-trihydroxy-6-(hydroxymethyl) tetrahydro-2H-pyran-2-yloxy)tetrahydro-2H-pyran-2-yl)-1H-1,2,3-triazol-4-yl)amino)-3-oxopropylthio)propane-1,2-diyl distearate. (19l); (R)-3-((S)-2-amino-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl distearate. (19m); (2R)-3-((S)-3-((1-((R)-2,3-dihydroxypropyl)-1H-1,2,3-triazol-4-yl)amino)-2-hexanamido-3-oxopropylthio)propane-1,2-diyl dihexanoate. (20a); (2R)-3-((2S)-2-hexanamido-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl dihexanoate. (20b); (2R)-3-((2S)-2-hexanamido-3-((1-((2S)-2-hydroxy-2-((3S,4S)-3,4,5-trihydroxytetrahydrofuran-2-yl)ethyl)-1H-1,2,3-triazol-4-yl)amino)-3-oxopropylthio)propane-1,2-diyldihexanoate. (20c); (R)-3-((S)-2-hexanamido-3-oxo-3-((1-((2S,3S,4R,5R)-2,3,4,5,6-pentahydroxyhexyl)-1H-1,2,3-triazol-4-yl)amino)propylthio)propane-1,2-diyl dihexanoate. (20d); (2R)-3-((2S)-3-((1-((2S,3R,4S)-3,4-dihydroxy-5-(hydroxymethyl)tetrahydrofuran-2-yl)-1H-1,2,3-triazol-4-yl)amino)-2-hexanamido-3-oxopropylthio)propane-1,2-diyl dihexanoate. (20e); (2R)-3-((2S)-3-((1-((2S,3S,4S)-3,4-dihydroxy-5-(hydroxymethyl) tetrahydrofuran-2-yl)-1H-1,2,3-triazol-4-yl)amino)-2-hexanamido-3-oxopropylthio)propane-1,2-diyl dihexanoate. (20f); (2R)-3-((2S)-2-hexanamido-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyldihexanoate. (20g); (2R)-3-((2S)-2-hexanamido-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyldihexanoate. (20h); (2R)-3-((2S)-2-hexanamido-3-oxo-3-((1-(3,4,5-trihydroxy-6-(hydroxymethyl) tetrahydro-2H-pyran-2-yl)-1H-1,2,3-triazol-4-yl)amino) propylthio)propane-1,2-diyl dihexanoate. (20i); (2R)-3-((2S)-2-hexanamido-3-oxo-3-((1-(3,4,5,6-tetrahydroxytetrahydro-2H-pyran-2-yl)methyl)-1H-1,2,3-triazol-4-yl)amino)propylthio)propane-1,2-diyl dihexanoate. (20j); (2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-2-hexanamido-3-oxopropylthio)propane-1,2-diyl dihexanoate. (20k); (2R)-3-(2S)-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-2-hexanamido-3-oxopropylthio)propane-1,2-diyl dihexanoate. (20l); (R)-3-((S)-2-hexanamido-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl dihexanoate. (20m); (R)-3-((S)-3-((1-((R)-2,3-dihydroxypropyl)-1H-1,2,3-triazol-4-yl)amino)-2-heptanamido-3-oxopropylthio)propane-1,2-diyl diheptanoate. (21a); (2R)-3-((2S)-2-heptanamido-3-oxo-3-((2S)-3,4,5-trihydroxy-6-hydroxymethyl)tetrahydro-2H-pyran-2-yl)-1H-1,2,3-triazol-4-yl)amino)propylthio) propane-1,2-diyl diheptanoate. (21b); (2R)-3-((2S)-2-heptanamido-3-((1-((2S)-2-hydroxy-2-((3S,4S)-3,4,5-trihydroxytetrahydrofuran-2-yl)ethyl)-1H-1,2,3-triazol-4-yl)amino)-3-oxopropylthio)propane-1,2-diyl diheptanoate. (21c); (R)-3-((S)-2-heptanamido-3-oxo-3-((1-(2S,3S,4R,5R)-2,3,4,5,6-pentahydroxyhexyl)-1H-1,2,3-triazol-4-yl)amino)propylthio)propane-1,2-diyl diheptanoate. (21d); (2R)-3-((2S)-3-((1-((2S,3R,4S)-3,4-dihydroxy-5-(hydroxymethyl)tetrahydrofuran-2-yl)-1H-1,2,3-triazol-4-yl)amino)-2-heptanamido-3-oxopropylthio)propane-1,2-diyl diheptanoate. (21e); (2R)-3-((2S)-3-((1-((2S,3S,4S)-3,4-dihydroxy-5-(hydroxymethyl)tetrahydrofuran-2-yl)-1H-1,2,3-triazol-4-yl) amino)-2-heptanamido-3-oxopropylthio)propane-1,2-diyl diheptanoate. (21f); (2R)-3-((2S)-2-heptanamido-3-oxo-3-((1-((2R)-3,4,5-trihydroxy-6-(hydroxymethyl) tetrahydro-2H-pyran-2-yl)-1H-1,2,3-triazol-4-yl)amino) propylthio)propane-1,2-diyl diheptanoate. (21g); (2R)-3-(2S)-2-heptanamido-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl diheptanoate. (21h); (2R)-3-(2S)-2-heptanamido-3-oxo-3-((1-(3,4,5-trihydroxy-6-(hydroxymethyl)tetrahydro-2H-pyran-2-yl)-1H-1,2,3-triazol-4-yl)amino)propylthio) propane-1,2-diyl diheptanoate. (21i); (2R)-3-((2S)-2-heptanamido-3-oxo-3-((1-((3,4,5,6-tetrahydroxytetrahydro-2H-pyran-2-yl)methyl)-1H-1,2,3-triazol-4-yl)amino)propylthio)propane-1,2-diyl diheptanoate. (21j); (2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-2-heptanamido-3-oxopropylthio)propane-1,2-diyl diheptanoate. (21k); (2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-2-heptanamido-3-oxopropylthio)propane-1,2-diyl diheptanoate. (21l); (R)-3-((S)-2-heptanamido-3-oxo-3-((1-((1S,2S,3R,4S,5S,6S)-2,3,4,5,6-pentahydroxycyclohexyl)-1H-1,2,3-triazol-4-yl)amino)propane-1,2-diyl diheptanoate. (21m); (R)-3-((S)-3-((1-((R)-2,3-dihydroxypropyl)-1H-1,2,3-triazol-4-yl)amino)-2-octanamido-3-oxopropylthio)propane-1,2-diyl dioctanoate. (22a); (2R)-3-((2S)-2-octanamido-3-oxo-3-((1-((2S)-3,4,5-trihydroxy-6-(hydroxymethyl)tetrahydro-2H-pyran-2-yl)-1H-1,2,3-triazol-4-yl)amino)propylthio) propane-1,2-diyl dioctanoate. (22b); (2R)-3-((2S)-3-((1-((2S)-2-hydroxy-2-((3S,4S)-3,4,5-trihydroxytetrahydrofuran-2-yl)ethyl)-1H-1,2,3-triazol-4-yl)amino)-2-octanamido-3-oxopropylthio)propane-1,2-diyl dioctanoate. (22c); (R)-3-((S)-2-octanamido-3-oxo-3-((1-((2S,3S,4R,5R)-2,3,4,5,6-pentahydroxyhexyl)-1H-

1,2,3-triazol-4-yl)amino)propylthio)propane-1,2-diyl dioctanoate. (22d) (2R)-3-((2S)-3-((1-((2S,3R,4S)-3,4-dihydroxy-5-(hydroxymethyl)tetrahydrofuran-2-yl)-1H-1,2,3-triazol-4-yl)amino)-2-octanamido-3-oxopropylthio)propane-1,2-diyl dioctanoate. (22e); (2R)-3-((2S)-3-((1-((2S,3S,4S)-3,4-dihydroxy-5-(hydroxymethyl)tetrahydrofuran-2-yl)-1H-1,2,3-triazol-4-yl)amino)-2-octanamido-3-oxopropylthio)propane-1,2-diyl dioctanoate. (22f); (2R)-3-((2S)-2-octanamido-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dioctanoate. (22g); (2R)-3-((2S)-2-octanamido-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dioctanoate. (22h); (2R)-3-((2S)-2-octanamido-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl dioctanoate. (22i); (2R)-3-((2S)-2-octanamido-3-oxo-3-((1-((3,4,5,6-tetrahydroxytetrahydro-2H-pyran-2-yl)methyl)-1H-1,2,3-triazol-4-yl)amino)propylthio)propane-1,2-diyl dioctanoate. (22j); (2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-2-octanamido-3-oxopropylthio)propane-1,2-diyl dioctanoate. (22k); (2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-2-octanamido-3-oxopropylthio)propane-1,2-diyl dioctanoate. (22l); (R)-3-((S)-2-octanamido-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl dioctanoate. (22m); (R)-3-((S)-3-((1-((R)-2,3-dihydroxypropyl)-1H-1,2,3-triazol-4-yl)amino)-2-nonanamido-3-oxopropylthio)propane-1,2-diyl dinonanoate. (23a); 2R)-3-((2S)-2-nonanamido-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl dinonanoate. (23b); (2R)-3-((2S)-3-((1-((2S)-2-hydroxy-2-((3S,4S)-3,4,5-trihydroxytetrahydrofuran-2-yl)ethyl)-1H-1,2,3-triazol-4-yl)amino)-2-nonanamido-3-oxopropylthio)propane-1,2-diyl dinonanoate. (23c); (R)-3-((S)-2-nonanamido-3-oxo-3-((1-((2S,3S,4R,5R)-2,3,4,5,6-pentahydroxyhexyl)-1H-1,2,3-triazol-4-yl)amino)propylthio)propane-1,2-diyl dinonanoate. (23d); (2R)-3-((2S)-3-((1-((2S,3R,4S)-3,4-dihydroxy-5-(hydroxymethyl)tetrahydrofuran-2-yl)-1H-1,2,3-triazol-4-yl)amino)-2-nonanamido-3-oxopropylthio)propane-1,2-diyl dinonanoate. (23e); (2R)-3-((2S)-3-((1-((2S,3S,4S)-3,4-dihydroxy-5-(hydroxymethyl)tetrahydrofuran-2-yl)-1H-1,2,3-triazol-4-yl)amino)-2-nonanamido-3-oxopropylthio)propane-1,2-diyl dinonanoate. (23f); (2R)-3-((2S)-2-nonanamido-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dinonanoate. (23g.); (2R)-3-((2S)-2-nonanamido-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dinonanoate. (23h); (2R)-3-((2S)-2-nonanamido-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl dinonanoate. (23i); (2R)-3-((2S)-2-nonanamido-3-oxo-3-((1-((3,4,5,6-tetrahydroxytetrahydro-2H-pyran-2-yl)methyl)-1H-1,2,3-triazol-4-yl)amino)propylthio)propane-1,2-diyl dinonanoate. (23j); (2R)-3-(2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-2-nonanamido-3-oxopropylthio)propane-1,2-diyl dinonanoate. (23k); (2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-2-nonanamido-3-oxopropylthio)propane-1,2-diyl dinonanoate. (23l); (R)-3-((S)-2-nonanamido-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl dinonanoate. (23m); (R)-3-((S)-2-decanamido-3-((1-((R)-2,3-dihydroxypropyl)-1H-1,2,3-triazol-4-yl)amino)-3-oxopropylthio)propane-1,2-diyl bis(decanoate). (24a); (2R)-3-((2S)-2-decanamido-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl bis(decanoate) (24b); (2R)-3-((2S)-2-decanamido-3-((1-((2S)-2-hydroxy-2-((3S,4S)-3,4,5-trihydroxytetrahydrofuran-2-yl)ethyl)-1H-1,2,3-triazol-4-yl)amino)-3-oxopropylthio)propane-1,2-diyl bis(decanoate) (24c); (R)-3-((S)-2-decanamido-3-oxo-3-((1-((2S,3S,4R,5R)-2,3,4,5,6-pentahydroxyhexyl)-1H-1,2,3-triazol-4-yl)amino)propylthio)propane-1,2-diyl bis(decanoate) (24d); (2R)-3-((2S)-2-decanamido-3-((1-((2S,3R,4S)-3,4-dihydroxy-5-(hydroxymethyl)tetrahydrofuran-2-yl)-1H-1,2,3-triazol-4-yl)amino)-3-oxopropylthio)propane-1,2-diyl bis(decanoate) (24e); (2R)-3-((2S)-2-decanamido-3-((1-((2S,3S,4S)-3,4-dihydroxy-5-(hydroxymethyl)tetrahydrofuran-2-yl)-1H-1,2,3-triazol-4-yl)amino)-3-oxopropylthio)propane-1,2-diyl bis(decanoate) (24f); (2R)-3-((2S)-2-decanamido-3-oxo-3-((1-(2R)-3,4,5-trihydroxy-6-(hydroxymethyl)tetrahydro-2H-pyran-2-yl)-1H-1,2,3-triazol-4-yl)amino)propylthio)propane-1,2-diyl bis(decanoate). (24g); (2R)-3-((2S)-2-decanamido-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl bis(decanoate) (24h); (2R)-3-((2S)-2-decanamido-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl bis(decanoate) (24i); (2R)-3-((2S)-2-decanamido-3-oxo-3-((1-((3,4,5,6-tetrahydroxytetrahydro-2H-pyran-2-yl)methyl)-1H-1,2,3-triazol-4-yl)amino)propylthio)propane-1,2-diyl bis(decanoate) (24j); (2R)-3-((2S)-2-decanamido-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl bis(decanoate). (24k); (2R)-3-((2S)-2-decanamido-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl bis(decanoate) (24l); (R)-3-((S)-2-decanamido-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl bis(decanoate) (24m); (R)-3-((S)-3-((1-((R)-2,3-dihydroxypropyl)-1H-1,2,3-triazol-4-yl)amino)-3-oxo-2-undecanamidopropylthio)propane-1,2-diyl diundecanoate (25a); (2R)-3-((2S)-3-oxo-3-((1-((2S)-3,4,5-trihydroxy-6-(hydroxymethyl)tetrahydro-2H-pyran-2-yl)-1H-1,2,3-triazol-4-yl)amino)-

2-undecanamidopropylthio)propane-1,2-diyl diundecanoate (25b); (2R)-3-((2S)-3-((1-((2S)-2-hydroxy-2-((3S,4S)-3,4,5-trihydroxytetrahydrofuran-2-yl)ethyl)-1H-1,2,3-triazol-4-yl)amino)-3-oxo-2-undecanamidopropylthio)propane-1,2-diyl diundecanoate (25c); (R)-3-((S)-3-oxo-3-((1-((2S,3S,4R,5R)-2,3,4,5,6-pentahydroxyhexyl)-1H-1,2,3-triazol-4-yl)amino)-2-undecanamido-propylthio)propane-1,2-diyl diundecanoate (25d); (2R)-3-((2S)-3-((1-((2S,3R,4S)-3,4-dihydroxy-5-(hydroxymethyl)tetrahydrofuran-2-yl)-1H-1,2,3-triazol-4-yl)amino)-3-oxo-2-undecanamido-propylthio)propane-1,2-diyl diundecanoate (25e); (2R)-3-((2S)-3-((1-((2S,3S,4S)-3,4-dihydroxy-5-(hydroxymethyl)tetrahydrofuran-2-yl)-1H-1,2,3-triazol-4-yl)amino)-3-oxo-2-undecanamidopropylthio)propane-1,2-diyl diundecanoate (25f). (2R)-3-((2S)-3-oxo-3-((1-((2R)-3,4,5-trihydroxy-6-(hydroxymethyl)tetrahydro-2H-pyran-2-yl)-1H-1,2,3-triazol-4-yl)methylamino)-2-undecanamidopropylthio)propane-1,2-diyl diundecanoate (25g): (2R)-3-((2S)-3-oxo-3-((1-((2R)-3,4,5-trihydroxy-6-(hydroxymethyl)tetrahydro-2H-pyran-2-yl)-1H-1,2,3-triazol-4-yl)amino)-2-undecanamidopropylthio)propane-1,2-diyl diundecanoate (25h); (2R)-3-((2S)-3-oxo-3-((1-(3,4,5-trihydroxy-6-(hydroxymethyl)tetrahydro-2H-pyran-2-yl)-1H-1,2,3-triazol-4-yl)amino)-2-undecanamidopropylthio)propane-1,2-diyl diundecanoate (25i); (2R)-3-((2S)-3-oxo-3-((1-((3,4,5,6-tetrahydroxytetrahydro-2H-pyran-2-yl)methyl)-1H-1,2,3-triazol-4-yl)amino)-2-undecanamido-propylthio)propane-1,2-diyl diundecanoate (25j); (2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxo-2-undecanamidopropylthio)propane-1,2-diyl diundecanoate (25k); (2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxo-2-undecanamidopropylthio)propane-1,2-diyl diundecanoate (25l); (R)-3-((S)-3-oxo-3-((1-((1S,2S,3R,4S,5S,6S)-2,3,4,5,6-pentahydroxycyclohexyl)-1H-1,2,3-triazol-4-yl)amino)-2-undecanamidopropylthio)propane-1,2-diyl diundecanoate (25m); (R)-3-((S)-3-((1-((R)-2,3-dihydroxypropyl)-1H-1,2,3-triazol-4-yl)amino)-2-dodecanamido-3-oxopropylthio)propane-1,2-diyl didodecanoate (26a); (2R)-3-((2S)-2-dodecanamido-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl didodecanoate (26b); (2R)-3-((2S)-2-dodecanamido-3-((1-(2S)-2-hydroxy-2-((3S,4S)-3,4,5-trihydroxytetrahydrofuran-2-yl)ethyl)-1H-1,2,3-triazol-4-yl)amino)-3-oxopropylthio)propane-1,2-diyl didodecanoate (26c); (R)-3-((S)-2-dodecanamido-3-oxo-3-((1-((2S,3S,4R,5R)-2,3,4,5,6-pentahydroxyhexyl)-1H-1,2,3-triazol-4-yl)amino)propylthio)propane-1,2-diyl didodecanoate (26d); (2R)-3-((2S)-3-((1-((2S,3R,4S)-3,4-dihydroxy-5-(hydroxymethyl)tetrahydrofuran-2-yl)-1H-1,2,3-triazol-4-yl)amino)-2-dodecanamido-3-oxopropylthio)propane-1,2-diyl didodecanoate (26e); (2R)-3-((2S)-3-((1-((2S,3S,4S)-3,4-dihydroxy-5-(hydroxymethyl)tetrahydrofuran-2-yl)-1H-1,2,3-triazol-4-yl)amino)-2-dodecanamido-3-oxopropylthio)propane-1,2-diyl didodecanoate (26f); (2R)-3-((2S)-2-dodecanamido-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl didodecanoate (26g); (2R)-3-((2S)-2-dodecanamido-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl didodecanoate (26h); (2R)-3-((2S)-2-dodecanamido-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl didodecanoate (26i); (2R)-3-((2S)-2-dodecanamido-3-oxo-3-((1-((3,4,5,6-tetrahydroxy-tetrahydro-2H-pyran-2-yl)methyl)-1H-1,2,3-triazol-4-yl)amino)propylthio)propane-1,2-diyl didodecanoate (26j); (2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-2-dodecanamido-3-oxopropylthio)propane-1,2-diyl didodecanoate (26k); (2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-2-dodecanamido-3-oxopropylthio)propane-1,2-diyl didodecanoate (26l); (R)-3-((S)-2-dodecanamido-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl didodecanoate (26m); (R)-3-((S)-3-((1-((R)-2,3-dihydroxypropyl)-1H-1,2,3-triazol-4-yl)amino)-3-oxo-2-tridecanamidopropylthio)propane-1,2-diyl ditridecanoate (27a); (2R)-3-((2S)-3-oxo-2-tridecanamido-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl ditridecanoate (27b); (2R)-3-((2S)-3-((1-((2S)-2-hydroxy-2-((3S,4S)-3,4,5-trihydroxytetrahydrofuran-2-yl)ethyl)-1H-1,2,3-triazol-4-yl)amino)-3-oxo-2-tridecanamidopropylthio)propane-1,2-diyl ditridecanoate (27c); (R)-3-((S)-3-oxo-3-((1-((2S,3S,4R,5R)-2,3,4,5,6-pentahydroxyhexyl)-1H-1,2,3-triazol-4-yl)amino)-2-tridecanamidopropylthio)propane-1,2-diyl ditridecanoate (27d); (2R)-3-((2S)-3-((1-((2S,3R,4S)-3,4-dihydroxy-5-(hydroxymethyl)tetrahydrofuran-2-yl)-1H-1,2,3-triazol-4-yl)amino)-3-oxo-2-tridecanamidopropylthio)propane-1,2-diyl ditridecanoate (27e); (2R)-3-((2S)-3-((1-((2S,3S,4S)-3,4-dihydroxy-5-(hydroxymethyl)tetrahydrofuran-2-yl)-1H-1,2,3-triazol-4-yl)amino)-3-oxo-2-tridecanamido-propylthio)propane-1,2-diyl ditridecanoate (27f). (2R)-3-((2S)-3-oxo-2-tridecanamido-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl ditridecanoate (27g); (2R)-3-((2S)-3-oxo-2-tridecanamido-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl ditridecanoate (27h); (2R)-3-((2S)-3-oxo-2-tridecanamido-3-((1-(3,4,5-trihydroxy-6-(hydroxymethyl)tetrahydro-2H-pyran-2-yl)-1H-1,2,3-triazol-4-yl)amino)propylthio)propane-1,2-diyl ditridecanoate (27i); (2R)-3-((2S)-3-oxo-3-((1-((3,4,5,6-tetrahydroxytetrahydro-2H-pyran-2-yl)methyl)-1H-1,2,3-triazol-4-yl)amino)-2-tridecanamidopropylthio)propane-1,2-diyl ditridecanoate (27j); (2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxo-2-tridecanamidopropylthio)propane-1,2-diyl ditridecanoate (27k); (2R)-3-((2S)-3-((1-(2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxo-2-tridecanamidopropylthio)propane-1,2-diyl ditridecanoate (27l); (R)-3-((S)-3-oxo-3-((1-((1S,2S,3R,4S,5S,6S)-2,3, 4,5,6-pentahydroxycyclohexyl)-1H-1,2,3-triazol-4-yl) amino)-2-tridecanamidopropylthio)propane-1,2-diyl ditridecanoate (27m); (R)-3-((S)-3-((1-((R)-2,3-dihydroxypropyl)-1H-1,2,3-triazol-4-yl)amino)-3-oxo-2-tetradecanamidopropylthio)propane-1,2-diyl ditetradecanoate (28a); (2R)-3-((2S)-3-oxo-2-tetradecanamido-3-((1-((2S)-3,4,5-trihydroxy-6(hydroxymethyl)tetrahydro-2H-pyran-2-yl)-1H-1,2,3-triazol-4-yl)amino)propylthio) propane-1,2-diyl ditetradecanoate (28b); (2R)-3-((2S)-3-((1-((2S)-2-hydroxy-2-((3S,4S)-3,4,5-trihydroxytetrahydrofuran-2-yl)ethyl)-1H-1,2,3-triazol-4-yl)amino)-3-oxo-2-tetradecanamidopropylthio)propane-1,2-diyl ditetradecanoate (28c); (R)-3-((S)-3-oxo-3-((1-((2S,3S,4R,5R)-2,3,4,5,6-pentahydroxyhexyl)-1H-1,2,3-triazol-4-yl)amino)-2-tetradecanamidopropylthio)propane-1,2-diyl ditetradecanoate (28d); (2R)-3-((2S)-3-((1-((2S,3R,4S)-3,4-dihydroxy-5-(hydroxymethyl)tetrahydrofuran-2-yl)-1H-1,2,3-triazol-4-yl)amino)-3-oxo-2-tetradecanamidopropylthio)propane-1,2-diyl ditetradecanoate (28e); (2R)-3-((2S)-3-((1-((2S,3S,4S)-3,4-dihydroxy-5-(hydroxymethyl)tetrahydrofuran-2-yl)-1H-1,2,3-triazol-4-yl)amino)-3-oxo-2-tetradecanamidopropylthio)propane-1,2-diyl ditetradecanoate (28f); (2R)-3-((2S)-3-oxo-2-tetradecanamido-3-((1-((2R)-3,4,5-trihydroxy-6(hydroxymethyl)tetrahydro-2H-pyran-2-yl)-1H-1,2,3-triazol-4-yl)amino)propylthio)propane-1,2-diyl ditetradecanoate (28g); (2R)-3-(2S)-3-oxo-2-tetradecanamido-3-((1-((2R)-3,4,5-trihydroxy-6(hydroxymethyl)tetrahydro-2H-pyran-2-yl)-1H-1,2,3-triazol-4-yl)amino) propylthio)propane-1,2-diyl ditetradecanoate (28h); (R)-3-((S)-3-((1-((R)-2,3-dihydroxypropyl)-1H-1,2,3-triazol-4-yl)amino)-3-oxo-2-pentadecanamido-propylthio) propane-1,2-diyl dipentadecanoate (29a); (2R)-3-((2S)-3-oxo-2-pentadecanamido-3-((1-((2S)-3,4,5-trihydroxy-(hydroxymethyl)tetrahydro-2H-pyran-2-yl)-1H-1,2,3-triazol-4-yl)amino)propylthio)propane-1,2-diyldipentadecanoate (29b); (2R)-3-((2S)-3-((1-((2S)-2-hydroxy-2-((3S,4S)-3,4,5-trihydroxytetrahydrofuran-2-yl)ethyl)-1H-1,2,3-triazol-4-yl)amino)-3-oxo-2-pentadecanamido-propylthio)propane-1,2-diyl dipentadecanoate (29c); (R)-3-((S)-3-oxo-2-pentadecanamido-3-((1-((2S,3S,4R,5R)-2,3,4,5,6-pentahydroxyhexyl)-1H-1,2,3-triazol-4-yl)amino)propylthio)propane-1,2-diyl dipentadecanoate (29d); (2R)-3-((2S)-3-((1-((2S,3R,4S)-3,4-dihydroxy-5-(hydroxymethyl) tetrahydrofuran-2-yl)-1H-1,2,3-triazol-4-yl)amino)-3-oxo-2-pentadecanamido-propylthio)propane-1,2-diyl dipentadecanoate (29e); (2R)-3-((2S)-3-((1-((2S,3S,4S)-3,4-dihydroxy-5-(hydroxymethyl)tetrahydrofuran-2-yl)-1H-1,2,3-triazol-4-yl)amino)-3-oxo-2-pentadecanamido-propylthio)propane-1,2-diyl dipentadecanoate (29f); (2R)-3-((2S)-3-oxo-2-pentadecanamido-3-((1-((2R)-3,4,5-trihydroxy-(hydroxymethyl)tetrahydro-2H-pyran-2-yl)-1H-1,2,3-triazol-4-yl)amino)propylthio)propane-1,2-diyl dipentadecanoate (29g); (2R)-3-((2S)-3-oxo-2-pentadecanamido-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dipentadecanoate (29h); (2R)-3-((2S)-3-oxo-2-pentadecanamido-3-((1-(3,4,5-trihydroxy-6-(hydroxymethyl)tetrahydro-2H-pyran-2-yl)-1H-1,2,3-triazol-4-yl)amino) propylthio)propane-1,2-diyl dipentadecanoate (29i); (2R)-3-((2S)-3-oxo-2-pentadecanamido-3-((1-((3,4,5,6-tetrahydroxytetrahydro-2H-pyran-2-yl)methyl)-1H-1,2,3-triazol-4-yl)amino)propylthio)propane-1,2-diyl dipentadecanoate (29j); (2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxo-2-pentadecanamidopropylthio)propane-1,2-diyl dipentadecanoate (29k); (2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxo-2-pentadecanamido-propylthio)propane-1,2-diyl dipentadecanoate (29l); (R)-3-((S)-3-oxo-2-pentadecanamido-3-((1-((1S,2S,3R,4S,5S,6S)-2,3,4,5,6-pentahydroxycyclohexyl)-1H-1,2,3-triazol-4-yl)amino)propylthio)propane-1,2-diyl dipentadecanoate (29m); (R)-3-((S)-3-((1-((R)-2,3-dihydroxypropyl)-1H-1,2,3-triazol-4-yl)amino)-3-oxo-2-palmitamidopropylthio)propane-1,2-diyl dipalmitate (30a); (2R)-3-((2S)-3-oxo-2-palmitamido-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl dipalmitate (30b); (2R)-3-((2S)-3-((1-((2S)-2-hydroxy-2-((3S,4S)-3,4,5-trihydroxytetrahydrofuran-2-yl)ethyl)-1H-1,2,3-triazol-4-yl)amino)-3-oxo-2-palmitamidopropylthio)propane-1,2-diyl dipalmitate (30c); (R)-3-((S)-3-oxo-2-palmitamido-3-((1-((2S,3S,4R,5R)-2,3,4,5,6-pentahydroxyhexyl)-1H-1,2,3-triazol-4-yl)amino) propylthio)propane-1,2-diyl dipalmitate (30d); (2R)-3-((2S)-3-((1-((2S,3R,4S)-3,4-dihydroxy-5-(hydroxymethyl)tetrahydrofuran-2-yl)-1H-1,2,3-triazol-4-yl)amino)-3-oxo-2-palmitamidopropylthio)propane-1,2-diyl dipalmitate (30e); (2R)-3-((2S)-3-((1-((2S,3S,4S)-3,4-dihydroxy-5-(hydroxymethyl)tetrahydrofuran-2-yl)-1H-1,2,3-triazol-4-yl)amino)-3-oxo-2-palmitamidopropylthio)propane-1,2-diyl dipalmitate (30f); (2R)-3-((2S)-3-oxo-2-palmitamido-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dipalmitate (30g); (2R)-3-((2S)-3-oxo-2-palmitamido-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dipalmitate (30h); (2R)-3-((2S)-3-oxo-2-pamlitamido-3-((1-(3,4,5-trihydroxy-6-(hydroxymethyl)tetrahydro-2H-pyran-2-yl)-1H-1,2,3-triazol-4-yl)amino)propylthio)propane-1,2-diyl dipalmitate (30i); (2R)-3-((2S)-3-oxo-2-palmitamido-3-((1-((3,4,5,6-tetrahydroxytetrahydro-2H-pyran-2-yl)methyl)-1H-1,2,3-triazol-4-yl)amino) propylthio)propane-1,2-diyl dipalmitate (30j); (2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxo-2-palmitamidopropylthio) propane-1,2-diyl dipalmitate (30k); (2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl) amino)-3-oxo-2-palmitamido-propylthio)propane-1,2-diyl dipalmitate (30l); (R)-3-((S)-3-oxo-2-palmitamido-3-((1-((1S,2S,3R,4S,5S,6S)-2,3,4,5,6-pentahydroxycyclohexyl)-1H-1,2,3-triazol-4-yl)amino) propylthio)propane-1,2-diyl dipalmitate (30m); (R)-3-((S)-3-((1-((R)-2,3-dihydroxypropyl)-1H-1,2,3-triazol-4-yl)amino)-2-heptadecanamido-3-oxopropylthio)propane-1,2-diyl diheptadecanoate (31a); (2R)-3-(2S)-2-heptadecanamido-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl diheptadecanoate (31b); (2R)-3-((2S)-2-heptadecanamido-3-((1-((2S)-2-hydroxy-2-((3S,4S)-3,4,5-trihydroxytetrahydrofuran-2-yl)ethyl)-1H-1,2,3-triazol-4-yl)amino)-3-oxopropylthio)propane-1,2-diyl diheptadecanoate (31c); (R)-3-((S)-2-heptadecanamido-3-oxo-3-((1-((2S,3S,4R,5R)-2,3,4,5,6-pentahydroxyhexyl)-1H-1,2,3-triazol-4-yl)amino)propylthio)propane-1,2-diyl diheptadecanoate (31d); (2R)-3-((2S)-3-((1-((2S,3R,4S)-3,4-dihydroxy-5-(hydroxymethyl)tetrahydrofuran-2-yl)-1H-1,2,3-triazol-4-yl)amino)-2-heptadecanamido-3-oxopropylthio)propane-1,2-diyl diheptadecanoate (31e); (2R)-3-((2S)-3-((1-((2S,3S,4S)-3,4-dihydroxy-5-(hydroxymethyl)tetrahydrofuran-2-yl)-1H-1,2,3-triazol-4-yl)amino)-2-heptadecanamido-3-oxopropylthio)propane-1,2-diyl diheptadecanoate (31f); (2R)-3-((2S)-2-heptadecanamido-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl diheptadecanoate (31g); (2R)-3-((2S)-2-heptadecanamido-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl diheptadecanoate (31h); (2R)-3-((2S)-2-heptadecanamido-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl diheptadecanoate (31i); (2R)-3-((2S)-2-heptadecanamido-3-oxo-3-((1-((3,4,5,6-tetrahydroxytetrahydro-2H-pyran-2-yl)methyl)-1H-1,2,3-triazol-4-yl)amino)propylthio)propane-1,2-diyl diheptadecanoate (31j); (2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-2-heptadecanamido-3-oxopropylthio)propane-1,2-diyl diheptadecanoate (31k); (2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-2-heptadecanamido-3-oxopropylthio)propane-1,2-diyl diheptadecanoate (31l); (R)-3-((S)-2-heptadecanamido-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl diheptadecanoate (31m); (R)-3-((S)-3-((1-((R)-2,3-dihydroxypropyl)-1H-1,2,3-triazol-4-yl)amino)-3-oxo-2-stearamidopropylthio)propane-1,2-diyl distearate (32a); (2R)-3-((2S)-3-oxo-2-stearamido-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl distearate (32b); (2R)-3-((2S)-3-((1-((2S)-2-hydroxy-2-((3S,4S)-3,4,5-trihydroxytetrahydrofuran-2-yl)ethyl)-1H-1,2,3-triazol-4-yl)amino)-3-oxo-2-stearamidopropylthio)propane-1,2-diyl distearate (32c); (R)-3-((S)-3-oxo-3-((1-((2S,3S,4R,5R)-2,3,4,5,6-pentahydroxyhexyl)-1H-1,2,3-triazol-4-yl)amino)-2-stearamidopropylthio)propane-1,2-diyl distearate (32d); (2R)-3-((2S)-3-((1-((2S,3R,4S)-3,4-dihydroxy-5-(hydroxymethyl)tetrahydrofuran-2-yl)-1H-1,2,3-triazol-4-yl)amino)-3-oxo-2-stearamidopropylthio)propane-1,2-diyl distearate (32e); (2R)-3-((2S)-3-((1-((2S,3S,4S)-3,4-dihydroxy-5-(hydroxymethyl)tetrahydrofuran-2-yl)-1H-1,2,3-triazol-4-yl)amino)-3-oxo-2-stearamidopropylthio)propane-1,2-diyl distearate (32f); (2R)-3-((2S)-3-oxo-2-stearamido-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl distearate (32g); (2R)-3-((2S)-3-oxo-2-stearamido-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl distearate (32h); (2R)-3-((2S)-3-oxo-2-stearamido-3-((1-(3,4,5-trihydroxy-6-(hydroxymethyl)tetrahydro-2H-pyran-2-yl)-1H-1,2,3-triazol-4-yl)amino)propylthio)propane-1,2-diyl distearate (32i); (2R)-3-((2S)-3-oxo-2-stearamido-3-((1-((3,4,5,6-tetrahydroxytetrahydro-2H-pyran-2-yl)methyl)-1H-1,2,3-triazol-4-yl)amino)propylthio)propane-1,2-diyl distearate (32j); (2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxo-2-stearamidopropylthio)propane-1,2-diyl distearate (32k); (2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxo-2-stearamidopropylthio)propane-1,2-diyl distearate (32l); (R)-3-((S)-3-oxo-3-((1-((1S,2S,3R,4S,5S,6S)-2,3,4,5,6-pentahydroxycyclohexyl)-1H-1,2,3-triazol-4-yl)amino)-2-stearamidopropylthio)propane-1,2-diyl distearate (32m).

In another embodiment of present invention. R may be selected from hydroxyl-cycloalkane like Inositols in all their steroisomeric forms.

In still another embodiment, present invention provides a process for preparation of vaccine adjuvant conjugate of formula 1, wherein the said process comprises the steps of:
i) condensing N-(tert-Butoxycarbonyl)-L-cysteine methylester and Iodo compound (4) in presence of an organic base in dry DMF followed by hydrolysis to obtain an acid intermediate (5)and condensing with phenacyl bromide to obtain compound (6);
ii) treating compound (6)as obtained in step (i) with acetic acid and lipidation using carboxylic acid in presence of a suitable carbodiimide compound along with an organic base in a solvent to obtain dilipidated compound (8);
iii) treating compound (8)as obtained in step (ii) with TFA in a suitable solvent and subsequent reaction of the resulting amine with a suitable long chain carboxylic acid in the presence of a carbodiimide compound in an appropriate solvent to afford trilipidated compound (9);
iv) treating compound (9)as obtained in step (iii) with Zn in AcOH followed by coupling of the resulting carboxylic acid with propargyl amine using a carbodiimide compound and an activating base to obtain trilipidated alkyne compound (11);
v) treating compound (11)as obtained in step (iv) with carbohydrate and polyhydroxy alkyl azide (12) in presence of sodium ascorbate in t-BuOH/water system by copper(I) catalyzed click chemistry protocol to obtain vaccine adjuvant conjugate of formula 1.

In still another embodiment of present invention, the organic base used in step (ii) is DMAP and the carbodiimide compound used in step (ii), step (iii)and step (iv)are selected from like DCC, EDCI or DIC.

In still another embodiment of present invention, the azide, alkyne triazolyl click chemistry may or may not use copper as catalyst.

In still another embodiment, present invention, provides a vaccine composition comprising the triazolyl adjuvant and at least one antigen wherein the antigen is selected as a single or multiple component(s) from the group consisting of a protein of a pathogen, a recombinant protein, a peptide, a hapten, a polysaccharide, a glycoprotein, a lipopolysaccharide, a DNA molecule (polynucleotide), a cancer cell, a micro-organism, and mixtures thereof.

In still another embodiment of present invention, the vaccine is capable of efficiently inducing cell mediated immune response and producing antigen-specific antibodies.

In still another embodiment of present invention, the triazolyl adjuvant is capable of inducing long lasting antibodies comprising IgG1. IgG2a and other related subtypes of antibodies relevant for cell mediated immunity.

In still another embodiment of present invention, the triazolyl adjuvant is capable of inducing Th1 activation as evidence by the expression of cytokine response.

In still another embodiment, present invention provides a method for enhancing Th1 immune response comprising administrating the vaccine composition to a subject in need thereof.

In still another embodiment, present invention provides a method for inducing an immune response against a bacterial, viral or parasitic infection comprising administrating the adjuvant and at least one viral antigen or parasite antigen to a subject in need thereof.

| ABREVIATIONS USED | |
|---|---|
| MPL | Monophosphoryl lipid A |
| MDP | Muramyl dipeptides |
| QS21 | Quillaja saponins |
| PBS | Phosphate-buffered saline |
| OVA | Ovalbumin |
| HBsAg | Hepatitis B surface antigen |
| CD | Cluster of Differentiation |
| DC | Dendritic cell |
| PAMP | Pathogen associated molecular pattern |
| TLRs | Toll-Like Receptors |
| APCs | Antigen presenting cells |
| MALP-2 | Macrophage-activating lipopeptide-2 |
| LP-44 | 44-kDa lipoprotein |
| NF-kB | Nuclear factor kappa B |
| CTL | Cytotoxic T lymphocyte |
| IgG | immunoglobulin G |
| Th | T helper |
| BCG | Bacillus Calmette-Guerin |
| NDV | Newcastle disease virus |
| TB | Tuberculosis |
| LPS | Liposaccharide |
| HA | Haemagglutinin antigen |
| HPV | Human papilloma virus |
| HIV | Human immunodeficiency virus |
| CMV | Cytomegalovirus |
| RSV | Respiratory synctytial virus |
| DPT | Diphtheria, Pertussis and Tetanus |
| IFNγ | Interferon gamma |
| TNFα | Tumor necrosis factor alpha |
| IL | Interleukin |
| MTT | Triazolyl blue Tetrazolium Bromide |
| Av-HRP | Avidin-Horseradish Peroxidase |
| OD | Optical density |
| TMB | 3,3',5,5'-Tetramethylbenzidine |
| nm | Nanometer |
| μl | Micro liters |
| HEK | Human embryonic kidney |
| SEAP | Secreted embryonic alkaline phosphatase |
| NRK-49F | Rattus norvegicus kidney fibroblasts |
| BD | Becton Dickinson |
| FACS | Fluorescence-activated cell sorting |
| MFI | Mean Fluorescence Intensity |
| RBC | Red Blood Cells |
| DMSO | Dimethyl sulfoxide |
| $H_2SO_4$ | Sulphuric acid |
| $NaIO_4$ | Sodium periodate |
| THF | Tetrahydrofuran |
| $NaBH_4$ | Sodium borohydride |
| $PPh_3$ | Triphenyl phosphine (TPP) |
| LiOH | Lithium hydroxide |
| KF | Potassium Fluoride |
| DMF | Dimethyl formamide |
| AcOH | Acetic acid |
| DIC | Diisopropyl carbodiimide |

-continued

| ABREVIATIONS USED | |
|---|---|
| DMAP | 4-Dimethyl amino pyridine |
| TFA | Trifluoro acetic acid |
| HOBt | Hydroxybenzotriazole |
| EDCI | 1-Ethyl-3-(3-dimethylaminopropyl)carbodiimide |
| DIPEA | N,N-Diisopropylethylamine |
| ′BuOH | tert-Butanol |
| DCM | Dichloromethane |
| $Ac_2O$ | Acetic anhydride |
| $TMSN_3$ | Tri methyl silyl azide |
| NaOMe | Sodium Methoxide |
| $CuSO_4$ | Cupper Sulphate |
| EtOAc | Ethyl acetate |
| HCl | Hydro Chloric acid |
| TLC | Thin layer chromatography |
| NaHCO3 | Sodium Bicarbonate |
| $CHCl_3$ | Chloroform |
| $Na_2SO_4$ | Sodium Sulphate |

BRIEF DESCRIPTION OF THE DRAWINGS

FIG. 1 represents process steps for the synthesis of carbohydrate-di and tri lipidated cysteine based 1,2,3-triazoles useful as vaccine adjuvants for formula 1.

DETAILED DESCRIPTION OF THE INVENTION

The present invention provides for carbohydrate-di and tri lipidated cysteine based 1,2,3-triazoles useful as vaccine adjuvants for formula 1 and representative compounds thereof.

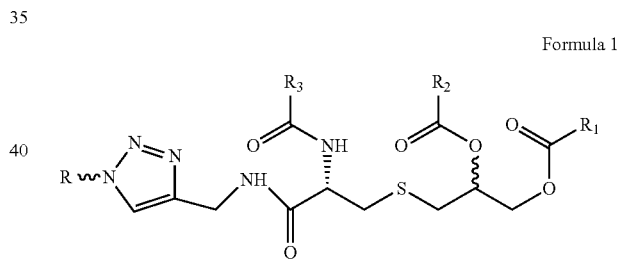

Formula 1

The Adjuvant increases or otherwise alters immune responses when mixed with an administered immunogenic. The adjuvant described in the present invention is the one that is able to induce a powerful antibody response as well as a cell-mediated immune response and that can switch an immunoglobulin isotype to produce IgG1 and IgG2a. The antigenic portion that constitutes a vaccine can be a microorganism (for example, virus or bacterium and the like) or a natural product purified from a microorganism, a synthetic or genetically engineered protein, peptide, polysaccharide or similar product termed as "subunit antigens" derived from pathogens causing various infections in humans. Examples of live vaccines include, but are not limited to, BCG, smallpox vaccination, polio, varicella, measles, rubella, mumps, rinderpest, NDV, Marek's disease and the like. Inactivated vaccines include, but are not limited to, pertussis, diphtheria (toxoid), tetanus (toxoid), influenza, Japanese encephalitis and the like. Subunit antigens may be derived from pathogens causing hepatitis, influenza. TB, malaria. Dengui, Chickun gunea, Japanese encephalitis or any other pathogens causing variety of humans and livestock infections. As used herein, the term Pam2cys/Pam3cys refers to the lipid head group of a pathogen associated molecular pattern.

As used herein, the phrase "powerful vaccine" refers to a vaccine formulation that can generate a large amount of high quality antigen specific antibody in reference to the most well known adjuvant aluminum hydroxide. In this regard, the generation of an appropriate, high quality antibody is a very important factor for producing a good preventive or an effective therapeutic vaccine. For example, different IgG isotypes play different roles in elimination of a tumor cells; IgG2a is the most effective one, compared with IgG1, IgG2b, or IgG3 are generated by cytokines produced by Th1 cells. Therefore, the induction of Th1 cell response is a good indication for the generation of an appropriate, high quality antibody. The most widely utilized adjuvant, Alum, induces Th 2 type immune response, and induced antibody is mainly IgG1. Thus, the powerful vaccine composition of the present invention is judged by the amount of an antigen specific antibody generated and high ratios of IgG2a/IgG1 compared to widely utilized Alum or other standard adjuvant containing vaccine.

Further, it is noted that, as used in the present application including this specification and the claims, the range of values, such as concentration ranges, percentage ranges, or ratio ranges, is understood such that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the present invention, subject to any specifically excluded limit in the stated range. Where the stated range includes one or both of the limits, ranges excluding either or both of those included limits are also included in the present invention. Further, for purposes of better understanding the present teachings and in no way limiting the scope of the teachings, unless otherwise indicated, all numbers expressing quantities, percentages or proportions, and other numerical values used in the specification and the claims, are to be understood as being modified in all instances by the term "about." Accordingly, unless indicated to the contrary, the numerical parameters set forth in the following specification and the claims are approximations that may vary depending upon the desired properties sought to be obtained. At the very least, each numerical parameter should at least be construed in light of the number of reported significant digits and by applying ordinary rounding techniques. Unless defined otherwise, all other technical and scientific terms used herein have the same meaning as commonly understood to one of ordinary skill in the art to which the present invention pertains.

The present invention, a synergistic adjuvant for a vaccine composition is provided. In particular, the synergistic adjuvant comprises one or more liposaccharides encompassing 1,2,3-triazoles that can stimulate immune responses in a synergistic way, instead of giving an additive effect by each adjuvant component.

The lipid head group used in the present invention is composed of lipid moiety linked to glycerol and cysteine. The carbohydrate moiety can be a any monosaccharide, disaccharide, tro saccharide, tetrasaccharide and oligosaccharide derived from either pentoses or hexoses, linked together through a 1,2,3-triazolyl methylene amine spacer that is designed as a substitute for any polycationin peptide derived from gram positive or gram negative bacteria The present invention in another aspect provides a vaccine composition comprising the synergistic adjuvant and at least one antigen such as ovalbumin or any other antigen derived from human or veterinary disease. The mixture of a liposaccharide used as an adjuvant to produce a vaccine composition in combination with experimental weak antigen ovalbumin or a real antigen such as an influenza antigen, or with a mixture of HBsAg S-protein etc. to enhance antigen-specific antibody production in a significant level, as compared to the most frequently used conventional adjuvant, Pam3CysSK4 (see Tables 4).

When the vaccine adjuvant conjugate of Formula (1) is used along with the antigen in a the vaccine composition, a synergistic effect in stimulating immune responses, that is, the titer of pre S antibody induced by the vaccine composition containing the mixture as an adjuvant was several times higher than the antibody titer induced by the individual antigen.

This increase of IgG2a vs IgG1, which is known to be very effective in defense against viral infection and cancer, suggests that the quality of immune response has improved with the new adjuvant according to the present invention. Further, these findings indicate that the lipidated cystenyl trizole based adjuvant of present invention can be effectively used for the development of powerful therapeutic and prophylactic vaccine formulations.

In a preferred embodiment of the present invention, a vaccine composition prepared using the adjuvant of the present invention vaccine adjuvant conjugate of Formula (1) was proved to synergistically increase the antigen specific antibody production, as well as changing the quality of immune response by inducing mostly IgG2a and IgG1. Therefore, an adjuvant composition containing the adjuvant components according to the present invention can be effectively used to increase immunogenicity of an antigen, thereby improving the efficacy of the vaccine containing the adjuvant and the antigen in combination.

The antigen that can be used in the present invention can be any material or substance that can induce immune responses by the immune system of an animal or human. It can be full length or a fragment. It can be a synthetic material, a purified subunit or a whole microbe or a mixture. A purified antigen is preferred. The antigen may include, but is not limited to, a recombinant protein, a peptide from hepatitis virus or viral protein from influenza virus, a polysaccharide, a glycoprotein, a lipopolysaccharide, a DNA molecule, a cancer cell, a live virus or a hapten molecule, etc. The protein of a pathogen may include, but is not limited to, influenza virus antigen (HA: haemagglutinin or neuraminidase antigen), *Bordetella pertussis* antigen, pertussis toxin, filamentous haemagglutinin, human papilloma virus (HPV)antigen, *Helicobacter pylori* antigen (capsular polysaccharides of serogroup A, B, C, Y and W-135), tetanus toxoid, diphtheria antigen (diphtheria toxoid), pneumococcal antigen (*Streptococcus pnemoniae* type 3 capsular polysaccharides), tuberculosis antigen, human immunodeficiency virus (HIV) antigen (GP-120, GP-160), cholera antigen (cholera toxin B subunit), staphylococcal antigen (staphylococcal enterotoxin B), *shigella* antigen (*shigella* polysaccharides), vesicular stomatitis virus antigen (vesicular stomatitis virus glycoprotein), cytomegalovirus (CMV) antigen, hepatitis antigen [hepatitis A(HAV), B(HBV), C(HCV), D(HDV)and G(HGV): L-HBsAg, S-HBsAg, M-HBsAg, pre S], respiratory synctytial virus (RSV)antigen, herpes simplex antigen and combinations thereof (ex: diphtheria, pertussis and tetanus; DPT).

The vaccine composition of the present invention can be administered parenterally by various routes such as subcutaneous injection, intravenous injection, intramuscular injection and intrathoracic injection. The vaccine composition covered in this invention may be administered through mucosal route using an appropriate mico/nano emulsion, micro/nano particle or liposomal vehicle for non invasive delivery of vaccines.

The present invention provides a method for enhancing Th1 immune response by administering the vaccine composition according to the present invention to a subject in need thereof. In a preferred embodiment of the present invention, the vaccine composition prepared by using the adjuvant of the present invention increased IgG2a and IgG1 production and high ration of IgG2a vs IgG1 antibodies produced by this conjugates in conjunction with an appropriate antigen clearly indicate powerful Th1 activation leading to cell mediate dimmunity required for various viral infections and other deseases involving intracellular pathogenesis and cancer. Further, the efficacy of Th1 activation by the compounds of ##structure-1##along with a specific antigen is evidence by its proven ability to elicit Th1 cytokines like IFNγ, TNF-α and IL2. (see Tables 2). Therefore, the vaccine composition of the present invention can be effectively used for enhancing Th1 immune response to improve immunogenicity of an antigen.

The precursor propargylated di and tri lipidated cysteine and azido carbohydrate fragments have been prepared as illustrated in the Schemes.

(i) the propargylated di and tri lipidated cysteine fragment was prepared starting from cyclohexylidine mannitol which was subjected to vicinal diol cleavage using $NaIO_4$ oxidation to afford the corresponding aldehyde which was reduced to alcohol using $NaBH_4$/MeOH which was converted to iodo derivative using $TPP/I_2$ and Imidazole in quantitative yield;
(ii) The corresponding iodo derivative was reacted with N-Boc protected cysteine to get the corresponding protected cysteinyl glycerol unit. Deprotection of cyclohexyl moiety under acid treatment affords the diol which was subjected to palmitoylation using Palmitoyl chloride and TEA to afford the di lipidated cysteine; (iii) Boc protected pam2cys treated with 20% TFA:DCM for 30 min then resulting amine treated with triethyl amine followed by palmitoyl chloride to afford phenasyl protected pam3cys. The corresponding compound dissolved in AcOH then activated Zn powder added stirred for 2 hrs, resulting acid coupled with propargyl amine to afford required Propargylamido di and tri lipidated cysteine (11); iv) Carbohydrate treated with $Ac_2O$/DCM and triethyl amine stirred for 30 min to get penta acylated compound. The corresponding compound reacted with $TMSN_3$/$SnCl_4$ for 30 min, acylated azido carbohydrate treated with NaOMe/MeOH to afforded hydrophilic azido carbohydrate;
(v) Propargylamido pam3cys and azido carbohydrate reacted under sodiumascrobate/$CuSO_4$ in tBuOH:$H_2O$ for overnight at room temperature to get final compound.

All the 1,2,3-Triazole-tethered carbohydrate di- and tri lipidated cysteine based conjugates have been synthesized and purified by column chromatography using different solvents like ethyl acetate, hexane, chloroform and methanol have been performed.

EXAMPLES

The following examples are given by way of illustration and therefore should not be construed to the present limit of the scope of invention.

Process for the Preparation of Vaccine Adjuvant Conjugate of Formula (1)

(i) Preparation of (S)-2-oxo-2-phenylethyl-3-((R)-1,4-dioxaspiro[4,5]decan-2-ylmethylthio)-2-(tert-butoxycarbonylamino)propanoate (6): N-(tert-Butoxycarbonyl)-L-cysteine methylester was procured from commercial source. Iodo compound (Scheme-1, 4) was prepared form D-mannitol (Scheme-1, 1) following a literature procedure (Reference; Srihari. P, Vijaya Bhasker. E. Bal Reddy A. Yadav J. S, *Tetrahedron Letters* 50 (2009) 2420-2424). N-(tert-Butoxycarbonyl)-L-cysteine methylester (3 g, 12.76 mmol)and Iodo compound (4.31 g, 15.31 mmol)and was dissolved in Dry DMF (30 mL) with stirring. To The resulting solution DIPEA (4.43 mL, 25.52 mmol) was added slowly at room temperature. The resulting mixture was stirred for 2 h at room temperature, followed by addition of ice cold water and the aqueous layer was extracted with EtOAc (2×50 ml). The organic layer washed with 1N HCl (2×50 ml), then organic layer was dried over anhydrous sodium sulphate and concentrated in vacuo and the resulting residue used for next step without further purification. Thus obtained methyl ester compound (4.8 g, 12.33 mmol) dissolved in THF:H2O (40 mL, 4:1) then LiOH.H2O (0.3 g, 12.33 mmol) was added stirred for 30 min. TLC checked solvent removed by rotavacc, with 10% HCl neutralize the reaction mixture then extracted with EtOAc (2×50 mL). The organic layer washed with NaHCO3 (2×50 mL), Then organic layers was dried over anhydrous sodium sulphate and concentrated in vacuo and the resulting residue used for next step without further purification. The obtained acid (3.7 g, 9.86 mmol)and 2-bromo acetophenone (2.95 g, 14.8 mmol) were dissolved in dry DMF with stirring. KF (1.2 g, 19.72 mmol)added to the solution and stirred at room temperature for 2.5 h. Ice cold water was added to the reaction mixture and stirred for 30 min, then extracted with EtOAc (2×100 mL). The organic layers dried over anhydrous sodium sulphate and evaporated under reduced pressure to afford the crude product, which was subjected to column chromatography in 20% EtOAc-hexane. Yellow solid (3.85 g, 80%).

IR (KBr, cm-1): 2918, 2850, 2310, 1729, 1663, 1551, 1466, 1219, 1161, 1069, 772, 722, 688; 1H NMR (300 MHz, CDCl3): δ 1.46 (s, 9H), 1.53-1.67 (m, 10H), 2.68-2.73 (dd, J=6.4, 6.5 Hz, 1H), 2.84-2.89 (dd, J=5.9, 13.5 Hz, 1H), 3.14-3.26 (ddd, J=4.5, 6.4, 6.5 Hz, 2H), 3.7-3.7 (dd, J=6.4, 8.2 Hz, 1H) 4.08-4.12 (dd, J=6.1, 8.2 Hz, 1H), 4.25.4.31 Hz (m, 1H), 4.66-4.71 (m, 1H), 5.32-5.37 (d, J=16.3 Hz, 1H), 5.47-5.53 (t, J=8.5 Hz, 2H) 7.48-7.52 (t, J=7.6 Hz, 2H), 7.60-7.64 (t, J=7.3 Hz, 1H), 7.89-7.92 (d, J=9.0 Hz, 2H), 13C NMR (75 MHz, CDCl3): δ 23.7, 23.9, 25.08, 28.2, 34.9, 35.8, 36.4, 53.6, 66.5, 68.3, 75.3, 80.1, 110.2, 127.7, 128.8, 133.8, 134.03, 170.6, 191.1. MS (ESI): m/z 516 [M+Na]+.

(ii) General Procedure for Dilipidated Compound (8) Compound 6 (7.3 mmol) was dissolved in 70% AcOH:$H_2O$, then stirred at room temperature for 8 h until the complete consumption of starting material as revealed by TLC examination. The excess solvent evaporated under reduced pressure and the resulting residue was co-evaporated with hexane. Residue obtained was used in next step without further purification. The residue (Scheme-1, 7) obtained dissolved in dry THF to long chain carboxylic acid (21.8 mmol), DIC (3.6 g, 27.9 m mol). DMAP (0.35 g, 2.9 mmol), were added respectively, then the mixture was stirred for 2 h at room temperature after which glacial acetic acid (0.9 mil)added. The mixture was concentrated under reducing pressure, residue recrystalised from DCM/MeOH (1:20 v/v) at −20° C., to give 8 (70-80%).

For $R_1/R_2=C_{15}H_{31}$ in Scheme 1, compound 8): (R)-3-((S)-2-(tert-butoxycarbonylamino)-3-oxo-3-(2-oxo-2-phenylethoxy)propylthio)propane-1,2-diyl dipalmitate Light yellow colour solid.

$^1$H NMR (300 MHz. CDCl$_3$): δ 88 (t, J=6.2 Hz, 6H), 1.17-1.35 (m, 48H), 1.46 (S, 9H), 1.56-1.65 (m, 6H), 2.26-2.36 (q, J=6.9, 7.1 Hz, 4H), 2.8 (d, J=6.2, 2H), 3.09 (dd, J=6.4, 13.9 Hz, 1H), 3.26 (dd, J=4.1, 4.3 Hz, 1H), 4.19 (dd, J=5.8, 6.0 Hz, 1H), 4.36 (dd, J=3.3.3.5 Hz, 1H), 4.63-4.73 (m, 1H), 5.15-5.24 (m, 1H), 5.3-5.56 (m, 3H), 7.50 (t, J=7.5 Hz, 2H) 7.59-7.66 (t, J=7.3 Hz, 1H), 7.91 (d, J=7.3, 2H), (iii) General Procedure for Trilipidated Alkyne Compound 11: Compound 8 (6.74 mmol) was dissolved in 20% TFA: DCM, stirred at room temperature for 30 minutes, after completion of start material excess solvent was evaporated by rota vacuo. Residue co-evaporated with hexane then subjected to aziotropic evaporation with toluene and the residue obtained was used in the next step. Resulting amine compound (Scheme-1.6.7 mmol) was dissolved in dry DCM and the solution was added to the long chain carboxylic acid (8.04 mmol), DIC (1.03 g, 8.04 mmol), HOBt (1.23 g, 8.04 mmol) in dry DCM, which was stirred at room temperature for 8h. After that diluted with DCM, filtered washed with water (2×50 ml), sat NaHCO$_3$ (2×50 ml). The pooled up aqueous layers extracted DCM (2×20 ml) the combined organic layers dried over anhydrous Na$_2$SO$_4$, evaporated by rota vacuo. The residue was dissolved in acetic acid (70 ml)at room temperature was added activated Zn (4.95 g, 76.2 mmol)and stirred the mixture for 2 h at room temperature. After complete consumption of the starting material, the reaction mass was filtered through celite and the filtrate was evaporated under reduced pressure to afford crude product. Purification of the crude product by column chromatography resulted in pure compound (Scheme-1,10) which in turn was dissolved in dry DCM under N$_2$ atmosphere, EDCI (0.98 g, 5.1 mmol), HOBt (0.785 g, 5.1 mmol) were added stirred for 10 m, then Propargyl amine (0.235 g, 4.2 m mol), DIPEA (0.828 g, 6.4 mmol) were added at 0° C. The resulting mixture allow to warm to room temperature stirred for 8 h. Then reaction mixture diluted with DCM (50 ml). The organic layer washed with water (2×50 ml)and sat NaHCO$_3$ (2×50 ml). Organic layer dried over Na$_2$SO$_4$, then purified by column chromatography (20% EtOAc:Hexane) to give compound 11 in 65-77% yield.

For $R_1/R_2/R_3=C_{15}H_{31}$ in Scheme 1, compound 11): Preparation of (R)-3-((S)-3-oxo-2-palmitamido-3-(prop-2-ynylamino)propylthio)propane-1,2-diyl dipalmitate: White solid, mp 81° C.; $^1$H NMR (300 MHz, CDCl$_3$): δ 88 (t, J=6.232 Hz, 9 H), 1.17-1.37 (m, 72 H), 1.54-1.64 (m, 6 H), 2.27 (t, J=2.64, 1 H), 2.3-2.4 (m, 6 H), 2.84 (dd, J=5.22, 7.93, 2 H), 2.93 (dd, J=2.83, 4.92, 2 H), 4.09 (dd, J=2.4, 5.28, 2 H), 4.2 (dd, J=3.7, 1 H), 4.28 (dd, J=5.8, 12.08, 1 H), 4.62 (dd, J=7.63, 13.21, 1 H), 5.28-5.37 (m, 1 H), 7.0 (t, J=3.77, 1 H), 7.5 (t, J=6.798, 1 H).

(iv) General Procedure Preparation of Di- and Tri-Lipidated Cysteine Based Carbohydrate/Polyhydroxy Alkyl Triazoles: Di- and tri-lipidated cysteine alkyne (Scheme-1, 11) (0.1 g, 0.01 mmol) was stirred in tertiary butanol and water (1:1 mixture, 5 ml) to which copper sulfate (0.042 mmol)and sodium ascorbate (0.042 mmol) were added and the reaction mixture was stirred at RT, after 15 minutes, Carbohydrate/polyhydoxy alkyl azide compound (prepared from literature procedure, Ref. Eric Benoist et al. *Carbohydrate Research* 346 (2011) 26-34, Scheme-1, 12) (0.01 mmol) was added and the mixture was allowed to stir for 8 hours at RT. Tertiary butanol was evaporated under reduced pressure, diluted with CHCl$_3$ and water. The organic layer was sepa-rated and aqueous layer extracted with CHCl$_3$ (2×100 ml). The combined organic layers were dried over anhydrous Na$_2$SO$_4$ and evaporated under reduced pressure to afford the crude product which was purified by column chromatography (10% MeOH: CHCl$_3$) to afford pure product as white solid (80-98%).

Example 1

(R)-3-((S)-3-((1-((R)-2,3-dihydroxypropyl)-1H-1,2,3-triazol-4-yl)amino)-3-oxo-2-palmitamido-propylthio)propane-1,2-diyldipalmitate (30a):

$^1$H NMR (300 MHz, DMSO-d$_6$): δ 0.84 (t, J=5.0 Hz, 9H), 1.13-1.36 (m, 72H), 1.39-1.56 (m, 6H), 2.24 (t, J=6.9, 6H), 2.63-2.84 (m, 3H), 2.97 (dd, J=7.5 Hz, 1H), 3.7 (dd, J=4.9 Hz, 1H), 3.99-4.15 (m, 3H), 4.23-4.59 (m, 8H), 5.1 (m, 1H), 7.86 (s, 1H), 8.81 (dd, J=5.6, 5.8 Hz, 1H), 9.69 (d, J=8.1 Hz, 1H). MS (ESI): m/z 1087 [M+Na]$^+$.

Example-2

(R)-3-((S)-2-amino-3-((1-((R)-2,3-dihydroxypropyl)-1H-1,2,3-triazol-4-yl)amino)-3-oxopropylthio)propane-1,2-diyl dihexanoate (7a): Di and tri lipidated cysteine alkyne (Scheme-1, 11) (0.01 mmol) was stirred in tertiary butanol and water (1:1 mixture, 5 ml) to which copper sulfate (0.042 mmol)and sodium ascorbate (0.042 mmol) were added and the reaction mixture was stirred at RT, after 15 minutes, 1-β-azido glucose (0.021 g, 0.01) was added and the mixture was allowed to stir for 8 hours at RT. Tertiary butanol was evaporated under reduced pressure, diluted with CHCl$_3$ and water. The organic layer was separated and aqueous layer extracted with CHCl$_3$ (2×100 ml). The combined organic layers were dried over Na$_2$SO$_4$ and evaporated under reduced pressure to afford the crude product which was purified by column chromatography (10% MeOH: CHCl$_3$) to afford pure product as white solid (82%).

$^1$H NMR (300 MHz, DMSO-d$_6$): δ 0.84 (t, J=5.0 Hz, 6H), 1.13-1.36 (m, 8H), 1.39-1.56 (m, 4H), 2.24 (t, J=6.9, 4H), 2.63-2.84 (m, 3H), 2.97 (dd, J=7.5 Hz, 1H), 3.7(dd, J=4.9 Hz, 1H), 3.99-4.15 (m, 3H), 4.23-4.59 (m, 8H), 5.1 (m, 1H), 7.86 (s, 1H), 8.81 (dd, J=5.6, 5.8 Hz, 1H), 9.69 (d, J=8.1 Hz, 1H). MS (ESI): m/z 531 [M+Na]$^+$.

Example 3

(2R)-3-((2S)-3-oxo-2-palmitamido-3-((1-((2S)-3,4,5-trihydroxy-6(hydroxymethyl)tetrahydro-2H-pyran-2-yl)-1H-1,2,3-triazol-4-yl)amino)propylthio)propane-1,2-diyl dipalmitate (30b): Di and tri lipidated cysteine alkyne (Scheme-1, 11) (0.01 mmol) was stirred in tertiary butanol and water (1:1 mixture, 5 ml) to which copper sulfate (0.042 mmol)and sodium ascorbate (0.042 mmol) were added and the reaction mixture was stirred at RT, after 15 minutes, sugar azide (0.021 g, 0.01) was added and the mixture was allowed to stir for 8 hours at RT. Tertiary butanol was evaporated under reduced pressure, diluted with CHCl$_3$ and water. The organic layer was separated and aqueous layer extracted with CHCl$_3$ (2×100 ml). The combined organic layers were dried over Na$_2$SO$_4$ and evaporated under reduced pressure to afford the crude product which was purified by column chromatography (10% MeOH: CHCl$_3$) to afford pure product as white solid (78%).

$^1$H NMR (300 MHz, DMSO-d$_6$): δ 0.82 (t, J=6.7 Hz, 9H), 1.09-1.3 (m, 72H), 1.4-1.53 (m, 6H), 2.22 (t, J=7.1 Hz, 6H), 2.61-2.85 (m, 3H), 2.97-3.06 (dd, J=3.5, 13.4, 1H), 3.6-3.76 (m, 2H), 4.06 (dd, J=6.6, 6.7, 1H), 4.19-4.33 (m, 2H), 4.38

(dd, J=5.4, 5.2 Hz, 1H), 4.44-4.54 (m, 1H), 4.62 (t, J=5.4 Hz, 1H), 5.08 (m, 1H), 5.14 (d, J=5.4 Hz, 1H), 5.27 (d, J=4.9 Hz, 1H), 5.34 (d, J=6.1 Hz, 1H), 5.48 (d, J=9.2, 1H), 8.06 (s, 1H), 8.78 (t, J=5.1, 5.4 Hz, 1H), 9.66 (d, J=8.1, 1H). MS (ESI): m/z 1175 [M+Na]$^+$.

Example 4

(2R)-3-(((2S)-2-amino-3-oxo-3-((1-((2S)-3,4,5-trihydroxy-6-(hydroxymethyl)tetrahydro-2H-pyran-2-yl)-1H-1,2,3-triazol-4-yl)amino)propyl)thio)propane-1,2-diyl diheptanoate (8b): Di and tri lipidated cysteine alkyne (Scheme-1, 11) (0.01 mmol) was stirred in tertiary butanol and water (1:1 mixture, 5 ml) to which copper sulfate (0.042 mmol)and sodium ascorbate (0.042 mmol) were added and the reaction mixture was stirred at RT, after 15 minutes, sugar azide (0.021 g, 0.01) was added and the mixture was allowed to stir for 8 hours at RT. Tertiary butanol was evaporated under reduced pressure, diluted with CHCl$_3$ and water. The organic layer was separated and aqueous layer extracted with CHCl$_3$ (2×100 ml). The combined organic layers were dried over Na$_2$SO$_4$ and evaporated under reduced pressure to afford the crude product which was purified by column chromatography (10% MeOH: CHCl$_3$) to afford pure product as white solid (81%).

$^1$H NMR (300 MHz, DMSO-d$_6$): δ 0.82 (t, J=6.7 Hz, 6H), 1.09-1.3 (m, 12H), 1.4-1.53 (m, 0.4H), 2.22 (t, J=7.1 Hz, 4H), 2.61-2.85 (m, 3H), 2.97-3.06 (dd, J=3.5, 13.4, 1H), 3.6-3.76 (m, 2H), 4.06 (dd, J=6.6, 6.7, 1H), 4.19-4.33 (m, 2H), 4.38 (dd, J=5.4, 5.2 Hz, 1H), 4.44-4.54 (m, 1H), 4.62 (t, J=5.4 Hz, 1H), 5.08 (m, 1H), 5.14 (d, J=5.4 Hz, 1H), 5.27 (d, J=4.9 Hz, 1H), 5.34 (d, J=6.1 Hz, 1H), 5.48 (d, J=9.2, 1H), 8.06 (s, 1H), 8.78 (t, J=5.1,5.4 Hz, 1H), 9.66 (d, J=8.1, 1H). MS (ESI): m/z 647 [M+Na]$^+$.

Example 5

(2R)-3-((2S)-3-((1-((2S)-2-hydroxy-2-((3S,4S)-3,4,5-trihydroxytetrahydrofuran-2-yl)ethyl)-1H-1,2,3-triazol-4-yl)amino)-3-oxo-2-palmitamidopropylthio)propane-1,2-diyl dipalmitate (30c): di and tri lipidated cysteine alkyne (Scheme-1, 11) (0.01 mmol) was stirred in tertiary butanol and water (1:1 mixture, 5 ml) to which copper sulfate (0.042 mmol)and sodium ascorbate (0.042 mmol) were added and the reaction mixture was stirred at RT, after 15 minutes, sugar azide (0.021 g, 0.01) was added and the mixture was allowed to stir for 8 hours at RT. Tertiary butanol was evaporated under reduced pressure, diluted with CHCl$_3$ and water. The organic layer was separated and aqueous layer extracted with CHCl$_3$ (2×100 ml). The combined organic layers were dried over Na$_2$SO$_4$ and evaporated under reduced pressure to afford the crude product which was purified by column chromatography (10% MeOH: CHCl$_3$) to afford pure product as white solid (82%).

$^1$H NMR (300 MHz, DMSO-d$_6$): 0.88(t, J=6.2 Hz, 9H), 1.15-1.34 (m, 72H), 1.47-1.57 (m, 6H), 2.18-2.33 (t, J=7.1 Hz, 6H), 2.7-2.88 (m, 2H), 2.91-3.23 (m, 2H), 3.99 (dd, J=8.0, 8.2 Hz, 1H), 4.13 (dd, J=6.1, 6.8, 1H), 4.25-4.44 (m, 4H), 4.53 (br, 1H), 4.59-4.72 (m, 2H), 4.83-4.92 (dd, J=4.7, 3.6, 4.1 Hz, 1H), 4.96-5.06 (dd, J=4.7 Hz, 1H), 5.13 (br, 1H), 5.28-5.38 (dd, J=5.3, 5.4 Hz, 1H), 6.39 (d, J=4.7 Hz, 1H), 6.74 (d, J=6.5 Hz, 1H), 7.84 (s, 1H), 7.89 (s, 1H), 8.8 (dd, J=4.8,5.1 Hz, 1H), 9.7 (s, 1H). MS (ESI): m/z 1175 [M+Na]$^+$.

Example 6

(2R)-3-(((2S)-2-amino-3-((1-((2S)-2-hydroxy-2-((3S,4S)-3,4,5-trihydroxytetrahydrofuran-2-yl)ethyl)-1H-1,2,3-triazol-4-yl)amino)-3-oxopropyl)thio)propane-1,2-diyl dioctanoate (9c) di and tri lipidated cysteine alkyne (Scheme-1, 11) (0.01 mmol) was stirred in tertiary butanol and water (1:1 mixture, 5 ml) to which copper sulfate (0.042 mmol) and sodium ascorbate (0.042 mmol) were added and the reaction mixture was stirred at RT, after 15 minutes, sugar azide (0.021 g,0.01) was added and the mixture was allowed to stir for 8 hours at RT. Tertiary butanol was evaporated under reduced pressure, diluted with CHCl$_3$ and water. The organic layer was separated and aqueous layer extracted with CHCl$_3$ (2×100 ml). The combined organic layers were dried over Na$_2$SO$_4$ and evaporated under reduced pressure to afford the crude product which was purified by column chromatography (10% MeOH: CHCl$_3$) to afford pure product as white solid (86%).

$^1$H NMR (300 MHz, DMSO-d$_6$): 0.88(t, J=6.2 Hz, 6H), 1.15-1.34 (m, 16H), 1.47-1.57 (m, 4H), 2.18-2.33 (t, J=7.1 Hz, 4H), 2.7-2.88 (m, 2H), 2.91-3.23 (m, 2H), 3.99 (dd, J=8.0, 8.2 Hz, 1H), 4.13 (dd, J=6.1, 6.8, 1H), 4.25-4.44 (m, 4H), 4.53 (br, 1H), 4.59-4.72 (m, 2H), 4.83-4.92 (dd, J=4.7, 3.6, 4.1 Hz, 1H), 4.96-5.06 (dd, J=4.7 Hz, 1H), 5.13 (br, 1H), 5.28-5.38 (dd, J=5.3, 5.4 Hz, 1H), 6.39 (d, J=4.7 Hz, 1H), 6.74 (d, J=6.5 Hz, 1H), 7.84 (s, 1H), 7.89 (s, 1H), 8.8 (dd, J=4.8.5.1 Hz, 1H), 9.7 (s, 1H). MS (ESI): m/z 675 [M+Na]$^+$.

Example 7

(R)-3-((S)-3-oxo-2-palmitamido-3-((1-((2S,3S,4R,5R)-2,3,4,5,6-pentahydroxyhexyl)-1H-1,2,3-triazol-4-yl)amino)propylthio)propane-1,2-diyl dipalmitate (30d): di and tri lipidated cysteine alkyne (Scheme-1, 11) (0.01 mmol) was stirred in tertiary butanol and water (1:1 mixture, 5 ml) to which copper sulfate (0.042 mmol)and sodium ascorbate (0.042 mmol) were added and the reaction mixture was stirred at RT, after 15 minutes, sugar azide (0.021 g, 0.01) was added and the mixture was allowed to stir for 8 hours at RT. Tertiary butanol was evaporated under reduced pressure, diluted with CHCl$_3$ and water. The organic layer was separated and aqueous layer extracted with CHCl$_3$ (2×100 ml). The combined organic layers were dried over Na$_2$SO$_4$ and evaporated under reduced pressure to afford the crude product which was purified by column chromatography (10% MeOH: CHCl$_3$) to afford pure product as white solid (80%).

$^1$H NMR (300 MHz, DMSO-d$_6$): 0.82 (t, J=6.1 Hz, 9H), 1.09-1.29 (m, 72H), 1.39-1.53 (m, 6H),2.18-2.27 (m, 6H), 2.62-2.84 (m, 3H), 3.0 (dd, J=3.5, 3.9 Hz, 1H), 3.74(dd, J=6.1, 7.3 Hz, 1H), 4.06 (dd, J=6.7, 6.9 Hz, 1H), 4.16-4.4 (m, 7H), 4.47 (dd, J=5.1, 7.3 Hz, 3H), 4.63 (dd, J=1.8, 2.1 Hz, 1H), 4.99 (d, J=6.7 Hz, 1H), 5.08 (br, 1H), 7.81 (s, 1H), 8.76 (dd, J=5.1, 5.4 Hz, 1H), 9.65 (d, J=8.3 Hz, 1H), MS (ESI): m/z 1177 [M+Na]$^+$.

Example 8

(R)-3-(((S)-2-amino-3-oxo-3-((1-((2S,3S,4R,5R)-2,3,4,5,6-pentahydroxyhexyl)-1H-1,2,3-triazol-4-yl)amino)propyl)thio)propane-1,2-diyl dinonanoate (10d): di and tri lipidated cysteine alkyne (Scheme-1, 11) (0.01 mmol) was stirred in tertiary butanol and water (1:1 mixture, 5 ml) to which copper sulfate (0.042 mmol)and sodium ascorbate (0.042 mmol) were added and the reaction mixture was stirred at RT, after 15 minutes, sugar azide (0.021 g, 0.01) was added and the mixture was allowed to stir for 8 hours at RT. Tertiary butanol was evaporated under reduced pressure, diluted with CHCl$_3$ and water. The organic layer was separated and aqueous layer extracted with CHCl$_3$ (2×100 ml).

The combined organic layers were dried over Na₂SO₄ and evaporated under reduced pressure to afford the crude product which was purified by column chromatography (10% MeOH: CHCl₃) to afford pure product as white solid (83%).

White solid, mp 142° C.: ¹H NMR (300 MHz, DMSO-d₆): 0.82 (t, J=6.1 Hz, 6H), 1.09-1.29 (m, 20 H), 1.39-1.53 (m, 4H), 2.18-2.27 (m, 4H), 2.62-2.84 (m, 3H), 3.0 (dd, J=3.5, 3.9 Hz, 1H), 3.74 (dd, J=6.1,7.3 Hz, 1H), 4.06 (dd, J=6.7,6.9 Hz, 1H), 4.16-4.4 (m, 7H), 4.47 (dd, J=5.1,7.3 Hz, 3H), 4.63 (dd, J=1.8, 2.1 Hz, 1H), 4.99 (d, J=6.7 Hz, 1H), 5.08 (br, 1H), 7.81 (s, 1H), 8.76 (dd, J=5.1, 5.4 Hz, 1H), 9.65 (d, J=8.3 Hz, 1H). MS (ESI): m/z 705 [M+Na]⁺.

Example 9

(2R)-3-((2S)-3-((1-((2S,3R,4S)-3,4-dihydroxy-5-(hydroxymethyl)tetrahydrofuran-2-yl)-1H-1,2,3-triazol-4-yl)amino)-3-oxo-2-palmitamidopropylthio)propane-1,2-diyl-dipalmitate (30e): di and tri lipidated cysteine alkyne (Scheme-1, 11) (0.01 mmol) was stirred in tertiary butanol and water (1:1 mixture, 5 ml) to which copper sulfate (0.042 mmol) and sodium ascorbate (0.042 mmol) were added and the reaction mixture was stirred at RT, after 15 minutes, sugar azide (0.021 g, 0.01) was added and the mixture was allowed to stir for 8 hours at RT. Tertiary butanol was evaporated under reduced pressure, diluted with CHCl₃ and water. The organic layer was separated and aqueous layer extracted with CHCl₃ (2×100 ml). The combined organic layers were dried over Na₂SO₄ and evaporated under reduced pressure to afford the crude product which was purified by column chromatography (10% MeOH: CHCl₃) to afford pure product as white solid (85%).

¹H NMR (300 MHz, DMSO-d₆): 0.84 (t, J=6.4 Hz, 9H), 1.12-1.32 (m, 72H), 1.44-1.54 (m, 6H), 2.25 (t, J=6.4 Hz, 6H), 2.66-2.86 (m, 3H), 2.98-3.06 (dd, J=4.2, 4.5 Hz, 1H), 3.69-3.84 (m, 2H), 4.09 (q, 1H), 4.23-4.4 (m, 4H), 4.5 (m, 1 Hz, 1H), 5.09 (s, 1H), 5.45 (d, J=9.1 Hz, 1H), 8.05 (s, 1H), 8.81 (dd, J=4.4, 4.8 Hz, 1H). MS (ESI): m/z 1145 [M+Na]⁺.

Example 10

(2R)-1-(((2S)-2-decanamido-3-((1-((2S,3R,4S)-3,4-dihydroxy-5-(hydroxymethyl)tetrahydrofuran-2-yl)-1H-1,2,3-triazol-4-yl)amino)-3-oxopropyl)thio)-3-(nonanoyloxy)propan-2-yl decanoate (11e): di and tri lipidated cysteine alkyne (Scheme-1, 11) (0.01 mmol) was stirred in tertiary butanol and water (1:1 mixture, 5 ml) to which copper sulfate (0.042 mmol) and sodium ascorbate (0.042 mmol) were added and the reaction mixture was stirred at RT, after 15 minutes, sugar azide (0.021 g, 0.01) was added and the mixture was allowed to stir for 8 hours at RT. Tertiary butanol was evaporated under reduced pressure, diluted with CHCl₃ and water. The organic layer was separated and aqueous layer extracted with CHCl₃ (2×100 ml). The combined organic layers were dried over Na₂SO₄ and evaporated under reduced pressure to afford the crude product which was purified by column chromatography (10% MeOH:CHCl₃) to afford pure product as white solid (91%).

¹H NMR (300 MHz. DMSO-d₆): 0.84 (t, J=6.4 Hz, 9H), 1.12-1.32 (m, 36H), 1.44-1.54 (m, 6H), 2.25 (t, J=6.4 Hz, 6H), 2.66-2.86 (m, 3H), 2.98-3.06 (dd, J=4.2, 4.5 Hz, 1H), 3.69-3.84 (m, 2H), 4.09 (q, 1H), 4.23-4.4 (m, 4H), 4.5 (m, 1 Hz, 1H), 5.09 (s, 1H), 5.45 (d, J=9.1 Hz, 1H), 8.05 (s, 1H), 8.81 (dd, J=4.4, 4.8 Hz, 1H). MS (ESI): m/z 842 [M+Na]⁺.

Example 10

(2R)-3-((2S)-3-((1-((2S,3S,4S)-3,4-dihydroxy-5-(hydroxymethyl)tetrahydrofuran-2-yl)-1H-1,2,3-triazol-4-yl)amino)-3-oxo-2-palmitamidopropylthio)propane-1,2-diyl dipalmitate (30f): di and tri lipidated cysteine alkyne (Scheme-1, 11) (0.01 mmol) was stirred in tertiary butanol and water (1:1 mixture, 5 ml) to which copper sulfate (0.042 mmol) and sodium ascorbate (0.042 mmol) were added and the reaction mixture was stirred at RT, after 15 minutes, sugar azide (0.021 g, 0.01) was added and the mixture was allowed to stir for 8 hours at RT. Tertiary butanol was evaporated under reduced pressure, diluted with CHCl₃ and water. The organic layer was separated and aqueous layer extracted with CHCl₃ (2×100 ml). The combined organic layers were dried over Na₂SO₄ and evaporated under reduced pressure to afford the crude product which was purified by column chromatography (10% MeOH: CHCl₃) to afford pure product as white solid (87%).

¹H NMR (300 MHz, DMSO-d₆): 0.84 (t, J=6.2 Hz, 9H), 1.11-1.35 (m, 72H), 1.4-1.55 (m, 6H), 2.25 (t, J=6.7 Hz, 6H), 2.64-2.86 (m, 3H), 2.95-3.08 (m, 1H), 3.66-3.85 (m, 2H), 4.04-4.13 (m, 1H), 4.22-4.56 (m, 3H), 5.09 (br, 1H), 5.2 (d, J=4.7 Hz, 1H), 5.33 (d, J=4.5 Hz, 1H), 5.42 (dd, J=5.8, 9.2 Hz, 1H), 8.06 (s, 1H), 9.69 (d, J=7.7 Hz, 1H). MS (ESI): m/z 1145 [M+Na]⁺.

Example 11

2R)-3-(((2S)-3-((1-((2S,3S,4S)-3,4-dihydroxy-5-(hydroxymethyl)tetrahydrofuran-2-yl)-1H-1,2,3-triazol-4-yl)amino)-3-oxo-2-undecanamidopropyl)thio)propane-1,2-diyl diundecanoate (25f): di and tri lipidated cysteine alkyne (Scheme-1, 11) (0.01 mmol) was stirred in tertiary butanol and water(1:1 mixture, 5 ml) to which copper sulfate (0.042 mmol) and sodium ascorbate (0.042 mmol) were added and the reaction mixture was stirred at RT, after 15 minutes, sugar azide (0.021 g,0.01) was added and the mixture was allowed to stir for 8 hours at RT. Tertiary butanol was evaporated under reduced pressure, diluted with CHCl₃ and water. The organic layer was separated and aqueous layer extracted with CHCl₃ (2×100 ml). The combined organic layers were dried over Na₂SO₄ and evaporated under reduced pressure to afford the crude product which was purified by column chromatography (10% MeOH: CHCl₃) to afford pure product as white solid (85%).

¹H NMR (300 MHz, DMSO-d₆): 0.84 (t, J=6.2 Hz, 9H), 1.11-1.35 (m, 42H), 1.4-1.55 (m, 6H), 2.25 (t, J=6.7 Hz, 6H), 2.64-2.86 (m, 3H), 2.95-3.08 (m, 1H), 3.66-3.85 (m, 2H), 4.04-4.13 (m, 1H), 4.22-4.56 (m, 3H), 5.09 (br, 1H), 5.2 (d, J=4.7 Hz, 1H), 5.33 (d, J=4.5 Hz, 1H), 5.42 (dd, J=5.8, 9.2 Hz, 1H), 8.06 (s, 1H), 9.69 (d, J=7.7 Hz, 1H). MS (ESI): m/z 898 [M+Na]⁺.

Example 12

(2R)-3-((2S)-3-oxo-2-palmitamido-3-((1-((2R)-3,4,5-trihydroxy6-hydroxymethyl) tetrahydro-2H-pyran-2-yl)-1H-1,2,3-triazol-4-yl)amino)propylthio)propane-1,2-diyl dipalmitate (30g): di and tri lipidated cysteine alkyne (Scheme-1, 11) (0.01 mmol) was stirred in tertiary butanol and water (1:1 mixture, 5 ml) to which copper sulfate (0.042 mmol) and sodium ascorbate (0.042 mmol) were added and the reaction mixture was stirred at RT, after 15 minutes, sugar azide (0.021 g, 0.01) was added and the mixture was allowed to stir for 8 hours at RT. Tertiary butanol was evaporated under reduced pressure, diluted with CHCl₃ and water. The organic layer was separated and aqueous layer extracted with CHCl₃ (2×100 ml). The combined organic layers were dried over Na₂SO₄ and evaporated under reduced pressure to afford the crude product which was purified by column chromatography (10% MeOH: CHCl$_3$) to afford pure product as white solid (78%).

$^1$H NMR (300 MHz, DMSO-d$_6$): 0.85 (t, J=6.4 Hz, 9H), 1.16-1.31 (m, 72H), 1.44-1.54 (m, 6H), 2.25 (t, J=7.1 Hz, 6H), 2.66-2.76 (m, 1H), 2.81 (dd, J=3.8, 5.43 Hz, 2H), 3.01 (dd, J=3.9, 4.2 Hz, 1H), 3.52-3.61 (m, 2H), 4.27 (d, J=11.7 Hz, 1H), 4.39 (dd, J=5.3, 5.6 Hz, 3H), 4.5 (br, 1H), 4.59 (t, J=5.6 Hz, 1H), 5.01 (dd, J=5.1, 5.3 Hz, 1H), 5.88 (d, J=3.9 Hz, 1H), 8.04 (s, 1H), 8.8 (q, I=4.4 Hz, 1H), 9.68 (dd, J=7.4, 7.7 Hz, 1H). MS (ESI): m/z 1175 [M+Na]$^+$.

Example 13

(2R)-3-((2S)-3-oxo-2-palmitamido-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dipalmitate (30h): di and tri lipidated cysteine alkyne (Scheme-1, 11) (0.01 mmol) was stirred in tertiary butanol and water(1:1 mixture, 5 ml) to which copper sulfate (0.042 mmol)and sodium ascorbate (0.042 mmol) were added and the reaction mixture was stirred at RT, after 15 minutes, sugar azide (0.021 g,0.01) was added and the mixture was allowed to stir for 8 hours at RT. Tertiary butanol was evaporated under reduced pressure, diluted with CHCl$_3$ and water. The organic layer was separated and aqueous layer extracted with CHCl$_3$ (2×100 ml). The combined organic layers were dried over Na$_2$SO$_4$ and evaporated under reduced pressure to afford the crude product which was purified by column chromatography (10% MeOH: CHCl$_3$) to afford pure product as white solid (90%).

$^1$H NMR (300 MHz, DMSO-d$_6$): 0.84 (t, J=6.7, Hz, 9H), 1.17-1.28 (m,72H),1.44-1.53 (dd, J=5.7, 6.7 Hz, 6H), 2.25 (t, J=7.3 Hz, 6H), 2.72 (dd, J=5.3, 7.7 Hz, 1H), 2.8 (ddd, J=3.1,5.1 Hz, 2H), 3.02 (ddd, J=3.3, 4.2, 4.4 Hz, 1H),3.43-3.57 (m, 3H), 4.04-4.11 (m,1H), 4.28 (dd, J=5.1,9.4 Hz, 2H), 4.34 (dd, 1=5.4 Hz, 1H), 4.4 (dd, J=5.7 Hz, 1H), 4.5 (m, 1H), 4.65 (dd, 1=3.8 Hz, 1H), 4.69 (t, J=5.6 Hz, 1H), 5.02 (d, J=5.3 Hz, 1H), 5.08(m, 1H),5.45 (d, J=9.1 Hz, 1H), 8.04 (s, 1H),8.78 (dd, J=5.3, 5.4 Hz, 1H), 9.68 (dd, J=7.4, 7.7 Hz, 1H). MS (ESI): m/z 1175[M+Na]$^+$.

Example 14

(2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl didodecanoate (27h): di and tri lipidated cysteine alkyne (Scheme-1, 11) (0.01 mmol) was stirred in tertiary butanol and water (1:1 mixture, 5 ml) to which copper sulfate (0.042 mmol)and sodium ascorbate (0.042 mmol) were added and the reaction mixture was stirred at RT, after 15 minutes, sugar azide (0.021 g, 0.01) was added and the mixture was allowed to stir for 8 hours at RT. Tertiary butanol was evaporated under reduced pressure, diluted with CHCl$_3$ and water. The organic layer was separated and aqueous layer extracted with CHCl$_3$ (2×100 ml). The combined organic layers were dried over Na$_2$SO$_4$ and evaporated under reduced pressure to afford the crude product which was purified by column chromatography (10% MeOH: CHCl$_3$) to afford pure product as white solid (91%).

$^1$H NMR (300 MHz, DMSO-d$_6$): 0.84 (t, J=6.7, Hz, 9H), 1.17-1.28 (m,48H), 1.44-1.53 (dd, J=5.7, 6.7 Hz, 6H), 2.25 (t, J=7.3 Hz, 6H), 2.72(dd, J=5.3,7.7 Hz, 1H), 2.8 (ddd, J=3.1,5.1 Hz, 2H), 3.02 (ddd, J=3.3, 4.2, 4.4 Hz, 1H),3.43-3.57 (m, 3H), 4.04-4.11 (m,1H), 4.28 (dd, J=5.1,9.4 Hz, 2H), 4.34 (dd, J=5.4 Hz, 1H), 4.4 (dd, J=5.7 Hz, 1H), 4.5 (m,1H), 4.65(dd, J=3.8 Hz, 1H), 4.69(t, J=5.6 Hz,1H), 5.02 (d, J=5.3 Hz,1H), 5.08(m, 1H),5.45 (d, J=9.1 Hz, 1H), 8.04 (s, 1H), 8.78 (dd, J=5.3, 5.4 Hz, 1H), 9.68 (dd, J=7.4, 7.7 Hz, 1H). MS (ESI): m/z 970[M+Na]$^+$.

Example 15

(2R)-3-((2S)-3-oxo-2-palmitamido-3-((1-(3,4,5-trihydroxy-6-(hydroxymethyl)tetrahydro-2H-pyran-2-yl)-1H-1,2,3-triazol-4-yl)amino)propylthio)propane-1,2-diyldipalmitate (30i): di and tri lipidated cysteine alkyne (Scheme-1, 11) (0.01 mmol) was stirred in tertiary butanol and water (1:1 mixture, 5 ml) to which copper sulfate (0.042 mmol)and sodium ascorbate (0.042 mmol) were added and the reaction mixture was stirred at RT, after 15 minutes, sugar azide (0.021 g, 0.01) was added and the mixture was allowed to stir for 8 hours at RT. Tertiary butanol was evaporated under reduced pressure, diluted with CHCl$_3$ and water. The organic layer was separated and aqueous layer extracted with CHCl$_3$ (2×100 ml). The combined organic layers were dried over Na$_2$SO$_4$ and evaporated under reduced pressure to afford the crude product which was purified by column chromatography (10% MeOH: CHCl$_3$) to afford pure product as white solid (85%).

$^1$H NMR (300 MHz, DMSO-d$_6$): 0.84 (t, J=6.2 Hz, 9H), 1.14-1.34 (m,72H),1.41-1.56 (m, 6H), 2.25 (t, J=6.9 Hz, 6H), 2.63-2.87 (m, 3H), 2.98-3.07 (dd, J=4.5, 3.7 Hz, 1H), 3.16 (d, J=5.2 Hz,1H),3.85-3.95(m, 2H),4.03-4.63(m, 6H), 4.71(d, J=4.3, 1H), 4.95 (d, J=5.4 Hz, 1H),5.05-5.15 (br, 1H),5.27 (d, J=5.1 Hz, 1H),6.12 (d, J=5.8 Hz, 1H), 8.01 (s,1H), 8.8 (t, J=5.2 Hz, 1H), 9.69 (d, J=7.3 Hz,1H). MS (ESI): m/z 1175 [M+Na].

Example 16

(2R)-3-(((2S)-3-oxo-2-tridecanamido-3-((1-(3,4,5-trihydroxy-6-(hydroxymethyl)tetrahydro-2H-pyran-2-yl)-1H-1,2,3-triazol-4-yl)amino)propyl)thio)propane-1,2-diyl ditridecanoate (27i): di and tri lipidated cysteine alkyne (Scheme-1, 11) (0.01 mmol) was stirred in tertiary butanol and water (1:1 mixture, 5 ml) to which copper sulfate (0.042 mmol)and sodium ascorbate (0.042 mmol) were added and the reaction mixture was stirred at RT, after 15 minutes, sugar azide (0.021 g,0.01) was added and the mixture was allowed to stir for 8 hours at RT. Tertiary butanol was evaporated under reduced pressure, diluted with CHCl$_3$ and water. The organic layer was separated and aqueous layer extracted with CHCl$_3$ (2×100 ml). The combined organic layers were dried over Na$_2$SO$_4$ and evaporated under reduced pressure to afford the crude product which was purified by column chromatography (10% MeOH: CHCl$_3$) to afford pure product as white solid (89%).

$^1$H NMR (300 MHz, DMSO-d$_6$): 0.84 (t, J=6.2 Hz, 9H), 1.14-1.34 (m,54H),1.41-1.56 (m, 6H), 2.25 (t, J=6.9 Hz, 6H), 2.63-2.87 (m, 3H), 2.98-3.07 (dd, J=4.5, 3.7 Hz, 1H), 3.16 (d, J=5.2 Hz, 1H), 3.85-3.95(m,2H),4.03-4.63(m, 6H), 4.71(d, J=4.3,1H), 4.95 (d, J=5.4 Hz, 1H),5.05-5.15 (br,1H), 5.27 (d, J=5.1 Hz, 1H),6.12 (d, J=5.8 Hz, 1H), 8.01 (s, 1H), 8.8 (t, J=5.2 Hz, 1H), 9.69 (d, J=7.3 Hz, 1H). MS (ESI): m/z 1012 [M+Na].

Example 17

(2R)-3-((2S)-3-oxo-2-palmitamido-3-((1-((3,4,5,6-tetrahydroxytetrahydro-2H-pyran-2-yl)methyl)-1H-1,2,3-triazol-4-yl)amino)propylthio)propane-1,2-diyl dipalmitate (30j): di and tri lipidated cysteine alkyne (Scheme-1, 11) (0.1 g, 0.01 mmol) was stirred in tertiary butanol and water (1:1 mixture, 5ml) to which copper sulfate (0.042 mmol) and sodium ascorbate (0.042 mmol) were added and the reaction mixture was stirred at RT, after 15 minutes, sugar azide (0.021 g, 0.01) was added and the mixture was allowed to stir for 8 hours at RT. Tertiary butanol was evaporated under reduced pressure, diluted with CHCl$_3$ and water. The organic layer was separated and aqueous layer extracted with CHCl$_3$ (2×100 ml). The combined organic layers were dried over Na$_2$SO$_4$ and evaporated under reduced pressure to afford the crude product which was purified by column chromatography (10% MeOH: CHCl$_3$) to afford pure product as white solid (80%).

$^1$H NMR (300 MHz, DMSO-d$_6$): 0.83 (t, J=5,6 Hz, 9H), 1.1-1.34 (m, 72H), 1.38-1.53 (m, 6H), 2.23 (t, J=6.8 Hz, 6H), 2.62-2.84 (m, 3H), 2.9 (dd, J=3.1, 4.1 Hz, 1H), 3.47-3.67 (m, 2H), 3.82 (m, 1H), 4.07 (q, J=6.9 Hz, 1H), 4.22-4.11 (m, 5H), 4.62 (d, J=4.7 Hz, 1H), 4.7-4.8 (dd, J=3.9, 1H), 4.83-4.85 (m, 1H), 5.08 (m, 2H), 6.2 (d, J=4.7 Hz, 1H), 6.59 (d, J=6.7 Hz, 1H), 7.86 (s, 1H), 8.7 (m, 2H). MS (ESI): m/z 1175 [M+Na]$^+$.

Example 18

(2R)-3-(((2S)-3-oxo-2-tetradecanamido-3-((1-((3,4,5,6-tetrahydroxytetrahydro-2H-pyran-2-yl)methyl)-1H-1,2,3-triazol-4-yl)amino)propyl)thio)propane-1,2-diyl ditetradecanoate (28j): di and tri lipidated cysteine alkyne (Scheme-1, 11) (0.01 mmol) was stirred in tertiary butanol and water (1:1 mixture, 5 ml) to which copper sulfate (0.042 mmol) and sodium ascorbate (0.042 mmol) were added and the reaction mixture was stirred at RT, after 15 minutes, sugar azide (0.021 g, 0.01) was added and the mixture was allowed to stir for 8 hours at RT. Tertiary butanol was evaporated under reduced pressure, diluted with CHCl$_3$ and water. The organic layer was separated and aqueous layer extracted with CHCl$_3$ (2×100 ml). The combined organic layers were dried over Na$_2$SO$_4$ and evaporated under reduced pressure to afford the crude product which was purified by column chromatography (10% MeOH: CHCl$_3$) to afford pure product as white solid (88%).

$^1$H NMR (300 MHz, DMSO-d$_6$): 0.83 (t, J=5.6 Hz, 9H), 1.1-1.34 (m, 60H), 1.38-1.53 (m, 6H), 2.23 (t, J=6.8 Hz, 6H), 2.62-2.84 (m, 3H), 2.9 (dd, J=3.1, 4.1 Hz, 1H), 3.47-3.67 (m, 2H), 3.82 (m, 1H), 4.07 (q, J=6.9 Hz, 1H), 4.22-4.11 (m, 5H), 4.62 (d, J=4.7 Hz, 1H), 4.7-4.8 (dd, J=3.9, 1H), 4.83-4.85 (m, 1H), 5.08 (m, 2H), 6.2 (d, J=4.7 Hz, 1H), 6.59 (d, J=6.7 Hz, 1H), 7.86 (s, 1H), 8.7 (m, 2H). MS (ESI): m/z 1054 [M+Na]$^+$.

Example 19

(2R)-3-((2S)-3-((1-((2R)-3,4-dihydroxy-6-(hydroxymethyl)-5-(3,4,5-trihydroxy-6-hydroxymethyl)tetrahydro-2H-pyran-2-yloxy)tetrahydro-2H-pyran-2-yl)-1H-1,2,3-triazol-4-yl)amino)-3-oxo-2-palmitamidopropylthio)propane-1,2-diyl dipalmitate(30k): di and tri lipidated cysteine alkyne (Scheme-1, 11) (0.01 mmol) was stirred in tertiary butanol and water (1:1 mixture, 5 ml) to which copper sulfate (0.042 mmol) and sodium ascorbate (0.042 mmol) were added and the reaction mixture was stirred at RT, after 15 minutes, sugar azide (0.021 g, 0.01) was added and the mixture was allowed to stir for 8 hours at RT. Tertiary butanol was evaporated under reduced pressure, diluted with CHCl$_3$ and water. The organic layer was separated and aqueous layer extracted with CHCl$_3$ (2×100 ml). The combined organic layers were dried over Na$_2$SO$_4$ and evaporated under reduced pressure to afford the crude product which was purified by column chromatography (10% MeOH: CHCl$_3$) to afford pure product as white solid 75%).

$^1$H NMR (300 MHz, DMSO-d$_6$): 0.84 (t, J=6.7 Hz, 9H), 1.16-1.29 (m, 72H), 1.44-1.53 (m, 6H), 2.25 (t, J=6.7, 7.1 Hz, 6H), 2.66-2.84 (m, 3H), 2.97-3.06 (ddd, J=4.4, 4.5 Hz, 1H), 3.58 (dd, J=3.9-4.4 Hz, 1H), 3.66 (m, 2H), 3.95 (m, 1H), 4.0 (s, 1H), 4.08 (m, 1H), 4.27 (dd, J=2.5 Hz, 1H), 4.31-4.41 (m, 5H), 4.49 (br, 1H), 4.91 (d, J=6.1 Hz, 1H), 5.08 (dd, J=1.1, 1.3 Hz, 2H), 5.16 (dd, J=3.8 Hz, 1H), 5.6 (d, J=9.1 Hz, 1H), 8.05 (s 1H), 8.78 (dd, J=3.3, 3.5 Hz, 1H), 9.67 (dd, J=4.7, 4.8 Hz, 1H). MS (ESI): m/z 1337 [M+Na]$^+$.

Example 20

(2R)-3-(((2S)-3-((1-((2R)-3,4-dihydroxy-6-(hydroxymethyl)-5-((3,4,5-trihydroxy-6-(hydroxymethyl)tetrahydro-2H-pyran-2-yl)oxy)tetrahydro-2H-pyran-2-yl)-1H-1,2,3-triazol-4-yl)amino)-3-oxo-2-pentadecanamidopropyl)thio) propane-1,2-diyl dipentadecanoate (29k): di and tri lipidated cysteine alkyne (Scheme-1, 11) (0.01 mmol) was stirred in tertiary butanol and water (1:1 mixture, 5 ml) to which copper sulfate (0.042 mmol) and sodium ascorbate (0.042 mmol) were added and the reaction mixture was stirred at RT, after 15 minutes, sugar azide (0.021 g, 0.01) was added and the mixture was allowed to stir for 8 hours at RT. Tertiary butanol was evaporated under reduced pressure, diluted with CHCl$_3$ and water. The organic layer was separated and aqueous layer extracted with CHCl$_3$ (2×100 ml). The combined organic layers were dried over Na$_2$SO$_4$ and evaporated under reduced pressure to afford the crude product which was purified by column chromatography (10% MeOH: CHCl$_3$) to afford pure product as white solid (82%).

$^1$H NMR (300 MHz, DMSO-d$_6$): 0.84 (t, J=6.7 Hz, 9H), 1.16-1.29 (m, 66H), 1.44-1.53 (m, 6H), 2.25 (t, J=6.7, 7.1 Hz, 6H), 2.66-2.84 (m, 3H), 2.97-3.06 (ddd, J=4.4, 4.5 Hz, 1H), 3.58 (dd, J=3.9-4.4 Hz, 1H), 3.66 (m, 2H), 3.95 (m, 1H), 4.0 (s, 1H), 4.08 (m, 1H), 4.27 (dd, J=2.5 Hz, 1H), 4.31-4.41 (m, 5H), 4.49 (br, 1H), 4.91 (d, J=6.1 Hz, 1H), 5.08 (dd, J=1.1, 1.3 Hz, 2H), 5.16 (dd, J=3.8 Hz, 1H), 5.6 (d, J=9.1 Hz, 1H), 8.05 (s 1H), 8.78 (dd, J=3.3, 3.5 Hz, 1H), 9.67 (dd, J=4.7, 4.8 Hz, 1H). MS (ESI): m/z 1258 [M+Na]$^+$.

Example 21

(2R)-3-((2S)-3-((1-((2R)-3,4-dihydroxy-6-(hydroxymethyl)-5-(3,4,5-trihydroxy-6-hydroxymethyl)tetrahydro-2H-pyran-2-yloxy)tetrahydro-2H-pyran-2-yl)-1H-1,2,3-triazol-4-yl)amino)-3-oxo-2-palmitamidopropylthio)propane-1,2-diyldipalmitate (30l): di and tri lipidated cysteine alkyne (Scheme-1, 11) (0.01 mmol) was stirred in tertiary butanol and water(1:1 mixture, 5 ml) to which copper sulfate (0.042 mmol) and sodium ascorbate (0.042 mmol) were added and the reaction mixture was stirred at RT, after 15 minutes, sugar azide (0.021 g, 0.01) was added and the mixture was allowed to stir for 8 hours at RT. Tertiary butanol was evaporated under reduced pressure, diluted with CHCl$_3$ and water. The organic layer was separated and aqueous layer extracted with CHCl$_3$ (2×100 ml). The combined organic layers were dried over Na$_2$SO$_4$ and evaporated under reduced pressure to afford the crude product which was purified by column chromatography (10% MeOH: CHCl$_3$) to afford pure product as white solid (78%).

$^1$H NMR (300 MHz, DMSO-d$_6$): 0.84 (t, J=6.2 Hz, 9H), 1.15-1.33 (m, 72H), 1.42-1.56 (m, 6H), 2.25 (t, J=6.9 Hz, 6H), 2.65-2.84 (m, 3H), 2.97-3.03 (m, 1H), 3.7-3.85 (m, 3H), 4.03-4.13 (m, 1H), 4.67 (s, 2H), 4.81 (d, J=4.72 Hz, 1H), 4.9 (s, 1H), 5.04-5.18 (m, 3H), 5.55 (d, J=5.28 Hz, 1H), 5.6 (d, J=9.44 Hz, 1H), 8.09 (s, 1H), 8.8 (dd, J=3.96, 7.17 Hz, 1H), 9.6 (s, 1H). MS (ESI): m/z 1337 [M+Na]$_+$.

Example 22

(2R)-3-(((2S)-2-amino-3-((1-((2R)-3,4-dihydroxy-6-(hydroxymethyl)-5-((3,4,5-trihydroxy-6-(hydroxymethyl)tetrahydro-2H-pyran-2-yl)oxy)tetrahydro-2H-pyran-2-yl)-1H-1,2,3-triazol-4-yl)amino)-3-oxopropyl)thio)propane-1,2-diyl dipalmitate (17l): di and tri lipidated cysteine alkyne (Scheme-1, 11) (0.01 mmol) was stirred in tertiary butanol and water (1:1 mixture, 5 ml) to which copper sulfate (0.042 mmol) and sodium ascorbate (0.042 mmol) were added and the reaction mixture was stirred at RT, after 15 minutes, sugar azide (0.021 g,0.01) was added and the mixture was allowed to stir for 8 hours at RT. Tertiary butanol was evaporated under reduced pressure, diluted with CHCl$_3$ and water. The organic layer was separated and aqueous layer extracted with CHCl$_3$ (2×100 ml). The combined organic layers were dried over Na$_2$SO$_4$ and evaporated under reduced pressure to afford the crude product which was purified by column chromatography (10% MeOH: CHCl$_3$) to afford pure product as white solid (84%).

$^1$H NMR (300 MHz, DMSO-d$_6$): 0.84 (t, J=6.2 Hz, 6H), 1.15-1.33 (m, 48H), 1.42-1.56 (m, 4H), 2.25 (t, J=6.9 Hz, 4H), 2.65-2.84 (m, 3H), 2.97-3.03 (m, 1H), 3.7-3.85 (m, 3H), 4.03-4.13 (m, 1H), 4.67 (s, 2H), 4.81(d, J=4.72 Hz, 1H), 4.9 (s, 1H), 5.04-5.18 (m, 3H), 5.55 (d, J=5.28 Hz, 1H), 5.6 (d, J=9.44 Hz, 1H), 8.09 (s, 1H), 8.8 (dd, J=3.96, 7.17 Hz, 1H), 9.6 (s, 1H). MS (ESI): m/z 1062 [M+Na]$^+$.

Biological Activity: The following examples illustrate the immune response of the compounds covered in this invention in conjunction with an external antigens, with or without any formulation, but they are not intended to limit the scope of the present claims. It should be appreciated that a person of ordinary skill in the art may modify and/or improve the following examples within the spirit and scope of the present invention. Thus, vaccine was formulated with experimental weak antigen ova or other appropriate antigens derived from human infections caused by bacteria, virus or protozoa, with various adjuvants like Pam3Csk4 and their analogues covered in this invention. The adjuvanticity induced by each of the vaccine is determined by antibody titre, cytokine production and proliferation of immune cells.

Example 23

13.1 Preparation and immunization of the vaccine: Male BALB/c mice (Procured from laboratory animal facility of National Institute of Nutrition, Hyderabad, IAEC No. IICT/Bio/fox/PG/1/02/2013) were immunized subcutaneously with different groups according to various concentrations of conjugates covered in examples 1-12, preferably 2 to 80 µg/dose, more preferably 6 to 50 µg/dose, most preferably 8 to 40 µg/dose, along with PBS (car no. TS1006, Himedia) and antigen control. A booster dose was given on 14$^{th}$ day and sacrificed 2 weeks after booster.

1.2 Analysis of Immune Response 1.2.1 Proliferation of immune cells: Splenocytes were seeded into 96 well flat bottom microtiter plates having 1×10$^5$ cells/well in complete RPMI-1640 medium (cat no. AT028-1L, Himedia). Plates were incubated at 37° C., with 5% CO$_2$ incubator. After 48 h of incubation 20 µl of Triazolyl blue Tetrazolium Bromide (MTT) (cat no. M2128, Sigma-Aldrich. St. Louis, Mo.) solution (5 mg/mL) was added to each well, incubated for next 4 h. Untransformed MTT was removed from each well by aspirating the supernatant (180 µL) and replaced with DMSO (Sigma-Aldrich, St. Louis, Mo.). The absorbance was read at 630 nm after 15 min.

Table-1 shows the OVA(cat no. A5503. Sigma-Aldrich. St. Louis, Mo.) stimulated splenocyte proliferation in the mice immunized with conjugates covered in Example 1-12 which was significantly higher than that in the OVA and Pam$_3$CSK$_4$ group (Vaccigrade Pam3CysSK4, cat no. vac-pms, Invivogen, USA). All triazolyl adjuvant conjugates induced splenocyte proliferation responses at the dose of 2-80 µg.

TABLE 1

| Test compounds | Splenocyte proliferation |
|---|---|
| Standard (VacciGrade Pam3Cys) control | 200-350 |
| various concentrations conjugates | 250-400 |

1.2.2 Cytokine expression on immunization: ELISA was carried out by Opti Elisa Kit (cat no. 560485, BD biosciences, USA). Briefly, 96-Well plates were coated with capture antibody dissolved in coating buffer. Wells were blocked with PBS containing 0.05% Tween-20 for 1h at RT. After blocking, 100 µL/well of supernatant was added and incubated for overnight at 4° C. After washing, biotinylated secondary antibody was added along with enzyme. Plates were incubated for 1h at RT. Then plates were washed and substrate solution was added. The reaction was stopped and the absorbance was measured at 450 nm in ELISA reader (BioTek-Elx800). Table-2 shows the effect of conjugates on the release of selected cytokines viz IL-2, IL-4, IL-12, IFN-γ and TNF-α. Results indicate that few analogues stimulated Th1 and remaining Th2 cytokines in a dose-dependent manner.

TABLE 2

Serum cytokines results (Conc (pg/mL))

| | Test compounds | | | | | |
|---|---|---|---|---|---|---|
| | IL-2 | IL-12 | IFN-γ | TNF-α | IL-10 | IL-6 |
| Standard (VacciGrade Pam3Cys) control | 100-150 | 80-140 | 100-140 | 150-200 | 180-220 | 100-120 |
| various concentrations conjugates | 200-300 | 250-300 | 300-350 | 200-250 | 300-350 | 400-450 |

1.2.2 Antibody titre against OVA antigen: From the immunized mice retro-orbital sampling or retro-orbital blood was collected on 14th and 28th day before sacrifice. Serum was separated by centrifugation at 12,500 rpm for 5 min. Transferred to a clean centrifuge tube and store at −80 until used. The plates were coated with OVA (1 µg/well) in carbonate buffer. Plates were incubated at 4° C., overnight. They were then washed 3 times with PBS/Tween, and non-specific binding sites were blocked by adding 200 µl of blocking solution. Plates were incubated at room temperature for 1 h. Then 3 times wash is done, diluted standards and samples to desired concentrations in blocking solution were added to the plates. Incubate at 37° C. for 1 h or at 4° C., overnight. Plates were washed 3 times with PBS/Tween. Avidin-Horseradish Peroxidase (Av-HRP, cat no. 45210, Biolegend, USA) was diluted and added. Incubated at room temperature for 30 min. Plates were washed 3 times with PBS/Tween. Substrate was added, mix equal volumes of TMB Reagent A and B(cat no. 421101, Biolegend, USA) immediately prior to use. Plates were incubated at room temperature (4-30 min) for color development. Color reaction was stopped by adding 50 µl of stop solution. Optical density (OD) was read at 450 nm.

1.2.3 Isotypes of antigen specific antibody: The plates were coated with diluted unlabeled capture antibody to a final concentration of 0.5-8 µg/ml. Plates were incubated at 4° C. overnight. They were then washed 3 times with PBS/Tween, and non-specific binding sites were blocked by adding 200 µl of blocking solution. Plates were incubated at room temperature for 1 h. Washing is done thrice, diluted standards and samples to desire concentrations in blocking solution were added to the plates. Incubate at room temperature for 2-4 h or at 4° C., overnight. Plates were washed 3 times with PBS/Tween. Detection antibodies were added 0.25-2 µg/ml in blocking buffer, followed by incubation at room temperature for 1 h. Plates were washed 3 times with PBS/Tween. Avidin-Horseradish Peroxidase (Av-HRP) was diluted and added. Incubated at room temperature for 30 min. Plates were washed 5 times with PBS/Tween. Substrate was added, mix equal volumes of TMB Reagent A and B immediately prior to use. Plates were incubated at room temperature (0.4-30 min) for color development. Color reaction was stopped by adding 50 µl of stop solution. Optical density (OD) was read at 450 nm.

Table-3 shows the serum anti-OVA IgG titer. OVA specific IgG(Sandwich ELISA antibody estimation kit, cat no., 405306, Biolegend, USA) was assayed by indirect ELISA and titers obtained after booster immunization reveals that the production of anti-OVA antibodies was strongly enhanced in mice treated with a various concentrations of conjugates (2-80 µg/mice) in comparison with OVA alone. Table-3 also shows the total IgG1 (Jackson Immunoresearch cat no. 115-035-205)and IgG2a (Jackson Immunoresearch cat no. 115-036-206)antibody titers in the serum. IgG1 and IgG2a were measured by sandwich ELISA. The serum IgG, IgG1 and IgG2a titer in OVA immunized mice was significantly increased by conjugates (2-80 µg). The adjuvant conjugates (2-80 µg) significantly enhanced the serum IgG1 titers in OVA-immunized mice with more significant enhancements in serum IgG2a titers with these adjuvant conjugates (2-80 µg) immunized mice compared with OVA alone group (Table-3) indicating powerful Th1 activation leading to cell mediated immune response induced by these conjugates in conjunction with ovalbumin.

TABLE 3

| Test compounds | 28th day | | |
|---|---|---|---|
| | IgG | IgG1 | IgG 2a |
| PBS control | 400-800 | 400-800 | 400-800 |
| OVA control | 6400-12800 | 6400-25600 | 6400-12800 |
| Standard (VacciGrade Pam3Cys) control | 102400-819200 | 102400-1638400 | 102400-3276800 |
| various concentrations conjugates | 51200-409600 | 102400-3276800 | 102400-6553600 |

Example 24

Stimulation of adjuvanticity of the compounds with HBsAg antigen:

Vaccine was formulated with Hepatitis B antigen (HBsAg, cat. No HBS-870-c, ProspecBio, Israel))alone or with various adjuvants like Pam3CSK4 and their analogues. The adjuvanticity induced by each of the vaccine is determined by antibody titre, cytokine production and proliferation of immune cells.

2.1 Preparation and Immunization of the Vaccine

Male BALB/c mice were immunized with different groups according to various concentrations of (conjugates) preferably 2 to 80 µg/dose, more preferably 6 to 50 µg/dose, most preferably 8 to 40 µg/dose, along with PBS and HBsAg antigen control. A booster dose was given on 14$^{th}$ day and sacrificed 2 weeks after booster.

2.2 Analysis of Immune Response 2.2.1 Proliferation of immune cells: Splenocyte proliferation was measured by the same method as described in Example 13 except that HBsAg antigen. Table-4 shows the HBsAg stimulated splenocyte proliferation in the mice immunized with conjugates was significantly higher than that in the HBsAg and Pam3CSK4 group. Conjugates induced splenocyte proliferation responses at the dose of 2-80 µg.

TABLE 4

| Test compounds | Splenocyte proliferation |
|---|---|
| Standard (VacciGrade Pam3Cys) control | 250-500 |
| various concentrations conjugates | 300-600 |

2.2.2 Cytokine expression on immunization: Cytokine expression was measured by the same method as described in the Example 13 except that HBsAg antigen.

Table-5 shows the effect of conjugates was tested on the release of selected cytokines including IL-2, IL-4, IL-12, IFN-γ and TNF-α by stimulated mouse spleen cells. Results indicate that the adjuvant conjugates 1-13 stimulated significantly Th1 and Th2 cytokines in a dose-dependent manner showing immune response polarized towards Th1 immunity.

TABLE 5

| | Serum cytokines results (Conc (pg/mL)) | | | | | |
|---|---|---|---|---|---|---|
| | Test compounds | | | | | |
| | IL-2 | IL-12 | IFN-γ | TNF-α | IL-10 | IL-6 |
| Standard (VacciGrade Pam3Cys) control | 250-300 | 150-250 | 250-325 | 275-400 | 325-475 | 250-295 |
| various concentrations conjugates | 350-450 | 350-500 | 650-700 | 375-450 | 600-700 | 800-950 |

2.2.3 Antibody titre against HBsAg antigen: Antibody titer was determined by the same method as described in the Example 13 except that HBsAg antigen. Table-6 shows the serum anti-HBsAg IgG titer. HBsAg specific IgG and subtype IgG1, IgG2a was assayed by indirect ELISA and titers obtained after booster immunization reveals that the production of anti-HBsAg antibodies was strongly enhanced in mice treated with a various concentrations of conjugates (2-80 µg/mice) in comparison with HBsAg alone.

Table—shows the total IgG, IgG1 and IgG2a antibody titers in the serum. Antibody titres IgG, IgG1 and IgG2a were measured by sandwich ELISA. The serum IgG (IgG1 and IgG2a) titer in HBsAg immunized mice was significantly increased by conjugates (2-80 μg). The adjuvant conjugates (2-80 μg) significantly enhanced the serum IgG1 titers in HBsAg-immunized mice and more significantly enhanced serum IgG2a titers (2-80 μg) when immunized mice compared with HBsAg alone group indicating pronounced Th1 activation with cell mediated immunity.

TABLE 6

| Test compounds | 28th day | | |
|---|---|---|---|
| | IgG | IgG1 | IgG 2a |
| PBS control | 400-800 | 400-800 | 400-800 |
| OVA control | 12800-51200 | 12800-102400 | 12800-51200 |
| Standard (VacciGrade Pam3Cys) control | 204800-819200 | 102400-409600 | 204800-3276800 |
| various concentrations conjugates | 102400-409600 | 102400-1638400 | 204800-6553600 |

2.2.4 Human TLR-2 reporter gene assays (NF-κB induction): The assay was performed as per the manufacturer's instructions. HEK-Blue™ hTLR2 cells (cat no. hkb-htlr2, Invivogen, USA, 25,000 cells per well) were harvested in HEK-Blue™ selection medium containing normocin treated with the compounds and the plate were incubated at 37° C. in 5% $CO_2$ for 24 h. SEAP (secreted embryonic alkaline phosphatase) can be observed with naked eye and determined using a spectrophotometer at 620-655 nm.

TABLE 7

| TLR Ligand activity | |
|---|---|
| Test compounds | SEAP Absorbance (655 nm) |
| Standard (VacciGrade Pam3Cys) control | 1.2-2 |
| various concentrations conjugates | 0.6-3 |

2.2.5 Immunophenotyping—Staining for extracellular markers: Staining was as per the manufacturer's protocol and run on a BD FACSVerse flow cytometer (cat nos. 557596, 553047, 560016 and 553723; BD Biosciences, USA). Compensation was established using BD Biosciences compensation beads. Post acquisition flow cytometry analysis was performed using FACS Suite software and data were represent in the mean fluorescence intensity values.

TABLE 8

| Immunophenotyping (MFI) | | | | |
|---|---|---|---|---|
| Test compounds | CD4 | CD8 | CD80 | CD86 | CD40 |
| Standard (VacciGrade Pam3Cys) control | 1400-3000 | 2000-4000 | 1600-2500 | 1200-2000 | 1000-2500 |
| various concentrations conjugates | 1400-3000 | 1800-5000 | 1500-3000 | 1600-1800 | 9000-3500 |

2.2.6 In vitro cytotoxicity evaluation by MTT assay: Rat kidney cell line NRK-49F (NCCS, Pune) was exposed to varying doses of test compounds in the range of 10 IM-100 IM, to determine the toxicity after 48 h of incubation. The colorimetric MTT assay was used to evaluate cell viability which is determined based on reduction of MTT to blue formazan crystals by the mitochondrial succinate dehydrogenase enzymes of viable cells.

TABLE 9

| Test compounds | % Viability |
|---|---|
| Standard (VacciGrade Pam3Cys) control | 95-100 |
| various concentrations conjugates | 95-100 |

2.2.7 Hemolytic assay: Different concentration of test compounds were tested with fixed volume concentration of rat RBCs. After incubation for 30 min the percentage of hemolysis was determined by comparing the absorbance (k=540 nm) of the supernatant with that of distilled water as positive control.

TABLE 10

| Test compounds | % Hemolysis |
|---|---|
| Standard (VacciGrade Pam3Cys) control | 2-5 |
| various concentrations conjugates | 0-5 |

ADVANTAGES OF THE INVENTION

1. The present invention provides new class of triazole tethered carbohydrate—di and tri lipidated cysteine conjugate useful as vaccine adjuvants.
2. The 1,2,3-Triazole-tethered carbohydrate—di and tri lipidated cysteine conjugates as TLR-2 agonists covered in this invention exhibited significant vaccine adjuvant activity with Th1 activation, useful for the development of powerful vaccines against various infectious diseases.
3. The invention involves cationic 1,2,3-triazole in conjunction with suitable hydrophilic carbohydrate entities as replacement of polycationic peptide in conventional TLR specific adjuvants, making the conjugates amphiphylic with high adjuvant activity compared to the peptide based TLR adjuvant.
4, triazolyl cysteine adjuvants claimed here show high antibody response with an external antigen and also evoke Th1 activation as revealed by the expression of Th1 cytokines and IgG2a/IgG1 ratio.
5. It also provides a method for the preparation of vaccine adjuvants.

What is claimed is:
1. A vaccine adjuvant conjugate of Formula (1)

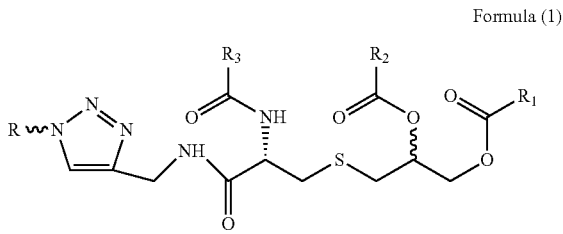

Formula (1)

wherein
R is selected from the group consisting of a pyranose or furanose monosaccharide, pyranose or furanose disaccharides, and di- or polyhydroxy-alkyl, wherein the monosaccharide or disaccharide is linked to the 1,2,3-triazolyl methyl amine moiety through alpha or beta linkage;

$R_1$ and $R_2$ are selected from the group consisting of alkyl ($C_4$-$C_{18}$), alkenyl ($C_4$-$C_{18}$), alkynyl ($C_4$-$C_{18}$) either linear or branched, arylalkyl ($C_4$-$C_{18}$), cycloalkyl ($C_4$-$C_{18}$), and triterpinyl($C_4$-$C_{18}$) lipid entity;

$R_3$ is selected from the group consisting of hydrogen, alkyl ($C_4$-$C_{18}$), alkenyl ($C_4$-$C_{18}$), alkynyl ($C_4$-$C_{18}$) either linear or branched, arylalkyl ($C_4$-$C_{18}$), cycloalkyl ($C_4$-$C_{18}$), and triterpinyl($C_4$-$C_{18}$) lipid.

2. The vaccine adjuvant conjugate as claimed in claim 1 that is selected from the group consisting of:

(R)-3-((S)-2-amino-3-((1-((R)-2,3-dihydroxypropyl)-1H-1,2,3-triazol-4-yl)amino)-3-oxopropylthio)propane-1,2-diyl dihexanoate (7a);

(2R)-3-((2S)-2-amino-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl dihexanoate (7b);

(2R)-3-((2S)-2-amino-3-((1-((2S)-2-hydroxy-2-((3S,4S)-3,4,5-trihydroxytetrahydrofuran-2-yl)ethyl)-1H-1,2,3-triazol-4-yl)amino)-3-oxopropylthio)propane-1,2-diyl dihexanoate (7c);

(R)-3-((S)-2-amino-3-oxo-3-((1-((2S,3S,4R,5R)-2,3,4,5,6-pentahydroxyhexyl)-1H-1,2,3-triazol-4-yl)amino)propylthio)propane-1,2-diyl dihexanoate (7d);

(2R)-3-((2S)-2-amino-3-((1-((2S,3R,4S)-3,4-dihydroxy-5-(hydroxymethyl)tetrahydrofuran-2-yl)-1H-1,2,3-triazol-4-yl)amino)-3-oxopropylthio)propane-1,2-diyl dihexanoate.(7e);

(2R)-3-((2S)-2-amino-3-((1-((2S,3S,4S)-3,4-dihydroxy-5-(hydroxymethyl)tetrahydrofuran-2-yl)-1H-1,2,3-triazol-4-yl)amino)-3-oxopropylthio)propane-1,2-diyl dihexanoate (7f);

(2R)-3-((2S)-2-amino-3-oxo-3-((1-((2R)-3,4,5-trihydroxy-6-(hydroxymethyl)tetrahydro 2H-pyran-2-yl)-1H-1,2,3-triazol-4-yl)amino)propylthio)propane-1,2-diyl dihexanoate (7g);

(2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dihexanoate (7h);

(2R)-3-((2S)-2-amino-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl dihexanoate (7i);

(2R)-3-((2S)-2-amino-3-oxo-3-((1-((3,4,5,6-tetrahydroxytetrahydro-2H-pyran-2-yl)methyl)-1H-1,2,3-triazol-4-yl)amino)propylthio)propane-1,2-diyl dihexanoate (7j);

(2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl dihexanoate (7k);

(2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl dihexanoate (7l);

(R)-3-((S)-2-amino-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl diheptanoate (7m);

(R)-3-((S)-2-amino-3-((1-((R)-2,3-dihydroxypropyl)-1H-1,2,3-triazol-4-yl)methylamino)-3-oxopropylthio)propane-1,2-diyl diheptanoate (8a);

(2R)-3-((2S)-2-amino-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl diheptanoate (8b);

(2R)-3-((2S)-2-amino-3-((1-((2S)-2-hydroxy-2-((3S,4S)-3,4,5-trihydroxytetrahydrofuran-2-yl)ethyl)-1H-1,2,3-triazol-4-yl)amino)-3-oxopropylthio)propane-1,2-diyl diheptanoate(8c);

(R)-3-((S)-2-amino-3-oxo-3-((1-((2S,3S,4R,5R)-2,3,4,5,6-pentahydroxyhexyl)-1H-1,2,3-triazol-4-yl)amino)propylthio)propane-1,2-diyl diheptanoate (8d);

(2R)-3-((2S)-2-amino-3-((1-((2S,3R,4S)-3,4-dihydroxy-5-(hydroxymethyl)tetrahydrofuran-2-yl)-1H-1,2,3-triazol-4-yl)amino)-3-oxopropylthio)propane-1,2-diyl diheptanoate (8e);

(2R)-3-((2S)-2-amino-3-((1-((2S,3S,4S)-3,4-dihydroxy-5-(hydroxymethyl)tetrahydrofuran-2-yl)-1H-1,2,3-triazol-4-yl)amino)-3-oxopropylthio)propane-1,2-diyl diheptanoate (8f);

(2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl diheptanoate (8g);

(2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl diheptanoate (8h);

(2R)-3-((2S)-2-amino-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl diheptanoate (8i);

(2R)-3-((2S)-2-amino-3-oxo-3-((1-((3,4,5,6-tetrahydroxytetrahydro-2H-pyran-2-yl)methyl)-1H-1,2,3-triazol-4-yl)amino)propylthio)propane-1,2-diyl diheptanoate (8j);

(2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl diheptanoate (8k);

(2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl diheptanoate (8l);

(R)-3-((S)-2-amino-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl diheptanoate (8m);

(R)-3-((S)-2-amino-3-((1-((R)-2,3-dihydroxypropyl)-1H-1,2,3-triazol-4-yl)amino)-3-oxopropylthio)propane-1,2-diyl dioctanoate (9a);

(2R)-3-((2S)-2-amino-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl dioctanoate (9b);

(2R)-3-((2S)-2-amino-3-((1-((2S)-2-hydroxy-2-((3S,4S)-3,4,5-trihydroxytetrahydrofuran-2-yl)ethyl)-1H-1,2,3-triazol-4-yl)amino)-3-oxopropylthio)propane-1,2-diyl dioctanoate (9c);

(R)-3-((S)-2-amino-3-oxo-3-((1-((2S,3S,4R,5R)-2,3,4,5,6-pentahydroxyhexyl)-1H-1,2,3-triazol-4-yl)amino)propylthio)propane-1,2-diyl dioctanoate (9d);

(2R)-3-((2S)-2-amino-3-((1-((2S,3R,4S)-3,4-dihydroxy-5-(hydroxymethyl)tetrahydrofuran-2-yl)-1H-1,2,3-triazol-4-yl)amino)-3-oxopropylthio)propane-1,2-diyl dioctanoate (9e);

(2R)-3-((2S)-2-amino-3-((1-((2S,3S,4S)-3,4-dihydroxy-5-(hydroxymethyl)tetrahydrofuran-2-yl)-1H-1,2,3-triazol-4-yl)amino)-3-oxopropylthio)propane-1,2-diyl dioctanoate (9f);

(2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dioctanoate (9g);

(2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dioctanoate (9h);

(2R)-3-((2S)-2-amino-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl dioctanoate (9i);

(2R)-3-((2S)-2-amino-3-oxo-3-((1-((3,4,5,6-tetrahydroxytetrahydro-2H-pyran-2-yl)methyl)-1H-1,2,3-triazol-4-yl)amino)propylthio)propane-1,2-diyl dioctanoate (9j);

(2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl dioctanoate (9k);

(2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl dioctanoate (9l);

(R)-3-((S)-2-amino-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl dioctanoate (9m);

(R)-3-((S)-2-amino-3-((1-((R)-2,3-dihydroxypropyl)-1H-1,2,3-triazol-4-yl)amino)-3-oxopropylthio)propane-1,2-diyl dinonanoate (10a);

(2R)-3-((2S)-2-amino-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl dinonanoate (10b);

(2R)-3-((2S)-2-amino-3-((1-((2S)-2-hydroxy-2-((3S,4S)-3,4,5-trihydroxytetrahydrofuran-2-yl)ethyl)-1H-1,2,3-triazol-4-yl)amino)-3-oxopropylthio)propane-1,2-diyl dinonanoate (10c);

(R)-3-((S)-2-amino-3-oxo-3-((1-((2S,3S,4R,5R)-2,3,4,5,6-pentahydroxyhexyl)-1H-1,2,3-triazol-4-yl)amino)propylthio)propane-1,2-diyl dinonanoate (10d);

(2R)-3-((2S)-2-amino-3-((1-((2S,3R,4S)-3,4-dihydroxy-5-(hydroxymethyl)tetrahydrofuran-2-yl)-1H-1,2,3-triazol-4-yl)amino)-3-oxopropylthio)propane-1,2-diyl dinonanoate (10e);

(2R)-3-((2S)-2-amino-3-((1-((2S,3S,4S)-3,4-dihydroxy-5-(hydroxymethyl)tetrahydrofuran-2-yl)-1H-1,2,3-triazol-4-yl)amino)-3-oxopropylthio)propane-1,2-diyl dinonanoate (10f);

(2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dinonanoate (10g);

(2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dinonanoate (10h);

(2R)-3-((2S)-2-amino-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl dinonanoate (10i);

(2R)-3-((2S)-2-amino-3-oxo-3-((1-((3,4,5,6-tetrahydroxytetrahydro-2H-pyran-2-yl)methyl)-1H-1,2,3-triazol-4-yl)amino)propylthio)propane-1,2-diyl dinonanoate (10j);

(2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl dinonanoate (10k);

(2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl dinonanoate (10l);

(R)-3-((S)-2-amino-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl dinonanoate (10m);

(R)-3-((S)-2-amino-3-((1-((R)-2,3-dihydroxypropyl)-1H-1,2,3-triazol-4-yl)amino)-3-oxopropylthio)propane-1,2-diyl bis(decanoate) (11a);

(2R)-3-((2S)-2-amino-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl bis(decanoate) (11b);

2R)-3-((2S)-2-amino-3-((1-((2S)-2-hydroxy-2-((3S,4S)-3,4,5-trihydroxytetrahydrofuran-2-yl)ethyl)-1H-1,2,3-triazol-4-yl)amino)-3-oxopropylthio)propane-1,2-diyl bis(decanoate) (11c);

(R)-3-((S)-2-amino-3-oxo-3-((1-((2S,3S,4R,5R)-2,3,4,5,6-pentahydroxyhexyl)-1H-1,2,3-triazol-4-yl)amino)propylthio)propane-1,2-diyl bis(decanoate) (11d);

(2R)-3-((2S)-2-amino-3-((1-((2S,3R,4S)-3,4-dihydroxy-5-(hydroxymethyl)tetrahydrofuran-2-yl)-1H-1,2,3-triazol-4-yl)amino)-3-oxopropylthio)propane-1,2-diyl bis(decanoate) (11e);

(2R)-3-((2S)-2-amino-3-((1-((2S,3S,4S)-3,4-dihydroxy-5-(hydroxymethyl)tetrahydrofuran-2-yl)-1H-1,2,3-triazol-4-yl)amino)-3-oxopropylthio)propane-1,2-diyl bis(decanoate) (11f);

(2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl bis(decanoate) (11g);

(2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl bis(decanoate) (11h);

(2R)-3-((2S)-2-amino-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl bis(decanoate) (11i);

(2R)-3-((2S)-2-amino-3-oxo-3-((1-((3,4,5,6-tetrahydroxytetrahydro-2H-pyran-2-yl)methyl)-1H-1,2,3-triazol-4-yl)amino)propylthio)propane-1,2-diyl bis(decanoate) (11j);

(2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2- yl)-1H-1,2,3-triazol-4-yl)amino)-3-oxopropylthio) propane-1,2-diyl bis(decanoate) (11k);

(2R)-3-((2S)-2-amino-3-((1-((2R)-3,4-dihydroxy-6-(hydroxymethyl)-5-(3,4,5-trihydroxy-6-(hydroxymethyl) tetrahydro-2H-pyran-2-yloxy)tetrahydro-2H-pyran-2-yl)-1H-1,2,3-triazol-4-yl)amino)-3-oxopropylthio) propane-1,2-diyl bis(decanoate) (11l);

(R)-3-((S)-2-amino-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl bis(decanoate) (11m);

(R)-3-((S)-2-amino-3-((1-((R)-2,3-dihydroxypropyl)-1H-1,2,3-triazol-4-yl)amino)-3-oxopropylthio)propane-1,2-diyl diundecanoate (12a);

(2R)-3-((2S)-2-amino-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyldiundecanoate (12b);

(2R)-3-((2S)-2-amino-3-((1-((2S)-2-hydroxy-2-((3S,4S)-3,4,5-trihydroxytetrahydrofuran-2-yl)ethyl)-1H-1,2,3-triazol-4-yl)amino)-3-oxopropylthio)propane-1,2-diyldiundecanoate (12c);

(R)-3-((S)-2-amino-3-oxo-3-((1-((2S,3S,4R,5R)-2,3,4,5,6-pentahydroxyhexyl)-1H-1,2,3-triazol-4-yl)amino) propylthio)propane-1,2-diyl diundecanoate (12d);

(2R)-3-((2S)-2-amino-3-((1-((2S,3R,4S)-3,4-dihydroxy-5-(hydroxymethyl)tetrahydrofuran-2-yl)-1H-1,2,3-triazol-4-yl)amino)-3-oxopropylthio)propane-1,2-diyl diundecanoate (12e);

(2R)-3-((2S)-2-amino-3-((1-((2S,3S,4S)-3,4-dihydroxy-5-(hydroxymethyl)tetrahydrofuran-2-yl)-1H-1,2,3-triazol-4-yl)amino)-3-oxopropylthio)propane-1,2-diyl diundecanoate (12f);

(2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl diundecanoate (12g);

(2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl diundecanoate (12h);

(2R)-3-((2S)-2-amino-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl diundecanoate (12i);

(2R)-3-((2S)-2-amino-3-oxo-3-((1-((3,4,5,6-tetrahydroxytetrahydro-2H-pyran-2-yl)methyl)-1H-1,2,3-triazol-4-yl)amino)propylthio)propane-1,2-diyl diundecanoate (12j);

(2R)-3-((2S)-2-amino-3-((1-((2R)-3,4-dihydroxy-6-(hydroxymethyl)-5-(3,4,5-trihydroxy-6-(hydroxymethyl) tetrahydro-2H-pyran-2-yloxy)tetrahydro-2H-pyran-2-yl)-1H-1,2,3-triazol-4-yl)amino)-3-oxopropylthio) propane-1,2-diyl diundecanoate (12k);

(2R)-3-((2S)-2-amino-3-((1-((2R)-3,4-dihydroxy-6-(hydroxymethyl)-5-(3,4,5-trihydroxy-6-(hydroxymethyl) tetrahydro-2H-pyran-2-yloxy)tetrahydro-2H-pyran-2-yl)-1H-1,2,3-triazol-4-yl)amino)-3-oxopropylthio) propane-1,2-diyl diundecanoate (12l);

(R)-3-((S)-2-amino-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl diundecanoate (12m);

(R)-3-((S)-2-amino-3-((1-((R)-2,3-dihydroxypropyl)-1H-1,2,3-triazol-4-yl)amino)-3-oxopropylthio)propane-1,2-diyl didodecanoate (13a);

(2R)-3-((2S)-2-amino-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl didodecanoate (13b);

(2R)-3-((2S)-2-amino-3-((1-((2S)-2-hydroxy-2-((3S,4S)-3,4,5-trihydroxytetrahydrofuran-2-yl)ethyl)-1H-1,2,3-triazol-4-yl)amino)-3-oxopropylthio)propane-1,2-diyl didodecanoate (13c);

(R)-3-((S)-2-amino-3-oxo-3-((1-((2S,3S,4R,5R)-2,3,4,5,6-pentahydroxyhexyl)-1H-1,2,3-triazol-4-yl)amino) propylthio)propane-1,2-diyl didodecanoate (13d);

(2R)-3-((2S)-2-amino-3-((1-((2S,3R,4S)-3,4-dihydroxy-5-(hydroxymethyl)tetrahydrofuran-2-yl)-1H-1,2,3-triazol-4-yl)amino)-3-oxopropylthio)propane-1,2-diyl didodecanoate (13e);

(2R)-3-((2S)-2-amino-3-((1-((2S,3S,4S)-3,4-dihydroxy-5-(hydroxymethyl)tetrahydrofuran-2-yl)-1H-1,2,3-triazol-4-yl)amino)-3-oxopropylthio)propane-1,2-diyl didodecanoate (13f);

(2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl didodecanoate (13g);

(2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl didodecanoate (13h);

(2R)-3-((2S)-2-amino-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl didodecanoate (13i);

(2R)-3-((2S)-2-amino-3-oxo-3-((1-((3,4,5,6-tetrahydroxytetrahydro-2H-pyran-2-yl)methyl)-1H-1,2,3-triazol-4-yl)amino)propylthio)propane-1,2-diyl didodecanoate (13j);

(2R)-3-((2S)-2-amino-3-((1-((2R)-3,4-dihydroxy-6-(hydroxymethyl)-5-(3,4,5-trihydroxy-6-(hydroxymethyl) tetrahydro-2H-pyran-2-yloxy)tetrahydro-2H-pyran-2-yl)-1H-1,2,3-triazol-4-yl)amino)-3-oxopropylthio) propane-1,2-diyl didodecanoate (13k);

(2R)-3-((2S)-2-amino-3-((1-((2R)-3,4-dihydroxy-6-(hydroxymethyl)-5-(3,4,5-trihydroxy-6-(hydroxymethyl) tetrahydro-2H-pyran-2-yloxy)tetrahydro-2H-pyran-2-yl)-1H-1,2,3-triazol-4-yl)amino)-3-oxopropylthio) propane-1,2-diyl didodecanoate (13l);

(R)-3-((S)-2-amino-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl didodecanoate (13m);

(R)-3-((S)-2-amino-3-((1-((R)-2,3-dihydroxypropyl)-1H-1,2,3-triazol-4-yl)amino)-3-oxopropylthio)propane-1,2-diyl ditridecanoate (14a);

(2R)-3-((2S)-2-amino-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl ditridecanoate (14b);

(2R)-3-((2S)-2-amino-3-((1-((2S)-2-hydroxy-2-((3S,4S)-3,4,5-trihydroxytetrahydrofuran-2-yl)ethyl)-1H-1,2,3-triazol-4-yl)amino)-3-oxopropylthio)propane-1,2-diyl ditridecanoate (14c);

(R)-3-((S)-2-amino-3-oxo-3-((1-((2S,3S,4R,5R)-2,3,4,5,6-pentahydroxyhexyl)-1H-1,2,3-triazol-4-yl)amino) propylthio)propane-1,2-diyl ditridecanoate (14d);

(2R)-3-((2S)-2-amino-3-((1-((2S,3R,4S)-3,4-dihydroxy-5-(hydroxymethyl)tetrahydrofuran-2-yl)-1H-1,2,3-triazol-4-yl)amino)-3-oxopropylthio)propane-1,2-diyl ditridecanoate (14e);

(2R)-3-((2S)-2-amino-3-((1-((2S,3S,4S)-3,4-dihydroxy-5-(hydroxymethyl)tetrahydrofuran-2-yl)-1H-1,2,3-triazol-4-yl)amino)-3-oxopropylthio)propane-1,2-diyl ditridecanoate (14f);

(2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl ditridecanoate (14g);

(2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl ditridecanoate (14h);

(2R)-3-((2S)-2-amino-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl ditridecanoate (14i);

(2R)-3-((2S)-2-amino-3-oxo-3-((1-((3,4,5,6-tetrahydroxytetrahydro-2H-pyran-2-yl)methyl)-1H-1,2,3-triazol-4-yl)amino)propylthio)propane-1,2-diyl ditridecanoate (14j);

(2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl ditridecanoate (14k);

(2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl ditridecanoate (14l);

(R)-3-((S)-2-amino-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl ditridecanoate (14m);

(R)-3-((S)-2-amino-3-((1-((R)-2,3-dihydroxypropyl)-1H-1,2,3-triazol-4-yl)amino)-3-oxopropylthio)propane-1,2-diyl ditetradecanoate (15a);

(2R)-3-((2S)-2-amino-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diylditetradecanoate (15b);

(2R)-3-((2S)-2-amino-3-((1-((2S)-2-hydroxy-2-((3S,4S)-3,4,5-trihydroxytetrahydrofuran-2-yl)ethyl)-1H-1,2,3-triazol-4-yl)amino)-3-oxopropylthio)propane-1,2-diyl ditetradecanoate (15c);

(R)-3-((S)-2-amino-3-oxo-3-((1-((2S,3S,4R,5R)-2,3,4,5,6-pentahydroxyhexyl)-1H-1,2,3-triazol-4-yl)amino)propylthio)propane-1,2-diyl ditetradecanoate (15d);

(2R)-3-((2S)-2-amino-3-((1-((2S,3R,4S)-3,4-dihydroxy-5-(hydroxymethyl)tetrahydrofuran-2-yl)-1H-1,2,3-triazol-4-yl)amino)-3-oxopropylthio)propane-1,2-diyl ditetradecanoate (15e);

(2R)-3-((2S)-2-amino-3-((1-((2S,3S,4S)-3,4-dihydroxy-5-(hydroxymethyl)tetrahydrofuran-2-yl)-1H-1,2,3-triazol-4-yl)amino)-3-oxopropylthio)propane-1,2-diyl ditetradecanoate (15f);

(2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diylditetradecanoate (15g);

(2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diylditetradecanoate (15h);

(2R)-3-((2S)-2-amino-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl ditetradecanoate (15i);

(2R)-3-((2S)-2-amino-3-oxo-3-((1-((3,4,5,6-tetrahydroxytetrahydro-2H-pyran-2-yl)methyl)-1H-1,2,3-triazol-4-yl)amino)propylthio)propane-1,2-diyl ditetradecanoate (15j);

(2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl ditetradecanoate (15k);

(2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl ditetradecanoate (15l);

(R)-3-((S)-2-amino-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl ditetradecanoate (15m);

(R)-3-((S)-2-amino-3-((1-((R)-2,3-dihydroxypropyl)-1H-1,2,3-triazol-4-yl)amino)-3-oxopropylthio)propane-1,2-diyl dipentadecanoate (16a);

(2R)-3-((2S)-2-amino-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl dipentadecanoate (16b);

(2R)-3-((2S)-2-amino-3-((1-((2S)-2-hydroxy-2-((3S,4S)-3,4,5-trihydroxytetrahydrofuran-2-yl)ethyl)-1H-1,2,3-triazol-4-yl)amino)-3-oxopropylthio)propane-1,2-diyl dipentadecanoate (16c);

(R)-3-((S)-2-amino-3-oxo-3-((1-((2S,3S,4R,5R)-2,3,4,5,6-pentahydroxyhexyl)-1H-1,2,3-triazol-4-yl)amino)propylthio)propane-1,2-diyl dipentadecanoate (16d);

(2R)-3-((2S)-2-amino-3-((1-((2S,3R,4S)-3,4-dihydroxy-5-(hydroxymethyl)tetrahydrofuran-2-yl)-1H-1,2,3-triazol-4-yl)amino)-3-oxopropylthio)propane-1,2-diyl dipentadecanoate (16e);

(2R)-3-((2S)-2-amino-3-((1-((2S,3S,4S)-3,4-dihydroxy-5-(hydroxymethyl)tetrahydrofuran-2-yl)-1H-1,2,3-triazol-4-yl)amino)-3-oxopropylthio)propane-1,2-diyl dipentadecanoate (16f);

(2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dipentadecanoate (16g);

(2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dipentadecanoate (16h);

(2R)-3-((2S)-2-amino-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl dipentadecanoate (16i);

(2R)-3-((2S)-2-amino-3-oxo-3-((1-((3,4,5,6-tetrahydroxytetrahydro-2H-pyran-2-yl)methyl)-1H-1,2,3-triazol-4-yl)amino)propylthio)propane-1,2-diyl dipentadecanoate (16j);

(2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl dipentadecanoate (16k);

(2R)-3-((2S)-2-amino-3-((1-((2R)-3,4-dihydroxy-6-(hydroxymethyl)-5-(3,4,5-trihydroxy-6-(hydroxymethyl)

tetrahydro-2H-pyran-2-yloxy)tetrahydro-2H-pyran-2-yl)-1H-1,2,3-triazol-4-yl)amino)-3-oxopropylthio)propane-1,2-diyl dipentadecanoate (16l);

(R)-3-((S)-2-amino-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl dipentadecanoate (16m);

(R)-3-((S)-2-amino-3-((1-((R)-2,3-dihydroxypropyl)-1H-1,2,3-triazol-4-yl)amino)-3-oxopropylthio)propane-1,2-diyl dipalmitate (17a);

(2R)-3-((2S)-2-amino-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl dipalmitate (17b);

(2R)-3-((2S)-2-amino-3-((1-((2S)-2-hydroxy-2-((3S,4S)-3,4,5-trihydroxytetrahydrofuran-2-yl)ethyl)-1H-1,2,3-triazol-4-yl)amino)-3-oxopropylthio)propane-1,2-diyl dipalmitate (17c);

(R)-3-((S)-2-amino-3-oxo-3-((1-((2S,3S,4R,5R)-2,3,4,5,6-pentahydroxyhexyl)-1H-1,2,3-triazol-4-yl)amino)propylthio)propane-1,2-diyl dipalmitate (17d);

(2R)-3-((2S)-2-amino-3-((1-((2S,3R,4S)-3,4-dihydroxy-5-(hydroxymethyl)tetrahydrofuran-2-yl)-1H-1,2,3-triazol-4-yl)amino)-3-oxopropylthio)propane-1,2-diyl dipalmitate (17e);

(2R)-3-((2S)-2-amino-3-((1-((2S,3S,4S)-3,4-dihydroxy-5-(hydroxymethyl)tetrahydrofuran-2-yl)-1H-1,2,3-triazol-4-yl)amino)-3-oxopropylthio)propane-1,2-diyl dipalmitate (17f);

(2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dipalmitate (17g);

(2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dipalmitate (17h);

(2R)-3-((2S)-2-amino-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl dipalmitate (17i);

(2R)-3-((2S)-2-amino-3-oxo-3-((1-((3,4,5,6-tetrahydroxytetrahydro-2H-pyran-2-yl)methyl)-1H-1,2,3-triazol-4-yl)amino)propylthio)propane-1,2-diyl dipalmitate (17j);

(2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl dipalmitate (17k);

(2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl dipalmitate (17l);

(R)-3-((S)-2-amino-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl dipalmitate (17m);

(R)-3-((S)-2-amino-3-((1-((R)-2,3-dihydroxypropyl)-1H-1,2,3-triazol-4-yl)amino)-3-oxopropylthio)propane-1,2-diyl diheptadecanoate (18a);

(2R)-3-((2S)-2-amino-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl diheptadecanoate (18b);

(2R)-3-((2S)-2-amino-3-((1-((2S)-2-hydroxy-2-((3S,4S)-3,4,5-trihydroxytetrahydrofuran-2-yl)ethyl)-1H-1,2,3-triazol-4-yl)amino)-3-oxopropylthio)propane-1,2-diyl diheptadecanoate (18c);

(R)-3-((S)-2-amino-3-oxo-3-((1-((2S,3S,4R,5R)-2,3,4,5,6-pentahydroxyhexyl)-1H-1,2,3-triazol-4-yl)amino)propylthio)propane-1,2-diyl diheptadecanoate (18d);

(2R)-3-((2S)-2-amino-3-((1-((2S,3R,4S)-3,4-dihydroxy-5-(hydroxymethyl)tetrahydrofuran-2-yl)-1H-1,2,3-triazol-4-yl)amino)-3-oxopropylthio)propane-1,2-diyl diheptadecanoate (18e);

(2R)-3-((2S)-2-amino-3-((1-((2S,3S,4S)-3,4-dihydroxy-5-(hydroxymethyl)tetrahydrofuran-2-yl)-1H-1,2,3-triazol-4-yl)amino)-3-oxopropylthio)propane-1,2-diyl diheptadecanoate (18f);

(2R)-3-((2S)-2-amino-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl diheptadecanoate (18i);

(2R)-3-((2S)-2-amino-3-oxo-3-((1-((3,4,5,6-tetrahydroxytetrahydro-2H-pyran-2-yl)methyl)-1H-1,2,3-triazol-4-yl)amino)propylthio)propane-1,2-diyl diheptadecanoate (18j);

(2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl diheptadecanoate (18k);

(2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl diheptadecanoate (18l);

(R)-3-((S)-2-amino-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl diheptadecanoate (18m);

(R)-3-((S)-2-amino-3-((1-((R)-2,3-dihydroxypropyl)-1H-1,2,3-triazol-4-yl)amino)-3-oxopropylthio)propane-1,2-diyl distearate (19a);

(2R)-3-((2S)-2-amino-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl distearate (19b);

(2R)-3-((2S)-2-amino-3-((1-((2S)-2-hydroxy-2-((3S,4S)-3,4,5-trihydroxytetrahydrofuran-2-yl)ethyl)-1H-1,2,3-triazol-4-yl)amino)-3-oxopropylthio)propane-1,2-diyl distearate (19c);

(R)-3-((S)-2-amino-3-oxo-3-((1-((2S,3S,4R,5R)-2,3,4,5,6-pentahydroxyhexyl)-1H-1,2,3-triazol-4-yl)amino)propylthio)propane-1,2-diyl distearate (19d);

(2R)-3-((2S)-2-amino-3-((1-((2S,3R,4S)-3,4-dihydroxy-5-(hydroxymethyl)tetrahydrofuran-2-yl)-1H-1,2,3-triazol-4-yl)amino)-3-oxopropylthio)propane-1,2-diyl distearate (19e);

(2R)-3-((2S)-2-amino-3-((1-((2S,3S,4S)-3,4-dihydroxy-5-(hydroxymethyl)tetrahydrofuran-2-yl)-1H-1,2,3-triazol-4-yl)amino)-3-oxopropylthio)propane-1,2-diyl distearate (19f);

(2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl distearate (19g);

(2R)-3-((2S)-2-amino-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl distearate (19h);

(2R)-3-((2S)-2-amino-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl distearate (19i);

(2R)-3-((2S)-2-amino-3-oxo-3-((1-((3,4,5,6-tetrahydroxytetrahydro-2H-pyran-2-yl)methyl)-1H-1,2,3-triazol-4-yl)amino)propylthio)propane-1,2-diyl distearate (19j);

(2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl distearate (19k);

(2R)-3-((2S)-2-amino-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl distearate (19l);

(R)-3-((S)-2-amino-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl distearate (19m);

(2R)-3-((S)-3-((1-((R)-2,3-dihydroxypropyl)-1H-1,2,3-triazol-4-yl)amino)-2-hexanamido-3-oxopropylthio)propane-1,2-diyl dihexanoate (20a);

(2R)-3-((2S)-2-hexanamido-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl dihexanoate (20b);

(2R)-3-((2S)-2-hexanamido-3-((1-((2S)-2-hydroxy-2-((3S,4S)-3,4,5-trihydroxytetrahydrofuran-2-yl)ethyl)-1H-1,2,3-triazol-4-yl)amino)-3-oxopropylthio)propane-1,2-diyldihexanoate (20c);

(R)-3-((S)-2-hexanamido-3-oxo-3-((1-((2S,3S,4R,5R)-2,3,4,5,6-pentahydroxyhexyl)-1H-1,2,3-triazol-4-yl)amino)propylthio)propane-1,2-diyl dihexanoate (20d);

(2R)-3-((2S)-3-((1-((2S,3R,4S)-3,4-dihydroxy-5-(hydroxymethyl)tetrahydrofuran-2-yl)-1H-1,2,3-triazol-4-yl)amino)-2-hexanamido-3-oxopropylthio)propane-1,2-diyl dihexanoate (20e);

(2R)-3-((2S)-3-((1-((2S,3S,4S)-3,4-dihydroxy-5-(hydroxymethyl)tetrahydrofuran-2-yl)-1H-1,2,3-triazol-4-yl)amino)-2-hexanamido-3-oxopropylthio)propane-1,2-diyl dihexanoate (20f);

(2R)-3-((2S)-2-hexanamido-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyldihexanoate (20g);

(2R)-3-((2S)-2-hexanamido-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyldihexanoate (20h);

(2R)-3-((2S)-2-hexanamido-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl dihexanoate (20i);

(2R)-3-((2S)-2-hexanamido-3-oxo-3-((1-((3,4,5,6-tetrahydroxytetrahydro-2H-pyran-2-yl)methyl)-1H-1,2,3-triazol-4-yl)amino)propylthio)propane-1,2-diyl dihexanoate (20j);

(2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-2-hexanamido-3-oxopropylthio)propane-1,2-diyl dihexanoate (20k);

(2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-2-hexanamido-3-oxopropylthio)propane-1,2-diyl dihexanoate (20l);

(R)-3-((S)-2-hexanamido-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl dihexanoate (20m);

(R)-3-((S)-3-((1-((R)-2,3-dihydroxypropyl)-1H-1,2,3-triazol-4-yl)amino)-2-heptanamido-3-oxopropylthio)propane-1,2-diyl diheptanoate (21a);

(2R)-3-((2S)-2-heptanamido-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl diheptanoate (21b);

(2R)-3-((2S)-2-heptanamido-3-((1-((2S)-2-hydroxy-2-((3S,4S)-3,4,5-trihydroxytetrahydrofuran-2-yl)ethyl)-1H-1,2,3-triazol-4-yl)amino)-3-oxopropylthio)propane-1,2-diyl diheptanoate (21c);

(R)-3-((S)-2-heptanamido-3-oxo-3-((1-((2S,3S,4R,5R)-2,3,4,5,6-pentahydroxyhexyl)-1H-1,2,3-triazol-4-yl)amino)propylthio)propane-1,2-diyl diheptanoate (21d);

(2R)-3-((2S)-3-((1-((2S,3R,4S)-3,4-dihydroxy-5-(hydroxymethyl)tetrahydrofuran-2-yl)-1H-1,2,3-triazol-4-yl)amino)-2-heptanamido-3-oxopropylthio)propane-1,2-diyl diheptanoate (21e);

(2R)-3-((2S)-3-((1-((2S,3S,4S)-3,4-dihydroxy-5-(hydroxymethyl)tetrahydrofuran-2-yl)-1H-1,2,3-triazol-4-yl)amino)-2-heptanamido-3-oxopropylthio)propane-1,2-diyl diheptanoate (21f);

(2R)-3-((2S)-2-heptanamido-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl diheptanoate (21g);

(2R)-3-((2S)-2-heptanamido-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl diheptanoate (21h);

(2R)-3-((2S)-2-heptanamido-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl diheptanoate (21i);

(2R)-3-((2S)-2-heptanamido-3-oxo-3-((1-((3,4,5,6-tetrahydroxytetrahydro-2H-pyran-2-yl)methyl)-1H-1,2,3-triazol-4-yl)amino)propylthio)propane-1,2-diyl diheptanoate (21j);

(2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-2-heptanamido-3-oxopropylthio)propane-1,2-diyl diheptanoate (21k);

(2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-2-heptanamido-3-oxopropylthio)propane-1,2-diyl diheptanoate (21l);

(R)-3-((S)-2-heptanamido-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl diheptanoate (21m);

(R)-3-((S)-3-((1-((R)-2,3-dihydroxypropyl)-1H-1,2,3-triazol-4-yl)amino)-2-octanamido-3-oxopropylthio)propane-1,2-diyl dioctanoate (22a);

(2R)-3-((2S)-2-octanamido-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl dioctanoate (22b);

(2R)-3-((2S)-3-((1-((2S)-2-hydroxy-2-((3S,4S)-3,4,5-trihydroxytetrahydrofuran-2-yl)ethyl)-1H-1,2,3-triazol-4-yl)amino)-2-octanamido-3-oxopropylthio)propane-1,2-diyl dioctanoate (22c);
(R)-3-((S)-2-octanamido-3-oxo-3-((1-((2S,3S,4R,5R)-2,3,4,5,6-pentahydroxyhexyl)-1H-1,2,3-triazol-4-yl)amino)propylthio)propane-1,2-diyl dioctanoate (22d)
(2R)-3-((2S)-3-((1-((2S,3R,4S)-3,4-dihydroxy-5-(hydroxymethyl)tetrahydrofuran-2-yl)-1H-1,2,3-triazol-4-yl)amino)-2-octanamido-3-oxopropylthio)propane-1,2-diyl dioctanoate (22e);
(2R)-3-((2S)-3-((1-((2S,3S,4S)-3,4-dihydroxy-5-(hydroxymethyl)tetrahydrofuran-2-yl)-1H-1,2,3-triazol-4-yl)amino)-2-octanamido-3-oxopropylthio)propane-1,2-diyl dioctanoate (22f);
(2R)-3-((2S)-2-octanamido-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dioctanoate (22g);
(2R)-3-((2S)-2-octanamido-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dioctanoate (22h);
(2R)-3-((2S)-2-octanamido-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl dioctanoate (22i);
(2R)-3-((2S)-2-octanamido-3-oxo-3-((1-((3,4,5,6-tetrahydroxytetrahydro-2H-pyran-2-yl)methyl)-1H-1,2,3-triazol-4-yl)amino)propylthio)propane-1,2-diyl dioctanoate (22j);
(2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-2-octanamido-3-oxopropylthio)propane-1,2-diyl dioctanoate (22k);
(2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-2-octanamido-3-oxopropylthio)propane-1,2-diyl dioctanoate (22l);
(R)-3-((S)-2-octanamido-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl dioctanoate (22m);
(R)-3-((S)-3-((1-((R)-2,3-dihydroxypropyl)-1H-1,2,3-triazol-4-yl)amino)-2-nonanamido-3-oxopropylthio)propane-1,2-diyl dinonanoate (23a);
2R)-3-((2S)-2-nonanamido-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl dinonanoate (23b);
(2R)-3-((2S)-3-((1-((2S)-2-hydroxy-2-((3S,4S)-3,4,5-trihydroxytetrahydrofuran-2-yl)ethyl)-1H-1,2,3-triazol-4-yl)amino)-2-nonanamido-3-oxopropylthio)propane-1,2-diyl dinonanoate (23c);
(R)-3-((S)-2-nonanamido-3-oxo-3-((1-((2S,3S,4R,5R)-2,3,4,5,6-pentahydroxyhexyl)-1H-1,2,3-triazol-4-yl)amino)propylthio)propane-1,2-diyl dinonanoate (23d);
(2R)-3-((2S)-3-((1-((2S,3R,4S)-3,4-dihydroxy-5-(hydroxymethyl)tetrahydrofuran-2-yl)-1H-1,2,3-triazol-4-yl)amino)-2-nonanamido-3-oxopropylthio)propane-1,2-diyl dinonanoate (23e);
(2R)-3-((2S)-3-((1-((2S,3S,4S)-3,4-dihydroxy-5-(hydroxymethyl)tetrahydrofuran-2-yl)-1H-1,2,3-triazol-4-yl)amino)-2-nonanamido-3-oxopropylthio)propane-1,2-diyl dinonanoate (23f);
(2R)-3-((2S)-2-nonanamido-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dinonanoate (23g);
(2R)-3-((2S)-2-nonanamido-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dinonanoate (23h);
(2R)-3-((2S)-2-nonanamido-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl dinonanoate (23i);
(2R)-3-((2S)-2-nonanamido-3-oxo-3-((1-((3,4,5,6-tetrahydroxytetrahydro-2H-pyran-2-yl)methyl)-1H-1,2,3-triazol-4-yl)amino)propylthio)propane-1,2-diyl dinonanoate (23j);
(2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-2-nonanamido-3-oxopropylthio)propane-1,2-diyl dinonanoate (23k);
(2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-2-nonanamido-3-oxopropylthio)propane-1,2-diyl dinonanoate (23l);
(R)-3-((S)-2-nonanamido-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl dinonanoate (23m);
(R)-3-((S)-2-decanamido-3-((1-((R)-2,3-dihydroxypropyl)-1H-1,2,3-triazol-4-yl)amino)-3-oxopropylthio)propane-1,2-diyl bis(decanoate) (24a);
(2R)-3-((2S)-2-decanamido-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diylbis(decanoate) (24b);
(2R)-3-((2S)-2-decanamido-3-((1-((2S)-2-hydroxy-2-((3S,4S)-3,4,5-trihydroxytetrahydrofuran-2-yl)ethyl)-1H-1,2,3-triazol-4-yl)amino)-3-oxopropylthio)propane-1,2-diyl bis(decanoate) (24c);
(R)-3-((S)-2-decanamido-3-oxo-3-((1-((2S,3S,4R,5R)-2,3,4,5,6-pentahydroxyhexyl)-1H-1,2,3-triazol-4-yl)amino)propylthio)propane-1,2-diyl bis(decanoate) (24d);
(2R)-3-((2S)-2-decanamido-3-((1-((2S,3R,4S)-3,4-dihydroxy-5-(hydroxymethyl)tetrahydrofuran-2-yl)-1H-1,2,3-triazol-4-yl)amino)-3-oxopropylthio)propane-1,2-diyl bis(decanoate) (24e);
(2R)-3-((2S)-2-decanamido-3-((1-((2S,3S,4S)-3,4-dihydroxy-5-(hydroxymethyl)tetrahydrofuran-2-yl)-1H-1,2,3-triazol-4-yl)amino)-3-oxopropylthio)propane-1,2-diylbis(decanoate) (24f);
(2R)-3-((2S)-2-decanamido-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl bis(decanoate) (24g);
(2R)-3-((2S)-2-decanamido-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl bis(decanoate) (24h);
(2R)-3-((2S)-2-decanamido-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl bis(decanoate) (24i);

(2R)-3-((2S)-2-decanamido-3-oxo-3-((1-((3,4,5,6-tetrahydroxytetrahydro-2H-pyran-2-yl)methyl)-1H-1,2,3-triazol-4-yl)amino)propylthio)propane-1,2-diyl bis(decanoate) (24j);

(2R)-3-((2S)-2-decanamido-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl bis(decanoate) (24k);

(2R)-3-((2S)-2-decanamido-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxopropylthio)propane-1,2-diyl bis(decanoate) (24l);

(R)-3-((S)-2-decanamido-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl bis(decanoate) (24m);

(R)-3-((S)-3-((1-((R)-2,3-dihydroxypropyl)-1H-1,2,3-triazol-4-yl)amino)-3-oxo-2-undecanamidopropylthio)propane-1,2-diyl diundecanoate (25a);

(2R)-3-((2S)-3-oxo-3-((1-((2S)-3,4,5-trihydroxy-6-(hydroxymethyl)tetrahydro-2H-pyran-2-yl)-1H-1,2,3-triazol-4-yl)amino)-2-undecanamidopropylthio)propane-1,2-diyl diundecanoate (25b);

(2R)-3-((2S)-3-((1-((2S)-2-hydroxy-2-((3S,4S)-3,4,5-trihydroxytetrahydrofuran-2-yl)ethyl)-1H-1,2,3-triazol-4-yl)amino)-3-oxo-2-undecanamidopropylthio)propane-1,2-diyl diundecanoate (25c);

(R)-3-((S)-3-oxo-3-((1-((2S,3S,4R,5R)-2,3,4,5,6-pentahydroxyhexyl)-1H-1,2,3-triazol-4-yl)amino)-2-undecanamidopropylthio)propane-1,2-diyl diundecanoate (25d);

(2R)-3-((2S)-3-((1-((2S,3R,4S)-3,4-dihydroxy-5-(hydroxymethyl)tetrahydrofuran-2-yl)-1H-1,2,3-triazol-4-yl)amino)-3-oxo-2-undecanamidopropylthio)propane-1,2-diyl diundecanoate (25e);

(2R)-3-((2S)-3-((1-((2S,3S,4S)-3,4-dihydroxy-5-(hydroxymethyl)tetrahydrofuran-2-yl)-1H-1,2,3-triazol-4-yl)amino)-3-oxo-2-undecanamidopropylthio)propane-1,2-diyl diundecanoate (25f);

(2R)-3-((2S)-3-oxo-3-((1-(4(2R)-3,4,5-trihydroxy-6-(hydroxymethyl)tetrahydro-2H-pyran-2-yl)-1H-1,2,3-triazol-4-yl)methylamino)-2-undecanamidopropylthio)propane-1,2-diyl diundecanoate (25g);

(2R)-3-((2S)-3-oxo-3-((1-((2R)-3,4,5-trihydroxy-6-(hydroxymethyl)tetrahydro-2H-pyran-2-yl)-1H-1,2,3-triazol-4-yl)amino)-2-undecanamidopropylthio)propane-1,2-diyl diundecanoate (25h);

(2R)-3-((2S)-3-oxo-3-((1-(3,4,5-trihydroxy-6-(hydroxymethyl)tetrahydro-2H-pyran-2-yl)-1H-1,2,3-triazol-4-yl)amino)-2-undecanamidopropylthio)propane-1,2-diyl diundecanoate (25i);

(2R)-3-((2S)-3-oxo-3-((1-((3,4,5,6-tetrahydroxytetrahydro-2H-pyran-2-yl)methyl)-1H-1,2,3-triazol-4-yl)amino)-2-undecanamidopropylthio)propane-1,2-diyl diundecanoate (25j);

(2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxo-2-undecanamidopropylthio)propane-1,2-diyl diundecanoate (25k);

(2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxo-2-undecanamidopropylthio)propane-1,2-diyl diundecanoate (25l);

(R)-3-((S)-3-oxo-3-((1-((1S,2S,3R,4S,5S,6S)-2,3,4,5,6-pentahydroxycyclohexyl)-1H-1,2,3-triazol-4-yl)amino)-2-undecanamidopropylthio)propane-1,2-diyl diundecanoate (25m);

(R)-3-((S)-3-((1-((R)-2,3-dihydroxypropyl)-1H-1,2,3-triazol-4-yl)amino)-2-dodecanamido-3-oxopropylthio)propane-1,2-diyl didodecanoate (26a);

(2R)-3-((2S)-2-dodecanamido-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl didodecanoate (26b);

(2R)-3-((2S)-2-dodecanamido-3-((1-((2S)-2-hydroxy-2-((3S,4S)-3,4,5-trihydroxytetrahydrofuran-2-yl)ethyl)-1H-1,2,3-triazol-4-yl)amino)-3-oxopropylthio)propane-1,2-diyl didodecanoate (26c);

(R)-3-((S)-2-dodecanamido-3-oxo-3-((1-((2S,3S,4R,5R)-2,3,4,5,6-pentahydroxyhexyl)-1H-1,2,3-triazol-4-yl)amino)propylthio)propane-1,2-diyl didodecanoate (26d);

(2R)-3-((2S)-3-((1-((2S,3R,4S)-3,4-dihydroxy-5-(hydroxymethyl)tetrahydrofuran-2-yl)-1H-1,2,3-triazol-4-yl)amino)-2-dodecanamido-3-oxopropylthio)propane-1,2-diyl didodecanoate (26e);

(2R)-3-((2S)-3-((1-((2S,3S,4S)-3,4-dihydroxy-5-(hydroxymethyl)tetrahydrofuran-2-yl)-1H-1,2,3-triazol-4-yl)amino)-2-dodecanamido-3-oxopropylthio)propane-1,2-diyl didodecanoate (26f);

(2R)-3-((2S)-2-dodecanamido-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl didodecanoate (26g);

(2R)-3-((2S)-2-dodecanamido-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl didodecanoate (26h);

(2R)-3-((2S)-2-dodecanamido-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl didodecanoate (26i);

(2R)-3-((2S)-2-dodecanamido-3-oxo-3-((1-((3,4,5,6-tetrahydroxy-tetrahydro-2H-pyran-2-yl)methyl)-1H-1,2,3-triazol-4-yl)amino)propylthio)propane-1,2-diyl didodecanoate (26j);

(2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-2-dodecanamido-3-oxopropylthio)propane-1,2-diyl didodecanoate (26k);

(2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-2-dodecanamido-3-oxopropylthio)propane-1,2-diyl didodecanoate (26l);

(R)-3-((S)-2-dodecanamido-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl didodecanoate (26m);

(R)-3-((S)-3-((1-((R)-2,3-dihydroxypropyl)-1H-1,2,3-triazol-4-yl)amino)-3-oxo-2-tridecanamidopropylthio)propane-1,2-diyl ditridecanoate (27a);

(2R)-3-((2S)-3-oxo-2-tridecanamido-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl ditridecanoate (27b);

(2R)-3-((2S)-3-((1-((2S)-2-hydroxy-2-((3S,4S)-3,4,5-trihydroxytetrahydrofuran-2-yl)ethyl)-1H-1,2,3-triazol-4-yl)amino)-3-oxo-2-tridecanamidopropylthio)propane-1,2-diyl ditridecanoate (27c);

(R)-3-((S)-3-oxo-3-((1-((2S,3S,4R,5R)-2,3,4,5,6-pentahydroxyhexyl)-1H-1,2,3-triazol-4-yl)amino)-2-tridecanamidopropylthio)propane-1,2-diyl ditridecanoate (27d);

(2R)-3-((2S)-3-((1-((2S,3R,4S)-3,4-dihydroxy-5-(hydroxymethyl)tetrahydrofuran-2-yl)-1H-1,2,3-triazol-4-yl)amino)-3-oxo-2-tridecanamidopropylthio)propane-1,2-diyl ditridecanoate (27e);

(2R)-3-((2S)-3-((1-((2S,3S,4S)-3,4-dihydroxy-5-(hydroxymethyl)tetrahydrofuran-2-yl)-1H-1,2,3-triazol-4-yl)amino)-3-oxo-2-tridecanamidopropylthio)propane-1,2-diyl ditridecanoate (27f) (2R)-3-((2S)-3-oxo-2-tridecanamido-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl ditridecanoate (27g);

(2R)-3-((2S)-3-oxo-2-tridecanamido-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl ditridecanoate (27h);

(2R)-3-((2S)-3-oxo-2-tridecanamido-3-((1-(3,4,5-trihydroxy-6-(hydroxymethyl)tetrahydro-2H-pyran-2-yl)-1H-1,2,3-triazol-4-yl)amino)propylthio)propane-1,2-diyl ditridecanoate (27i);

(2R)-3-((2S)-3-oxo-3-((1-((3,4,5,6-tetrahydroxytetrahydro-2H-pyran-2-yl)methyl)-1H-1,2,3-triazol-4-yl)amino)-2-tridecanamidopropylthio)propane-1,2-diyl ditridecanoate (27j);

(2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxo-2-tridecanamidopropylthio)propane-1,2-diyl ditridecanoate (27k);

(2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxo-2-tridecanamidopropylthio)propane-1,2-diyl ditridecanoate (27l);

(R)-3-((S)-3-oxo-3-((1-((1S,2S,3R,4S,5S,6S)-2,3,4,5,6-pentahydroxycyclohexyl)-1H-1,2,3-triazol-4-yl)amino)-2-tridecanamidopropylthio)propane-1,2-diyl ditridecanoate (27m);

(R)-3-((S)-3-((1-((R)-2,3-dihydroxypropyl)-1H-1,2,3-triazol-4-yl)amino)-3-oxo-2-tetradecanamidopropylthio)propane-1,2-diyl ditetradecanoate (28a);

(2R)-3-((2S)-3-oxo-2-tetradecanamido-3-((1-((2S)-3,4,5-trihydroxy-6(hydroxymethyl)tetrahydro-2H-pyran-2-yl)-1H-1,2,3-triazol-4-yl)amino)propylthio)propane-1,2-diyl ditetradecanoate (28b);

(2R)-3-((2S)-3-((1-((2S)-2-hydroxy-2-((3S,4S)-3,4,5-trihydroxytetra-hydrofuran-2-yl)ethyl)-1H-1,2,3-triazol-4-yl)amino)-3-oxo-2-tetradecanamidopropylthio)propane-1,2-diyl ditetradecanoate (28c);

(R)-3-((S)-3-oxo-3-((1-((2S,3S,4R,5R)-2,3,4,5,6-pentahydroxyhexyl)-1H-1,2,3-triazol-4-yl)amino)-2-tetradecanamidopropylthio)propane-1,2-diyl ditetradecanoate (28d);

(2R)-3-((2S)-3-((1-((2S,3R,4S)-3,4-dihydroxy-5-(hydroxymethyl)tetrahydrofuran-2-yl)-1H-1,2,3-triazol-4-yl)amino)-3-oxo-2-tetradecanamidopropylthio)propane-1,2-diyl ditetradecanoate (28e);

(2R)-3-((2S)-3-((1-((2S,3S,4S)-3,4-dihydroxy-5-(hydroxymethyl)tetrahydrofuran-2-yl)-1H-1,2,3-triazol-4-yl)amino)-3-oxo-2-tetradecanamidopropylthio)propane-1,2-diyl ditetradecanoate (28f);

(2R)-3-((2S)-3-oxo-2-tetradecanamido-3-((1-((2R)-3,4,5-trihydroxy-6(hydroxymethyl)tetrahydro-2H-pyran-2-yl)-1H-1,2,3-triazol-4-yl)amino)propylthio)propane-1,2-diyl ditetradecanoate (28g);

(2R)-3-((2S)-3-oxo-2-tetradecanamido-3-((1-((2R)-3,4,5-trihydroxy-6(hydroxymethyl)tetrahydro-2H-pyran-2-yl)-1H-1,2,3-triazol-4-yl)amino)propylthio)propane-1,2-diyl ditetradecanoate (28h);

(R)-3-((S)-3-((1-((R)-2,3-dihydroxypropyl)-1H-1,2,3-triazol-4-yl)amino)-3-oxo-2-pentadecanamido-propylthio)propane-1,2-diyl dipentadecanoate (29a);

(2R)-3-((2S)-3-oxo-2-pentadecanamido-3-((1-((2S)-3,4,5-trihydroxy-(hydroxymethyl)tetrahydro-2H-pyran-2-yl)-1H-1,2,3-triazol-4-yl)amino)propylthio)propane-1,2-diyldipentadecanoate (29b);

(2R)-3-((2S)-3-((1-((2S)-2-hydroxy-2-((3S,4S)-3,4,5-trihydroxytetrahydrofuran-2-yl)ethyl)-1H-1,2,3-triazol-4-yl)amino)-3-oxo-2-pentadecanamidopropylthio)propane-1,2-diyl dipentadecanoate (29c);

(R)-3-((S)-3-oxo-2-pentadecanamido-3-((1-((2S,3S,4R,5R)-2,3,4,5,6-pentahydroxyhexyl)-1H-1,2,3-triazol-4-yl)amino)propylthio)propane-1,2-diyl dipentadecanoate (29d);

(2R)-3-((2S)-3-((1-((2S,3R,4S)-3,4-dihydroxy-5-(hydroxymethyl)tetrahydrofuran-2-yl)-1H-1,2,3-triazol-4-yl)amino)-3-oxo-2-pentadecanamidopropylthio)propane-1,2-diyl dipentadecanoate (29e);

(2R)-3-((2S)-3-((1-((2S,3S,4S)-3,4-dihydroxy-5-(hydroxymethyl)tetrahydrofuran-2-yl)-1H-1,2,3-triazol-4-yl)amino)-3-oxo-2-pentadecanamidopropylthio)propane-1,2-diyl dipentadecanoate (29f);

(2R)-3-((2S)-3-oxo-2-pentadecanamido-3-((1-((2R)-3,4,5-trihydroxy-(hydroxymethyl)tetrahydro-2H-pyran-2-yl)-1H-1,2,3-triazol-4-yl)amino)propylthio)propane-1,2-diyl dipentadecanoate (29g);

(2R)-3-((2S)-3-oxo-2-pentadecanamido-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dipentadecanoate (29h);

(2R)-3-((2S)-3-oxo-2-pentadecanamido-3-((1-(3,4,5-trihydroxy-6-(hydroxymethyl)tetrahydro-2H-pyran-2-yl)-1H-1,2,3-triazol-4-yl)amino)propylthio)propane-1,2-diyl dipentadecanoate (29i);

(2R)-3-((2S)-3-oxo-2-pentadecanamido-3-((1-((3,4,5,6-tetrahydroxytetrahydro-2H-pyran-2-yl)methyl)-1H-1,2,3-triazol-4-yl)amino)propylthio)propane-1,2-diyl dipentadecanoate (29j);

(2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxo-2-pentadecanamidopropylthio)propane-1,2-diyl dipentadecanoate (29k);

(2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxo-2-pentadecanamido-propylthio)propane-1,2-diyl dipentadecanoate (29l);

(R)-3-((S)-3-oxo-2-pentadecanamido-3-((1-((1S,2S,3R,4S,5S,6S)-2,3,4,5,6-pentahydroxycyclohexyl)-1H-1,2,3-triazol-4-yl)amino)propylthio)propane-1,2-diyl dipentadecanoate (29m);

(R)-3-((S)-3-((1-((R)-2,3-dihydroxypropyl)-1H-1,2,3-triazol-4-yl)amino)-3-oxo-2-palmitamidopropylthio)propane-1,2-diyl dipalmitate (30a);

(2R)-3-((2S)-3-oxo-2-palmitamido-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl dipalmitate (30b);

(2R)-3-((2S)-3-((1-((2S)-2-hydroxy-2-((3S,4S)-3,4,5-trihydroxytetrahydrofuran-2-yl)ethyl)-1H-1,2,3-triazol-4-yl)amino)-3-oxo-2-palmitamidopropylthio)propane-1,2-diyl dipalmitate (30c);

(R)-3-((S)-3-oxo-2-palmitamido-3-((1-((2S,3S,4R,5R)-2,3,4,5,6-pentahydroxyhexyl)-1H-1,2,3-triazol-4-yl)amino)propylthio)propane-1,2-diyl dipalmitate (30d);

(2R)-3-((2S)-3-((1-((2S,3R,4S)-3,4-dihydroxy-5-(hydroxymethyl)tetrahydrofuran-2-yl)-1H-1,2,3-triazol-4-yl)amino)-3-oxo-2-palmitamidopropylthio)propane-1,2-diyl dipalmitate (30e);

(2R)-3-((2S)-3-((1-((2S,3S,4S)-3,4-dihydroxy-5-(hydroxymethyl)tetrahydrofuran-2-yl)-1H-1,2,3-triazol-4-yl)amino)-3-oxo-2-palmitamidopropylthio)propane-1,2-diyl dipalmitate (30f);

(2R)-3-((2S)-3-oxo-2-palmitamido-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dipalmitate (30g);

(2R)-3-((2S)-3-oxo-2-palmitamido-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl dipalmitate (30h);

(2R)-3-((2S)-3-oxo-2-palmitamido-3-((1-(3,4,5-trihydroxy-6-(hydroxymethyl)tetrahydro-2H-pyran-2-yl)-1H-1,2,3-triazol-4-yl)amino)propylthio)propane-1,2-diyl dipalmitate (30i);

(2R)-3-((2S)-3-oxo-2-palmitamido-3-((1-((3,4,5,6-tetrahydroxytetrahydro-2H-pyran-2-yl)methyl)-1H-1,2,3-triazol-4-yl)amino)propylthio)propane-1,2-diyl dipalmitate (30j);

(2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxo-2-palmitamidopropylthio)propane-1,2-diyl dipalmitate (30k);

(2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxo-2-palmitamidopropylthio)propane-1,2-diyl dipalmitate (30l);

(R)-3-((S)-3-oxo-2-palmitamido-3-((1-((1S,2S,3R,4S,5S,6S)-2,3,4,5,6-pentahydroxycyclohexyl)-1H-1,2,3-triazol-4-yl)amino)propylthio)propane-1,2-diyl dipalmitate (30m);

(R)-3-((S)-3-((1-((R)-2,3-dihydroxypropyl)-1H-1,2,3-triazol-4-yl)amino)-2-heptadecanamido-3-oxopropylthio)propane-1,2-diyl diheptadecanoate (31a);

(2R)-3-((2S)-2-heptadecanamido-3-oxo-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl diheptadecanoate (31b);

(2R)-3-((2S)-2-heptadecanamido-3-((1-((2S)-2-hydroxy-2-((3S,4S)-3,4,5-trihydroxytetrahydrofuran-2-yl)ethyl)-1H-1,2,3-triazol-4-yl)amino)-3-oxopropylthio)propane-1,2-diyl diheptadecanoate (31c);

(R)-3-((S)-2-heptadecanamido-3-oxo-3-((1-((2S,3S,4R,5R)-2,3,4,5,6-pentahydroxyhexyl)-1H-1,2,3-triazol-4-yl)amino)propylthio)propane-1,2-diyl diheptadecanoate (31d);

(2R)-3-((2S)-3-((1-((2S,3R,4S)-3,4-dihydroxy-5-(hydroxymethyl)tetrahydrofuran-2-yl)-1H-1,2,3-triazol-4-yl)amino)-2-heptadecanamido-3-oxopropylthio)propane-1,2-diyl diheptadecanoate (31e);

(2R)-3-((2S)-3-((1-((2S,3S,4S)-3,4-dihydroxy-5-(hydroxymethyl)tetrahydrofuran-2-yl)-1H-1,2,3-triazol-4-yl)amino)-2-heptadecanamido-3-oxopropylthio)propane-1,2-diyl diheptadecanoate (31f);

(2R)-3-((2S)-2-heptadecanamido-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl diheptadecanoate (31g);

(2R)-3-((2S)-2-heptadecanamido-3-oxo-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyldiheptadecanoate (31h);

(2R)-3-((2S)-2-heptadecanamido-3-oxo-3-((1-(3,4,5-trihydroxy-6-(hydroxymethyl)tetrahydro-2H-pyran-2-yl)-1H-1,2,3-triazol-4-yl)amino)propylthio)propane-1,2-diyl diheptadecanoate (31i);

(2R)-3-((2S)-2-heptadecanamido-3-oxo-3-((1-((3,4,5,6-tetrahydroxytetrahydro-2H-pyran-2-yl)methyl)-1H-1,2,3-triazol-4-yl)amino)propylthio)propane-1,2-diyl diheptadecanoate (31j);

(2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-2-heptadecanamido-3-oxopropylthio)propane-1,2-diyl diheptadecanoate (31k);

(2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-2-heptadecanamido-3-oxopropylthio)propane-1,2-diyl diheptadecanoate (31l);

(R)-3-((S)-2-heptadecanamido-3-oxo-3-((1-((1S,2S,3R,4S,5S,6S)-2,3,4,5,6-pentahydroxycyclohexyl)-1H-1,2,3-triazol-4-yl)amino)propylthio)propane-1,2-diyl diheptadecanoate (31m);

(R)-3-((S)-3-((1-((R)-2,3-dihydroxypropyl)-1H-1,2,3-triazol-4-yl)amino)-3-oxo-2-stearamidopropylthio)propane-1,2-diyl distearate (32a);

(2R)-3-((2S)-3-oxo-2-stearamido-3-((1-((2S)-3,4,5-trihydroxy-6-(hydroxymethyl)tetrahydro-2H-pyran-2-yl)-1H-1,2,3-triazol-4-yl)amino)propylthio)propane-1,2-diyl distearate (32b);

(2R)-3-((2S)-3-((1-((2S)-2-hydroxy-2-((3S,4S)-3,4,5-trihydroxytetrahydrofuran-2-yl)ethyl)-1H-1,2,3-triazol-4-yl)amino)-3-oxo-2-stearamidopropylthio)propane-1,2-diyl distearate (32c);

(R)-3-((S)-3-oxo-3-((1-((2S,3S,4R,5R)-2,3,4,5,6-pentahydroxyhexyl)-1H-1,2,3-triazol-4-yl)amino)-2-stearamidopropylthio)propane-1,2-diyl distearate (32d);

(2R)-3-((2S)-3-((1-((2S,3R,4S)-3,4-dihydroxy-5-(hydroxymethyl)tetrahydrofuran-2-yl)-1H-1,2,3-triazol-4-yl)amino)-3-oxo-2-stearamidopropylthio)propane-1,2-diyl distearate (32e);

(2R)-3-((2S)-3-((1-((2S,3S,4S)-3,4-dihydroxy-5-(hydroxymethyl)tetrahydrofuran-2-yl)-1H-1,2,3-triazol-4-yl)amino)-3-oxo-2-stearamidopropylthio)propane-1,2-diyl distearate (32f);

(2R)-3-((2S)-3-oxo-2-stearamido-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl distearate (32g);

(2R)-3-((2S)-3-oxo-2-stearamido-3-((1-((2R)-3,4,5-trihydroxy-6-(hydroxymethyl)tetrahydro-2H-pyran-2-yl)-1H-1,2,3-triazol-4-yl)amino)propylthio)propane-1,2-diyl distearate (32h);

(2R)-3-((2S)-3-oxo-2-stearamido-3-((1-(3,4,5-trihydroxy-6-(hydroxymethyl)tetrahydro-2H-pyran-2-yl)-1H-1,2,3-triazol-4-yl)amino)propylthio)propane-1,2-diyl distearate (32i);

(2R)-3-((2S)-3-oxo-2-stearamido-3-((1-((3,4,5,6-tetrahydroxytetrahydro-2H-pyran-2-yl)methyl)-1H-1,2,3-triazol-4-yl)amino)propylthio)propane-1,2-diyl distearate (32j);

(2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxo-2-stearamidopropylthio)propane-1,2-diyl distearate (32k);

(2R)-3-((2S)-3-((1-((2R)-3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yl)-1H-1,2,3-triazol-4-yl)amino)-3-oxo-2-stearamidopropylthio)propane-1,2-diyl distearate (32l); and (R)-3-((S)-3-oxo-3-((1-((1S,2S,3R,4S,5S,6S)-2,3,4,5,6-pentahydroxycyclohexyl)-1H-1,2,3-triazol-4-yl)amino)-2-stearamidopropylthio)propane-1,2-diyl distearate (32m).

3. The vaccine adjuvant conjugate as claimed in claim 1, wherein R is selected from hydroxyl-cycloalkanes in all their stereoisomeric forms.

4. A vaccine composition comprising the adjuvant of claim 1 and at least one antigen wherein the antigen is selected as a single or multiple component(s) from the group consisting of a protein of a pathogen, a recombinant protein, a peptide, a hapten, a polysaccharide, a glycoprotein, a lipopolysaccharide, a DNA molecule (polynucleotide), a cancer cell, a micro-organism, and mixtures thereof.

5. The vaccine composition as claimed in claim 4, wherein the vaccine is capable of efficiently inducing cell mediated immune response and producing antigen-specific antibodies.

6. The vaccine composition as claimed in claim 4, wherein the triazolyl adjuvant is capable of inducing long lasting antibodies for cell mediated immunity.

7. The vaccine composition as claimed in claim 4, wherein the triazolyl adjuvant of this invention is capable of inducing Th1 activation as evidence by the expression of cytokine response.

* * * * *